United States Patent
Kirchfield

(10) Patent No.: US 9,522,940 B2
(45) Date of Patent: Dec. 20, 2016

(54) LIPOCALIN MUTEINS WITH BINDING-AFFINITY FOR GLYPICAN-3 (GPC-3) AND USE OF LIPOCALIN MUTEINS FOR TARGET-SPECIFIC DELIVERY TO CELLS EXPRESSING GPC-3

(71) Applicant: PIERIS AG, Freising-Weihenstephan (DE)

(72) Inventor: Klaus Kirchfield, Petershausen (DE)

(73) Assignee: Pieris Pharmaceuticals GmbH, Freising (DE)

( * ) Notice: Subject to any disclaimer, the term of this patent is extended or adjusted under 35 U.S.C. 154(b) by 66 days.

(21) Appl. No.: 14/402,438

(22) PCT Filed: May 21, 2013

(86) PCT No.: PCT/EP2013/060354
§ 371 (c)(1),
(2) Date: Nov. 20, 2014

(87) PCT Pub. No.: WO2013/174783
PCT Pub. Date: Nov. 28, 2013

(65) Prior Publication Data
US 2015/0284435 A1  Oct. 8, 2015

Related U.S. Application Data

(60) Provisional application No. 61/650,745, filed on May 23, 2012.

(51) Int. Cl.
*C07K 14/14* (2006.01)
*C07K 14/47* (2006.01)
*C07K 14/435* (2006.01)
*A61K 49/00* (2006.01)
*G01N 33/574* (2006.01)

(52) U.S. Cl.
CPC ......... *C07K 14/435* (2013.01); *A61K 49/0004* (2013.01); *C07K 14/47* (2013.01); *G01N 33/57492* (2013.01); *G01N 2333/705* (2013.01)

(58) Field of Classification Search
CPC ........ C97K 14/14; C97K 14/47; C97K 14/435
See application file for complete search history.

(56) References Cited

U.S. PATENT DOCUMENTS

| | | | | |
|---|---|---|---|---|
| 7,585,940 B2 * | 9/2009 | Skerra | ............. | C07K 14/47 530/350 |
| 8,313,924 B2 * | 11/2012 | Jensen | ............. | C07K 14/47 435/320.1 |
| 8,986,951 B2 * | 3/2015 | Hohlbaum | ......... | A61K 38/1709 435/320.1 |
| 9,260,492 B2 * | 2/2016 | Matschiner | ............ | C07K 14/47 |
| 2013/0225505 A1 * | 8/2013 | Robinson | ............ | C07K 14/435 514/20.8 |

FOREIGN PATENT DOCUMENTS

| | | |
|---|---|---|
| WO | WO 2008/015239 A2 | 2/2008 |
| WO | WO 2011/069992 A2 | 6/2011 |
| WO | WO 2011/149962 A1 | 12/2011 |
| WO | WO 2011/154420 A2 | 12/2011 |
| WO | WO 2012/065978 A1 | 5/2012 |

OTHER PUBLICATIONS

Aina et al., "From Combinatorial Chemistry to Cancer-Targeting Peptides," Molecular Pharmaceutics, Oct. 1, 2007, 4(5):631-651.
Ho et al,, "Glypican-3: A new target for cancer immunotherapy," European Journal of Cancer, Feb. 2011, 47(3):333-338.
Lee et al., "Targeting of hepatocellular carcinoma with glypican-3-targeting peptide ligand," Journal of Peptide Science, published online Oct. 4, 2011, 17(11):763-769.

* cited by examiner

*Primary Examiner* — Karen Cochrane Carlson
(74) *Attorney, Agent, or Firm* — Foley & Lardner LLP

(57) ABSTRACT

The present invention relates to novel, specific-binding therapeutic and/or diagnostic lipocalin muteins directed against Glypican-3 (GPC-3). The invention also relates to nucleic acid molecules encoding such muteins and to methods for generation of such muteins and nucleic acid molecules. In addition, the invention also is directed to pharmaceutical compositions comprising such muteins and practical uses of these lipocalin muteins. In addition, the present invention provides methods of using muteins of human lipocalin 2 (Lcn2 or NGAL) for target-specific delivery of therapeutic moieties or detectable labels to cells expressing GPC-3, and related therapeutic and diagnostic utilization.

17 Claims, 8 Drawing Sheets

SK-HEP1::hGPC3

SK-HEP1::hGPC3

| | 116 | 117 | 118 | 119 | 120 | 121 | 122 | 123 | 124 | 125 | 126 | 127 | 128 | 129 | 130 | 131 | 132 | 133 | 134 | 135 | 136 | 137 | 138 | 139 | 140 | 141 | 142 | 143 | 144 | 145 | 146 | 147 |
|---|---|---|---|---|---|---|---|---|---|---|---|---|---|---|---|---|---|---|---|---|---|---|---|---|---|---|---|---|---|---|---|---|
| | V | G | R | D | P | K | N | N | L | E | A | L | E | D | F | E | K | A | A | G | A | R | G | L | S | T | E | S | I | L | I | P |
| | V | G | R | D | P | K | N | N | L | E | A | L | E | D | F | E | K | A | A | G | A | R | G | L | S | T | E | S | I | L | I | P |
| | V | G | R | D | P | K | N | N | L | E | A | L | E | D | F | E | K | A | A | G | A | R | G | L | S | T | E | S | I | L | I | P |
| | V | G | R | D | P | K | N | N | L | E | A | L | E | D | F | E | K | A | A | G | A | R | G | L | S | T | E | S | I | L | I | P |
| | V | G | R | D | P | K | N | N | L | E | A | L | E | D | F | E | K | A | A | G | A | R | G | L | S | T | E | S | I | L | I | P |
| | V | G | R | D | P | K | N | N | L | E | A | L | E | D | F | E | K | A | A | G | A | R | G | L | S | T | E | S | I | L | I | P |
| | V | G | R | D | P | K | N | N | L | E | A | L | E | D | F | E | K | A | A | G | A | R | G | L | S | T | E | S | I | L | I | P |
| | V | G | R | D | P | K | N | N | L | E | A | L | E | D | F | E | K | A | A | G | A | R | G | L | S | T | E | S | I | L | I | P |
| | V | G | R | D | P | K | N | N | L | E | A | L | E | D | F | E | K | A | A | G | A | R | G | L | S | T | E | S | I | L | I | P |
| | V | G | R | D | P | K | N | N | L | E | A | L | E | D | F | E | K | A | A | G | A | R | G | L | S | T | E | S | I | L | I | P |
| | V | G | R | D | P | K | N | N | L | E | A | L | E | D | F | E | K | A | A | G | A | R | G | L | S | T | E | S | I | L | I | P |
| | V | G | R | D | P | K | N | N | L | E | A | L | E | D | F | E | K | A | A | G | A | R | G | L | S | T | E | S | I | L | I | P |
| | V | G | R | D | P | K | N | N | L | E | A | L | E | D | F | E | K | A | A | G | A | R | G | L | S | T | E | S | I | L | I | P |
| | V | G | R | D | P | K | N | N | L | E | A | L | E | D | F | E | K | A | A | G | A | R | G | L | S | T | E | S | I | L | I | P |
| | V | G | R | D | P | K | N | N | L | E | A | L | E | D | F | E | K | A | A | G | A | R | G | L | S | T | E | S | I | L | I | P |
| | V | G | R | D | P | K | N | N | L | E | A | L | E | D | F | E | K | A | A | G | A | R | G | L | S | T | E | S | I | L | I | P |
| | V | G | R | D | P | K | N | N | L | E | A | L | E | D | F | E | K | A | A | G | A | R | G | L | S | T | E | S | I | L | I | P |
| | V | G | R | D | P | K | N | N | L | E | A | L | E | D | F | E | K | A | A | G | A | R | G | L | S | T | E | S | I | L | I | P |
| | V | G | R | D | P | K | N | N | L | E | A | L | E | D | F | E | K | A | A | G | A | R | G | L | S | T | E | S | I | L | I | P |
| | V | G | R | D | P | K | N | N | L | E | A | L | E | D | F | E | K | A | A | G | A | R | G | L | S | T | E | S | I | L | I | P |
| | V | G | R | D | P | K | N | N | L | E | A | L | E | D | F | E | K | A | A | G | A | R | G | L | S | T | E | S | I | L | I | P |
| | V | G | R | D | P | K | N | N | L | E | A | L | E | D | F | E | K | A | A | G | A | R | G | L | S | T | E | S | I | L | I | P |
| | V | G | R | D | P | K | N | N | L | E | A | L | E | D | F | E | K | A | A | G | A | R | G | L | S | T | E | S | I | L | I | P |
| | V | G | R | D | P | K | N | N | L | E | A | L | E | D | F | E | K | A | A | G | A | R | G | L | S | T | E | S | I | L | I | P |
| | V | G | R | D | P | K | N | N | L | E | A | L | E | D | F | E | K | A | A | G | A | R | G | L | S | T | E | S | I | L | I | P |
| | V | G | R | D | P | K | N | N | L | E | A | L | E | D | F | E | K | A | A | G | A | R | G | L | S | T | E | S | I | L | I | P |
| | V | G | R | D | P | K | N | N | L | E | A | L | E | D | F | E | K | A | A | G | A | R | G | L | S | T | E | S | I | L | I | P |
| | V | G | R | D | P | K | N | N | L | E | A | L | E | D | F | E | K | A | A | G | A | R | G | L | S | T | E | S | I | L | I | P |
| | V | G | R | D | P | K | N | N | L | E | A | L | E | D | F | E | K | A | A | G | A | R | G | L | S | T | E | S | I | L | I | P |

Figure 5 (cont'd)

| | 148 | 149 | 150 | 151 | 152 | 153 | 154 | 155 | 156 | 157 | 158 | IC50 [nM] | EC50 [nM] |
|---|---|---|---|---|---|---|---|---|---|---|---|---|---|
| | R | Q | S | E | T | C | S | P | G | S | D | | |
| | R | Q | S | E | T | S | S | P | G | | | 32.07 | |
| | R | Q | S | E | T | S | S | P | G | | | 276.2 | |
| | R | Q | S | E | T | S | S | P | G | | | 9.744 | |
| | R | Q | S | E | T | S | S | P | G | | | 15.42 | |
| | R | Q | S | E | T | S | S | P | G | | | 251.6 | |
| | R | Q | S | E | T | S | S | P | G | | | 1.45 | |
| | R | Q | S | E | T | S | S | P | G | | | 258.1 | |
| | R | Q | S | E | T | S | S | P | G | | | 43.52 | |
| | R | Q | S | E | T | S | S | P | G | | | | 3.75 |
| | R | Q | S | E | T | S | S | P | G | | | | 0.9 |
| | R | Q | S | E | T | S | S | P | G | | | | 22.2 |
| | R | Q | S | E | T | S | S | P | G | | | | 31.2 |
| | R | Q | S | E | T | S | S | P | G | | | | 0.47 |
| | R | Q | S | E | T | S | S | P | G | | | | 2.8 |
| | R | Q | S | E | T | S | S | P | G | | | | 2.6 |
| | R | Q | S | E | T | S | S | P | G | | | | 10 |
| | R | Q | S | E | T | S | S | P | G | | | | 28 |
| | R | Q | S | E | T | S | S | P | G | | | | 4.6 |
| | R | Q | S | E | T | S | S | P | G | | | | 3.2 |
| | R | Q | S | E | T | S | S | P | G | | | | 2.9 |
| | R | Q | S | E | T | S | S | P | G | | | | 20 |
| | R | Q | S | E | T | S | S | P | G | | | | 4 |
| | R | Q | S | E | T | S | S | P | G | | | | 13.5 |
| | R | Q | S | E | T | S | S | P | G | | | | 4.5 |
| | R | Q | S | E | T | S | S | P | G | | | | 62 |
| | R | Q | S | E | T | S | S | P | G | | | | 2.4 |
| | R | Q | S | E | T | S | S | P | G | | | | 1.1 |
| | R | Q | S | E | T | S | S | P | G | | | | 4.5 |
| | R | Q | S | E | T | S | S | P | G | | | | 12.6 |
| | R | Q | S | E | T | S | S | P | G | | | | 1.4 |
| | R | Q | S | E | T | S | S | P | G | | | | 7 |
| | R | Q | S | E | T | S | S | P | G | | | | 6 |
| | R | Q | S | E | T | S | S | P | G | | | | 19 |
| | R | Q | S | E | T | S | S | P | G | | | | |

Figure 5 (cont'd)

LIPOCALIN MUTEINS WITH BINDING-AFFINITY FOR GLYPICAN-3 (GPC-3) AND USE OF LIPOCALIN MUTEINS FOR TARGET-SPECIFIC DELIVERY TO CELLS EXPRESSING GPC-3

CROSS-REFERENCE TO RELATED APPLICATIONS

This application is a National Stage application of PCT/EP2013/060354, filed May 21, 2013, which claims priority from U.S. Provisional Application No. 61/650,745, filed May 23, 2012.

The instant application contains a Sequence Listing which has been submitted in ASCII format via EFS-WEB and is hereby incorporated by reference in its entirety. Said ASCII copy, created on Jul. 12, 2016, is named 029029-0155 SL.txt and is 68,178 bytes in size.

BACKGROUND

Muteins of various lipocalins are a rapidly expanding class of therapeutics. Indeed, lipocalin muteins can be constructed to exhibit a high affinity and specificity against a target that is different than a natural ligand of wild type lipocalins (e.g., WO 99/16873, WO 00/75308, WO 03/029463, WO 03/029471 and WO 05/19256). In particular, international patent application PCT/EP2011/070119 disclosed lipocalin muteins, derived from human lipocalin 2 (or hNGAL), which are capable of binding Glypican-3 (GPC-3).

Glypican-3 (GPC-3), whose expression has been implicated in many cancers, belongs to the glypican family of glycosyl-phosphatidylinositol-anchored heparin sulfate proteoglycans. (Sasisekharan et al., Nature Reviews I Cancer, Volume 2 (2002).) GPC3 is considered an oncofetal antigen, because its mRNA and protein expression is increased in, including without limitation, hepatocellular carcinomas ("HOC") (Sung, Y. K., S. Y. Hwang, M. K. Park, M. Farooq, I. S. Han, H. I. Bae, J. C. Kim, and M. Kim. 2003. Glypican-3 is overexpressed in human hepatocellular carcinoma. Cancer Sci 94:259; Hsu, H. C, W. Cheng, and P. L. Lai. 1997. Cloning and expression of a developmentally regulated transcript MXR7 in hepatocellular carcinoma: biological significance and temporospatial distribution. Cancer Res 57:5179; Zhu, Z. W., H. Friess, L. Wang, M. Abou-Shady, A. Zimmermann, A. D. Lander, M. Korc, J. Kleeff, and M. W. Buchler. 2001. Enhanced glypican-3 expression differentiates the majority of hepatocellular carcinomas from benign hepatic disorders. Gut 48:558.), colorectal malignancies (Lage, H., M. Dietel, G. Froschle, and A. Reymann. 1998. Expression of the novel mitoxantrone resistance associated gene MXR7 in colorectal malignancies, Int J CHn Pharmacol Ther 36:58.), prostate cancer cells (WO07/081790), embryonal tumors (Saikali, Z., and D. Sinnett. 2000. Expression of glypican 3 (GPC3) in embryonal tumors, Int J Cancer 89:418.), melanoma and melanocyte nevus (Nakatsura, T. F T. Kageshita, S. Ito, K. Wakamatsu, M. Monji, Y. Ikuta, S. Senju, T. Ono, and Y. Nishimura. 2004. Identification of glypican-3 as a novel tumor marker for melanoma. Clin Cancer Res 10:6612.), Wilm's tumor, hepatoblastoma (Jakubovic and Jothy; Ex. Mol. Path. 82:184-189 (2007); Nakatsura and Nishimura, Biodrugs 19(2):71-77 (2005)), lung squamous cell carcinoma, neuroblastoma and testicular germ-cell tumors, as compared to normal tissue where GPC-3 is usually down-regulated or silenced.

It would still be desirable, therefore, to have alternative lipocalin muteins that are capable of binding GPC3 but are derived from a different wild type lipocalin (SWISS-PROT Data Bank Accession Number P31025), human tear lipocalin (TLPC or Tlc, also termed lipocalin-1, tear pre-albumin or von Ebner gland protein), and can be used in pharmaceutical and/or diagnostic applications. Accordingly, it is an object of the present disclosure to provide such tear lipocalin muteins. No such tear lipocalin muteins having these features attendant to the uses provided by present disclosure have been previously described.

Based on the discovery of GPC-3-binding hNGAL muteins that can be internalized from GPC-3-expressing cells' surface, and therefore, are capable of delivering one or more therapeutic moieties or one or more detectable labels to cancer cells expressing GPC-3, the present disclosure provides a promising way, using such hNGAL muteins, for targeted delivery one or more therapeutic moieties or one or more detectable labels to cancer cells expressing GPC-3, hereby enhancing the antitumor activity of the therapeutic moieties and reducing the systemic toxicity of the therapeutic moieties and detectable labels. No such uses of hNGAL muteins having these features attendant to the uses provided by present disclosure have been previously described.

The recitation of any reference in this application is not an admission that the reference is prior art to this application.

DETAILED DESCRIPTION OF THE DISCLOSURE

Figure 1:
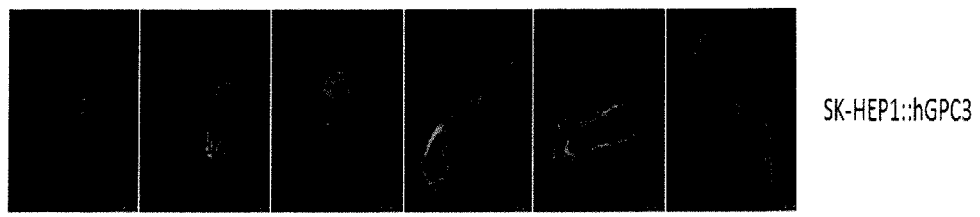
FIG. 1 shows the cell surface binding of GPC-3 specific hNGAL muteins (SEQ ID NOs: 2-6) to SKV-Hep1:hGPC-3 expressing cells by confocal microscopy. hNGAL muteins were detected using a Phycoerythrin (PE) labeled antibody (The presence of GPC-3 on the surface of the cells was also confirmed by confocal imaging together with lack of mutein binding to control cell line SK-Hep1:EV).

A. Lipocalin Muteins with Binding-Affinity for Glypican-3 (GPC-3)

In one aspect, the present disclosure relates to novel, specific-binding human tear lipocalin muteins directed against or specific for Glypican-3 (GPC-3). Human tear lipocalin muteins disclosed herein may be used for therapeutic and/or diagnostic purposes. A human tear lipocalin mutein of the disclosure may also be designated herein as "a Tlc mutein". As used herein, a Tlc mutein of the disclosure "specifically binds" a target (here, GPC-3) if it is able to discriminate between that target and one or more reference targets, since binding specificity is not an absolute, but a relative property. "Specific binding" can be determined, for example, in accordance with Western blots, ELISA-, RIA-, ECL-, IRMA-tests, FACS, IHC and peptide scans.

In this regard, the disclosure provides one or more Tlc muteins that are capable of binding Glypican-3 (GPC-3) with an affinity measured by a KD of about 10 nM or lower. More preferably, the Tlc muteins can have an affinity measured by a KD of about 1 nM or 0.3 nM or lower. In another embodiment, the Tlc muteins are capable of competing for binding to GPC-3 in a competition assay preferably with an IC50 value of about 1 nM, 0.6 nM or 0.2 nM or lower.

A lipocalin is a polypeptide defined by its supersecondary structure, namely cylindrical β-pleated sheet supersecondary structural region comprising eight β-strands connected pair-wise by four loops at one end to define thereby a binding pocket. In this regard, the disclosure relates to a lipocalin mutein having a cylindrical β-pleated sheet supersecondary structural region comprising eight β-strands connected pair-wise by four loops at one end to define thereby a binding pocket, wherein at least one amino acid of each of at least three of said four loops has been mutated and wherein said lipocalin muetein is effective to bind GPC-3 with detectable affinity. In some particular embodiments, said lipocalin mutein is derived from tear lipocalin or hNGAL. In some other particular embodiments, said lipocalin mutein is derived from lipocalin other than tear lipocalin or hNGAL.

In some embodiments, a lipocalin mutein binding GPC-3 with detectable affinity may include at least one amino acid substitution of a native cysteine residue by a serine residue. In some other embodiments, a lipocalin mutein binding GPC-3 with detectable affinity may include one or more non-native cystein residues substituting one or more amino acids of a wild type lipocalin. In a further particular embodiment, a lipocalin mutein according to the disclosure includes at least two amino acid substitutions of a native amino acid by a cysteine residue, hereby to form one or more cysteine briges. In some embodiment, said cysteine briges connect at least two loop regions. The definition of these regions is used herein in accordance with Flower (Flower, 1996, supra, Flower, et al., 2000, supra) and Breustedt et al. (2005, supra).

In some embodiments, a Tlc mutein of the disclosure includes at least two amino acid substitutions, which are located at one or more sequence positions of the positions 26-34, 55-61, 64, 79, 101, 104-106, 108, 111, 114 and 153 of the linear polypeptide sequence of the mature human tear lipocalin.

In further particular embodiments, the Tlc muteins of the disclosure may further comprise a mutated amino acid residue at one or more positions corresponding to position 26-34, 55-61, 64, 104-106 and 108 of the linear polypeptide sequence of the mature human tear lipocalin (SWISS-PROT Data Bank Accession Number P31025).

In further particular embodiments, the Tlc muteins of the disclosure may further include a mutated amino acid residue at one or more positions corresponding to positions 79, 101, 111, 114 and 153 of the linear polypeptide sequence of the mature human tear lipocalin.

In particular embodiments, the Tlc muteins of the disclosure comprise at least 1, 2, 3, 4, 5, 6, 7, 8, 9, 10, 11, 12, 13, 14, 15, 16, 17, 18, 19, 20 or 21, sometimes even more, mutated amino acid residues at one or more sequence positions corresponding to sequence positions 26, 27, 28, 30, 31, 32, 33, 34, 55, 56, 57, 58, 60, 61, 64, 79, 101, 104, 105, 106, 108, 111, 114 and 153 of the linear polypeptide sequence of the mature human tear lipocalin.

Similarly, the disclosure relates to a polypeptide comprising tear lipocalin shown in SEQ ID NO: 9, wherein said tear lipocalin comprises at least 2, 3, 4, 5, 6, 7, 8, 9, 10, 11, 12, 13, 14, 15, 16, 17, 18, 19, 20 or 21, sometimes even more, mutated amino acid residues at the sequence positions 26, 27, 28, 30, 31, 32, 33, 34, 55, 56, 57, 58, 60, 61, 64, 79, 101, 104, 105, 106, 108, 111, 114 and/or 153. Said polypeptide is preferably a lipocalin mutein.

In further particular embodiments, a Tlc mutein according to the current disclosure comprises an amino acid sequence selected from the group consisting of SEQ ID NOs: 7-8. In another embodiment, the mutein has at least 70% identity or at least 70% sequence homology to the sequence of a wild-type human lipocalin, including the human tear lipocalin. Preferably, said mutein comprises at least 2, 3, 4, 5, 6, 7, 8, 9, 10, 11, 12, 13, 14, 15, 16, 17, 18, 19, 20 or 21, sometimes even more, mutated amino acid residues at the sequence positions 26, 27, 28, 30, 31, 32, 33, 34, 55, 56, 57, 58, 60, 61, 64, 79, 101, 104, 105, 106, 108, 111, 114 and/or 153 of the linear polypeptide sequence of tear lipocalin (SEQ ID NO: 9). In further particular embodiments, a Tlc mutein according to the current disclosure comprises an amino acid sequence selected from the group consisting of the Tlc muteins disclosed in FIG. 5 (SEQ ID NOs: 11-43).

In another embodiment, the Tlc muteins of the current disclosure are fused at its N-terminus and/or its C-terminus to a fusion partner which is a protein domain that extends the serum half-life of the mutein. In further particular embodiments, the protein domain is a Fc part of an immunoglobulin, a CH3 domain of an immunoglobulin, a CH4 domain of an immunoglobulin, an albumin binding peptide, or an albumin binding protein.

In another embodiment, the Tlc muteins are conjugated to a compound that extends the serum half-life of the mutein. More preferably, the mutein is conjugated to a compound selected from the group consisting of a polyalkylene glycol molecule, a hydroethylstarch, an Fc part of an immunoglobulin, a CH3 domain of an immuoglobulin, a CH4 domain of an immunoglobulin, an albumin binding peptide, and an albumin binding protein.

In another embodiment, the Tlc muteins of the current disclosure are an antagonist of a GPC-3.

In another embodiment, the current disclosure relates to a nucleic acid molecule comprising a nucleotide sequence encoding a Tlc mutein disclosed herein.

In yet another embodiment, the disclosure encompasses a host cell containing said nucleic acid molecule.

The amino acid sequence of a Tlc mutein disclosed herein has a high sequence identity to mature human tear lipocalin (SWISS-PROT Data Bank Accession Number P31025) when compared to sequence identities with other lipocalins. In this general context, the amino acid sequence of a Tlc mutein of the disclosure is at least substantially similar to the amino acid sequence of mature human tear lipocalin, with the proviso that possibly there are gaps (as defined below) in an alignment that are the result of additions or deletions of amino acids. A respective sequence of a mutein of the disclosure, being substantially similar to the sequences of mature human tear lipocalin, has, in some embodiments, at least 70% identity or sequence homology, at least 75% identity or sequence homology, at least 80% identity or sequence homology, at least 82% identity or sequence homology, at least 85% identity or sequence homology, at least 87% identity or sequence homology, or at least 90% identity or sequence homology including at least 95% identity or sequence homology, to the sequence of mature human tear lipocalin, with the proviso that the altered position or sequence is retained and that one or more gaps are possible.

By "identity" is meant a property of sequences that measures their similarity or relationship. The term "sequence identity" or "identity" as used in the present disclosure means the percentage of pair-wise identical residues—following (homologous) alignment of a sequence of a polypeptide of the disclosure (any lipocalin mutein of the disclosure, the wide-type human tear lipocalin or the wide-type human lipocalin 2) with a sequence in question—with respect to the number of residues in the longer of these two sequences. Identity is measured by dividing the number of identical residues by the total number of residues and multiplying the product by 100. The term "homology" is used herein in its usual meaning and includes identical amino acids as well as amino acids which are regarded to be conservative substitutions (for example, exchange of a glutamate residue by an aspartate residue) at equivalent positions in the linear amino acid sequence of a polypeptide of the disclosure (e.g. any lipocalin mutein of the disclosure, the wide-type human tear lipocalin or the wide-type human lipocalin 2).

As two illustrative examples, the mutein of the SEQ ID NO: 7 has an amino acid sequence identity or a sequence homology of approximately 83.5% with the amino acid sequence of mature human tear lipocalin, and the mutein of the SEQ ID NO: 8 has an amino acid sequence identity or a sequence homology of approximately 83% with mature human tear lipocalin.

"Gaps" are spaces in an alignment that are the result of additions or deletions of amino acids. Thus, two copies of exactly the same sequence have 100% identity, but sequences that are less highly conserved, and have deletions, additions, or replacements, may have a lower degree of identity. Those skilled in the art will recognize that several computer programs are available for determining sequence identity using standard parameters, for example Blast (Altschul, et al. (1997) Nucleic Acids Res. 25, 3389-3402), Blast2 (Altschul, et al. (1990) J. Mol. Biol. 215, 403-410), and Smith-Waterman (Smith, et al. (1981) J. Mol. Biol. 147, 195-197).

The term "mutated" or "mutant" in reference to a nucleic acid or a polypeptide refers to the substitution, deletion, or insertion of one or more nucleotides or amino acids, respectively, compared to the naturally occurring (wild-type) nucleic acid or polypeptide. A Tlc mutein of the disclosure includes at least two substitutions in comparison to the corresponding mature human tear lipocalin (SWISS-PROT Data Bank Accession Number P31025).

As used herein, "detectable affinity" means the ability to bind to a selected target with an affinity constant of generally at least about $10^{-5}$ M. Lower affinities are generally no longer measurable with common methods such as ELISA and therefore of secondary importance. For example, binding affinities of muteins according to the disclosure may in some embodiments be of a $K_D$ below 800 nM, in some embodiments be of a $K_D$ below 30 nM and in some embodiments about 50 picomolar (pM) or below.

In some embodiments, a Tlc mutein according to the disclosure includes an amino acid substitution of a native cysteine residue at positions 61 and/or 153 by a serine residue. In this context it is noted that it has been found that removal of the structural disulfide bond (on the level of a respective nave nucleic acid library) of wild type tear lipocalin that is formed by the cysteine residues 61 and 153 (cf. Breustedt, et al., 2005, supra) provides tear lipocalin muteins that are not only stably folded but in addition are also able to bind a given non-natural ligand with high affinity. Without wishing to be bound by theory, it is also believed that the elimination of the structural disulde bond provides the further advantage of allowing for the (spontaneous) generation or deliberate introduction of non-natural artificial disulfide bonds into muteins of the disclosure, thereby increasing the stability of the muteins. For example, in some embodiments, a Tlc mutein according to the disclosure includes an amino acid substitution of a native cysteine residue at position 101 by a serine residue. Further, in some embodiments, a mutein according to the disclosure includes an amino acid substitution of a native arginine residue at positions 111 by a proline residue. In some embodiments a mutein according to the disclosure includes an amino acid substitution of a native lysine residue at positions 114 by a tryptophan residue.

A Tlc mutein according to the disclosure may further include, with respect to the amino acid sequence of the mature human tear lipocalin (SWISS-PROT Data Bank Accession Number P31025), one or more, including at least two, at least three, at least four, at least five, at least six, at least seven, at least eight, at least nine, at least ten, at least eleven, at least twelve, at least thirteen or at least fourteen amino acid substitutions of native amino acid residues by cysteine residues at any of positions 26-34, 55-61, 64, 79, 101, 104-106, 108, 111, 114 and 153 of the mature human tear lipocalin.

In some embodiments, a mutein according to the disclosure includes an amino acid substitution of a native amino acid by a cysteine residue at positions 28 or 105 with respect to the amino acid sequence of mature human tear lipocalin. In some embodiments a mutein according to the disclosure includes an amino acid substitution of a native amino acid by a cysteine residue at positions 28 or 105 with respect to the amino acid sequence of mature human tear lipocalin. In a further particular embodiment, a mutein according to the disclosure includes an amino acid substitution of a native amino acid by two cysteine residue at positions 28 and 105 with respect to the amino acid sequence of mature human tear lipocalin.

In some embodiments, a Tlc mutein according to the disclosure includes a substituted amino acid of at least one or of both of the cysteine residues occurring at each of the sequences positions 61 and 153 by another amino acid and the mutation of at least three amino acid residue at any one of the sequence positions 26-34, 55-61, 64, 79, 101, 104-106, 108, 111, 114 and 153 of the linear polypeptide sequence of the mature human tear lipocalin (SWISS-PROT Data Bank Accession Number P31025). The positions 26-28 and 30-34 are included in the AB loop, the position 55 is located at the very end of a beta-sheet and following positions 56-58 are included in the CD loop. The positions 104-106 and 108 are included in the GH loop in the binding site at the open end of the β-barrel structure of the mature human tear lipocalin. The definition of these regions is used herein in accordance with Flower (Flower, 1996, supra, Flower, et al., 2000, supra) and Breustedt et al. (2005, supra). In some embodiments, the Tlc mutein according to the disclosure includes the amino acid substitutions Cys 61→Ala, Phe, Lys, Arg, Thr, Asn, Gly, Gln, Asp, Asn, Leu, Tyr, Met, Ser, Pro or Trp and Cys 153→Ser or Ala. Such a substitution has proven useful to prevent the formation of the naturally occurring disulphide bridge linking Cys 61 and Cys 153, and thus to facilitate handling of the mutein. However, tear lipocalin muteins that binds GPC-3 and that have the disulphide bridge formed between Cys 61 and Cys 153 are also part of the present disclosure In some embodiments, the Tlc mutein according to the disclosure includes at least one amino acid substitution, which may be an additional amino acid substitution, selected from Arg 111→Pro and Lys 114→Trp. A Tlc mutein of the disclosure may further include the cysteine at position 101 of the sequence of the mature human tear lipocalin substituted by another amino acid. This substitution may, for example, be the mutation Cys 101→Ser or Cys 101→Thr.

As defined above, a Tlc mutein of the disclosure includes at least two amino acid substitutions, which are located at one or more sequence positions of the positions 26-34, 55-61, 64, 79, 101, 104-106, 108, 111, 114 and 153 of the linear polypeptide sequence of the mature human tear lipocalin. In some embodiments, a mutein of the disclosure includes two or more, such as 3, 4, 5, 6, 7, 8, 9, 10, 11, 12, 13, 14, 16, 18, 19, 20 or 21 amino acid substitutions of these sequence positions of the mature human tear lipocalin. In one embodiment, the Tlc mutein has a mutated amino acid residue at each of the sequence positions 26-34, 55-61, 64, 79, 101, 104-106, 108, 111, 114 and 153 of the linear polypeptide sequence of the mature human tear lipocalin.

In some embodiments, the mutated amino acid residues at any one or more of the sequence positions 26-34, 55-61, 64, 79, 101, 104-106, 108, 111, 114 and 153 of the linear polypeptide sequence of the mature human tear lipocalin include one or more of the following substitutions: Arg 26→Asp, Thr, Ser, Gly, Phe, Tyr, Val or Glu, Pro 29→Arg, Lys, Ser, Glu, Leu or Phe, Asn 32→Tyr, Trp, Gln, His, Leu, Lys, Phe or Arg, Glu 34→Gly, Asn, Pro, Trp, Arg or His, Leu 56→Pro, Ser, Phe, Trp, Arg, Asn, Ala, Val, Asp, Gln, Glu or Thr, Ser 58→Asp, Trp, Phe, Ala, Glu, His, Asn, Pro or Val, Cys 61→Arg, Ser, Gly, Ala, Trp, Lys, Tyr, Asp, Thr, Val, Ile, Thr, Phe, Asn, Leu, Gln or Glu, Glu 104→Trp, Thr, Ser, Ile, Ala or Asp and His 106→Ala, Tyr, Phe, Pro, Thr or Glu. In some embodiments, a Tlc mutein of the disclosure includes two or more, such as 3, 4, 5, 6, 7, 8 or all amino acid substitutions of these sequence positions of the mature human tear lipocalin.

In some embodiments, a Tlc mutein according to the disclosure includes at least one of the following substitutions: Glu 27→Thr, Asn, Asp, Arg, Leu, Phe or Val, Glu 30→Gly, Lys, Phe, Trp or Asn, Met 31→Ala, His, Leu, Trp, Gly, Ser or Arg, Leu 33→Gln, His, Gly, Val, Glu or Phe, Met 55→Gln, Asn, Ile, Thr, Ser or Leu, Ile 57→Leu or Ser, Arg 60→Tyr, Asp, Thr, Trp, Ile, Pro, Glu, Gln, Val, Ser, Gly or Arg, and Lys 108→Leu, Ser, Phe or Trp. In some embodiments, a Tlc mutein according to the disclosure includes two or more, such as 3, 4, 5, 6, 7 or all of the substitutions amino acid substitutions of these sequence positions of the mature human tear lipocalin.

In some embodiments, a Tlc mutein according to the disclosure includes one of the substitutions selected from the group consisting Val 64→Trp, Val 64→Leu, Val 64→Asp or Val 64→Ala.

Additionally, a Tlc mutein according to the disclosure may further include an amino acid substitution Arg 111→Pro. A Tlc mutein according to the disclosure may also include a substitution Lys 114→Trp. It may also comprise a substitution Cys 101→Ser or Cys 101→Thr. In some preferred embodiments, a Tlc mutein according to the disclosure may also comprise a substitution Cys 153→Ser.

In some embodiments, the Tlc mutein binding GPC-3 includes at least one, including 2, 3, 4, 5 or 6 of the following the amino acid substitutions: Arg 26→Thr; Glu 27→Leu; Phe 28→Cys; Pro 29→Phe; Glu 30→Gly; Leu 33→Glu; Met 55→Asn; Ile 57→Leu; Ala 79→Val; Cys 101→Ser; Glu 104→Asp; Leu 105→Cys; Arg 111→Pro; Lys 114→Trp and Cys 153→Ser.

In some embodiments, the Tlc mutein binding GPC-3 includes with respect to the amino acid sequence of mature human tear lipocalin at least 7, 8, 9, 10, 11, 13 or 14 amino acid substitutions selected from the group consisting of Arg 26→Thr; Glu 27→Leu; Phe 28→Cys; Pro 29→Phe; Glu 30→Gly; Leu 33→Glu; Met 55→Asn; Ile 57→Leu; Ala 79→Val; Cys 101→Ser; Glu 104→Asp; Leu 105→Cys; Arg 111→Pro; Lys 114→Trp and Cys 153→Ser. In some embodiments, the Tlc mutein includes all of these amino acid substitutions.

Additionally, such a Tlc mutein further comprising one of the following sets of amino acid substitutions:
(1) Met 31→Ala, Asn 32→Arg, Glu 34→His, Leu 56→Trp, Ser 58→Asn, Arg 60→Trp; Cys 61→Arg; His 106→Glu; and Lys 108→Trp; or
(2) Met 31→Arg, Asn 32→Phe, Glu 34→Gly, Leu 56→Thr, Ser 58→Asp, Arg 60→Glu; Cys 61→Tyr; His 106→Ala; and Lys 108→Leu.

In some embodiments the Tlc mutein binding GPC-3 includes one of the following sets of amino acid substitutions:
1. Arg 26→Thr; Glu 27→Leu; Phe 28→Cys; Met 31→Ala; Glu 34→Gly; Leu 56→Thr; Cys 61→Tyr; Ala 79→Val; Cys 101→Ser; Leu 105→Cys; His 106→Ala; Arg 111→Pro; Lys 114→Trp; Cys 153→Ser;
2. Arg 26→Thr; Glu 27→Leu; Phe 28→Cys; Asn 32→Phe; Leu 33→Glu; Met 55→Asn; Cys 61→Tyr; Ala 79→Val; Cys 101→Ser; Leu 105→Cys; Lys 108→Leu; Arg 111→Pro; Lys 114→Trp; Cys 153→Ser;
3. Arg 26→Thr; Glu 27→Leu; Phe 28→Cys; Glu 30→Gly; Leu 33→Glu; Glu 34→Gly; Leu 56→Thr;

Ser 58→Asp; Cys 101→Ser; His 106→Ala; Lys 108→Leu; Arg 111→Pro; Lys 114→Trp; Cys 153→Ser;
4. Arg 26→Thr; Phe 28→Cys; Glu 29→Arg; Asn 32→Tyr; Leu 56→Trp; Ile 57→Leu; Arg 60→Trp; Cys 61→Arg; Cys 101→Ser; Leu 105→Cys; Lys 108→Trp; Arg 111→Pro; Lys 114→Trp; Cys 153→Ser;
5. Arg 26→Thr; Phe 28→Cys; Met 31→Ala; Asn 32→Tyr; Glu 34→His; Leu 56→Trp; Ser 58→Asn; Arg 60→Trp; Cys 101→Ser; Leu 105→Cys; His 106→Glu; Arg 111→Pro; Lys 114→Trp; Cys 153→Ser; or
6. Arg 26→Thr; Phe 28→Cys; Glu 29→Arg; Met 31→Ala; Leu 33→His; Ile 57→Leu; Ser 58→Asn; Cys 61→Arg; Cys 101→Ser; Glu 104→Asp; Lys 108→Trp; Arg 111→Pro; Lys 114→Trp; Cys 153→Ser.

In the residual region, i.e. the region differing from sequence positions 26-34, 55-61, 64, 79, 101, 104-106, 108, 111, 114 and 153, a Tlc mutein of the disclosure may include the wild type (natural) amino acid sequence outside the mutated amino acid sequence positions. In some embodiments a lipocalin mutein according to the disclosure may also carry one or more amino acid mutations at a sequence position/positions as long as such a mutation does, at least essentially not hamper or not interfere with the binding activity and the folding of the mutein. Such mutations can be accomplished very easily on DNA level using established standard methods. Illustrative examples of alterations of the amino acid sequence are insertions or deletions as well as amino acid substitutions. Such substitutions may be conservative, i.e. an amino acid residue is replaced with an amino acid residue of chemically similar properties, in particular with regard to polarity as well as size. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan. On the other hand, it is also possible to introduce non-conservative alterations in the amino acid sequence. In addition, instead of replacing single amino acid residues, it is also possible to either insert or delete one or more continuous amino acids of the primary structure of the human tear lipocalin as long as these deletions or insertion result in a stable folded/functional mutein (for example, Tlc muteins with truncated N- and C-terminus). In such mutein, for instance, one or more amino acid residues are added or deleted at the N- or C-terminus of the polypeptide. Generally such a mutein may have about at least 70%, including at least about 80%, such as at least about 85% amino acid sequence identity, with the amino acid sequence of the mature human tear lipocalin. As an illustrative example, the first 4 N-terminal amino acid residues (His, His, Leu, Ala) and the last 2 C-terminal amino acid residues (Ser, Asp) can be deleted in a tear lipocalin mutein of the disclosure without affecting the biological function of the protein, e.g. SEQ ID NO: 7 or SEQ ID NO: 8.

Such modifications of the amino acid sequence include directed mutagenesis of single amino acid positions in order to simplify sub-cloning of the mutated lipocalin gene or its parts by incorporating cleavage sites for certain restriction enzymes. In addition, these mutations can also be incorporated to further improve the affinity of a Tlc mutein for GPC-3. Furthermore, mutations can be introduced in order to modulate certain characteristics of the mutein such as to improve folding stability, serum stability, protein resistance or water solubility or to reduce aggregation tendency, if necessary. For example, naturally occurring cysteine residues may be mutated to other amino acids to prevent disulphide bridge formation. Exemplary possibilities of such a mutation to introduce a cysteine residue into the amino acid sequence of a Tlc mutein include the substitutions Thr 40→Cys, Glu 73→Cys, Arg 90→Cys, Asp 95→Cys, and Glu 131→Cys. The generated thiol moiety at the side of any of the amino acid positions 40, 73, 90, 95 and/or 131 may be used to PEGylate or HESylate the mutein, for example, in order to increase the serum half-life of a respective Tlc mutein.

Figure 5:
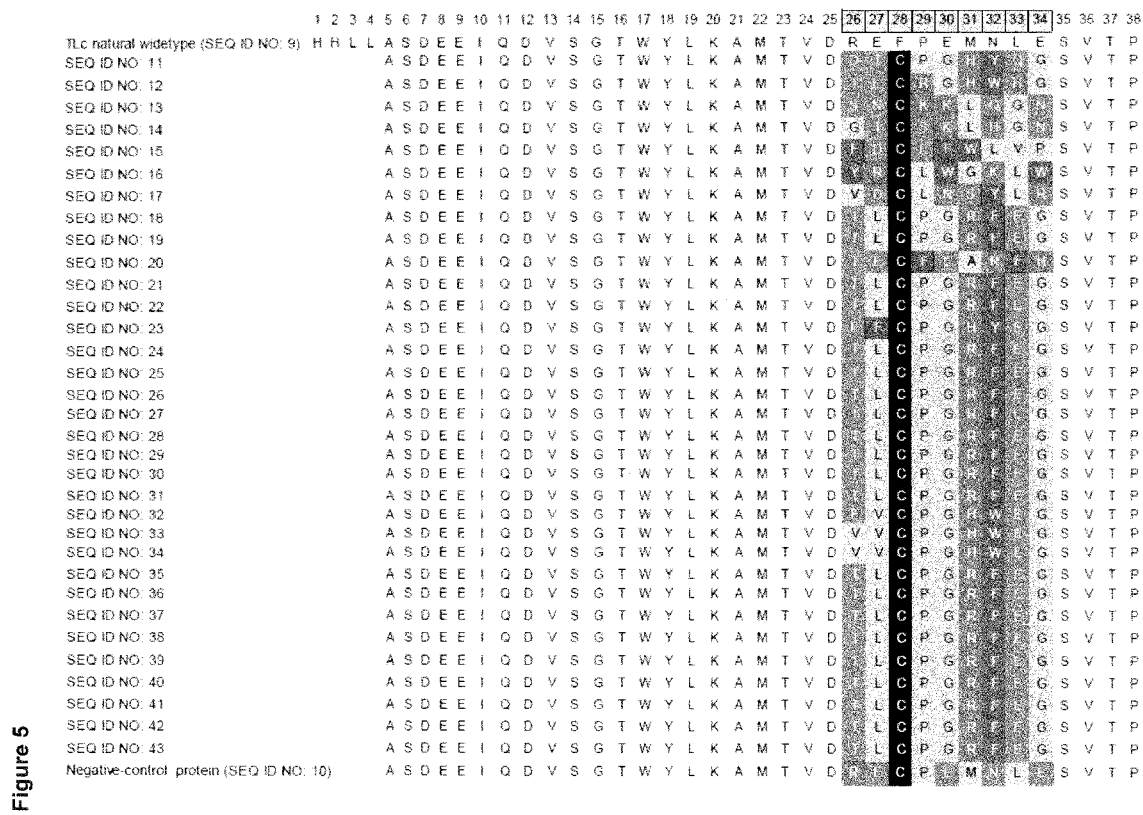
FIG. 5 depicts an alignment of amino acid sequences of certain GPC-3 specific, human-tear-lipocalin-based muteins in comparison with the polypeptide sequence of the mature human tear lipocalin ("Tlc"). Compared to the linear polypeptide sequence of the mature human tear lipocalin (SEQ ID NO: 9), the first 4 N-terminal amino acid residues (His, His, Leu, Ala) and the last 2 C-terminal amino acid residues (Ser, Asp) are deleted in these Tlc-derived, GPC-3-binding muteins (listed as Tlc muteins NOs: 1-33 in FIG. 5; SEQ ID NOs: 11-43) and the negative-control protein (SEQ ID NO: 10). Residues at positions 157 to 166 of the alignment are the sequence of a streptavidin binding tag, Strep-Tag™, used in the isolation of these muteins.

The present disclosure also encompasses Tlc muteins as defined above, in which the first four N-terminal amino acid residues of the sequence of mature human tear lipocalin (His-His-Leu-Leu; positions 1-4 (SEQ ID NO: 56)) and/or the last two C-terminal amino acid residues (Ser-Asp; positions 157-158) of the linear polypeptide sequence of the mature human tear lipocalin (SWISS-PROT Data Bank Accession Number P31025) have been deleted (FIG. 5, Example 4, SEQ ID NO: 7 and SEQ ID NO: 8). Another possible mutation of the wild type polypeptide sequence of the mature human tear lipocalin is to change the amino acid sequence at sequence positions 5 to 7 (Ala Ser Asp) to Gly Gly Asp as described in PCT application WO 2005/019256.

The Tlc muteins of the disclosure may include, consist essentially of or consist of any one of the amino acid sequences set forth in SEQ ID NOs: 7-8 or a fragment or variant thereof. In addition, the human tear lipocalin mutein of the disclosure may include, consist essentially of or consist of the Tlc muteins disclosed in FIG. 5 (SEQ ID NOs: 11-43) or a fragment or variant thereof.

The term "fragment" as used herein in connection with the muteins of the disclosure relates to proteins or peptides derived from full-length mature human tear lipocalin that are N-terminally and/or C-terminally shortened, i.e. lacking at least one of the N-terminal and/or C-terminal amino acids. Such fragments may include at least 10, more such as 20 or 30 or more consecutive amino acids of the primary sequence of the mature human tear lipocalin and are usually detectable in an immunoassay of the mature human tear lipocalin.

The term "variant" as used in the present disclosure relates to derivatives of a protein or peptide that include modifications of the amino acid sequence, for example by substitution, deletion, insertion or chemical modification. Such modifications do in some embodiments not reduce the functionality of the protein or peptide. Such variants include proteins, wherein one or more amino acids have been replaced by their respective D-stereoisomers or by amino acids other than the naturally occurring 20 amino acids, such as, for example, ornithine, hydroxyproline, citrulline, homoserine, hydroxylysine, norvaline. However, such substitutions may also be conservative, i.e. an amino acid residue is replaced with a chemically similar amino acid residue. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan.

Such a Tlc mutein may include with respect to the amino acid sequence of mature human tear lipocalin at least 6, 8, 10, 12, 14 or 16 amino acid substitutions selected from the group consisting of Arg 26→Ser; Glu 27→Ile; Glu 30→Ser; Met 31→Gly; Asn 32→Arg; Leu 33→Ile; Glu 34→Tyr; Leu 56→Lys, Glu, Ala, Met; Ile 57→Phe; Ser 58→Arg; Glu 104→Leu; Leu 105→Ala; His 106→Val and Lys 108→Thr and may further include at least one amino acid substitution selected from the group consisting of Ala 79→Val; Cys 101 Ser; Arg 111→Pro; Lys 114→Trp; and Cys 153→Ser.

In one specific embodiment, such Tlc mutein includes the amino acid substitutions: Arg 26→Ser, Glu 27→Ile, Glu 30→Ser, Met 31→Gly, Asn 32→Arg, Leu 33→Ile, Glu 34→Tyr, Ile 57→Phe, Ser 58→Arg, Glu 104→Leu, Leu 105→Ala, His 106→Val and Lys 108→Thr.

A Tlc mutein according to the present disclosure can be obtained by means of mutagenesis of a naturally occurring form of human tear lipocalin.

The term "mutagenesis" as used herein means that the experimental conditions are chosen such that the amino acid naturally occurring at a given sequence position of the mature human tear lipocalin (Swiss-Prot data bank entry P31025) can be substituted by at least one amino acid that is not present at this specific position in the respective natural polypeptide sequence. The term "mutagenesis" also includes the (additional) modification of the length of sequence segments by deletion or insertion of one or more amino acids. Thus, it is within the scope of the disclosure that, for example, one amino acid at a chosen sequence position is replaced by a stretch of three random mutations, leading to an insertion of two amino acid residues compared to the length of the respective segment of the wild type protein. Such an insertion of deletion may be introduced independently from each other in any of the peptide segments that can be subjected to mutagenesis in the disclosure. In one exemplary embodiment of the disclosure, an insertion of several mutations may be introduced into the loop AB of the chosen lipocalin scaffold (cf. International Patent Application WO 2005/019256 which is incorporated by reference its entirety herein).

The term "random mutagenesis" means that no predetermined single amino acid (mutation) is present at a certain sequence position but that at least two amino acids can be incorporated with a certain probability at a predefined sequence position during mutagenesis.

The term "position" when used in accordance with the disclosure means the position of either an amino acid within an amino acid sequence depicted herein or the position of a nucleotide within a nucleic acid sequence depicted herein. The term "corresponding" as used herein also includes that a position is not only determined by the number of the preceding nucleotides/amino acids. Accordingly, the position of a given amino acid in accordance with the disclosure which may be substituted may very due to deletion or addition of amino acids elsewhere in a (mutant or wild-type) lipocalin. Similarly, the position of a given nucleotide in accordance with the present disclosure which may be substituted may vary due to deletions or additional nucleotides elsewhere in a mutein or wild type lipocalin 5'-untranslated region (UTR) including the promoter and/or any other regulatory sequences or gene (including exons and introns).

Thus, under a "corresponding position" in accordance with the disclosure it is preferably to be understood that nucleotides/amino acids may differ in the indicated number but may still have similar neighbouring nucleotides/amino acids. Said nucleotides/amino acids, which may be exchanged, deleted, or added, are also comprised by the term "corresponding position."

Specifically, in order to determine whether an amino acid residue of the amino acid sequence of a lipocalin (mutein) different from a wild-type lipocalin corresponds to a certain position in the amino acid sequence of a wild-type lipocalin, a skilled artisan can use means and methods well-known in the art, e.g., alignments, either manually or by using computer programs such as BLAST2.0, which stands for Basic Local Alignment Search Tool or ClustalW or any other suitable program which is suitable to generate sequence alignments. Accordingly, a wild-type lipocalin can serve as "subject sequence" or "reference sequence", while the amino acid sequence of a lipocalin different from the wild-type lipocalin described herein serves as "query sequence". The terms "reference sequence" and "wild type sequence" are used interchangeably herein.

The coding sequence of human tear lipocalin (Redl, B. et al. (1992) *J. Biol. Chem.* 267, 20282-20287) is used as a starting point for the mutagenesis of the peptide segments selected in the present disclosure. For the mutagenesis of the recited amino acid positions, the person skilled in the art has at his disposal the various established standard methods for site-directed mutagenesis. A commonly used technique is the introduction of mutations by means of PCR (polymerase chain reaction) using mixtures of synthetic oligonucleotides, which bear a degenerate base composition at the desired sequence positions. For example, use of the codon NNK or NNS (wherein N=adenine, guanine or cytosine or thymine; K=guanine or thymine; S=adenine or cytosine) allows incorporation of all 20 amino acids plus the amber stop codon during mutagenesis, whereas the codon VVS limits the number of possibly incorporated amino acids to 12, since it excludes the amino acids Cys, Ile, Leu, Met, Phe, Trp, Tyr, Val from being incorporated into the selected position of the polypeptide sequence; use of the codon NMS (wherein M=adenine or cytosine), for example, restricts the number of possible amino acids to 11 at a selected sequence position since it excludes the amino acids Arg, Cys, Gly, Ile, Leu, Met, Phe, Trp, Val from being incorporated at a selected sequence position. In this respect it is noted that codons for other amino acids (than the regular 20 naturally occurring amino acids) such as selenocystein or pyrrolysine can also be incorporated into a nucleic acid of a mutein. It is also possible, as described by Wang, L., et al. (2001) *Science* 292, 498-500, or Wang, L., and Schultz, P. G. (2002) *Chem. Comm.* 1, 1-11, to use "artificial" codons such as UAG which are usually recognized as stop codons in order to insert other unusual amino acids, for example o-methyl-L-tyrosine or p-aminophenylalanine.

The use of nucleotide building blocks with reduced base pair specificity, as for example inosine, 8-oxo-2'deoxyguanosine or 6(2-deoxy-□-D-ribofuranosyl)-3,4-dihydro-8H-pyrimindo-1,2-oxazine-7-one (Zaccolo et al. (1996) *J. Mol. Biol.* 255, 589-603), is another option for the introduction of mutations into a chosen sequence segment.

A further possibility is the so-called triplet-mutagenesis. This method uses mixtures of different nucleotide triplets, each of which codes for one amino acid, for incorporation into the coding sequence (Virnekäs B, et al., 1994 *Nucleic Acids Res* 22, 5600-5607).

One possible strategy for introducing mutations in the selected regions of the respective polypeptides is based on the use of four oligonucleotides, each of which is partially derived from one of the corresponding sequence segments to be mutated. When synthesizing these oligonucleotides, a person skilled in the art can employ mixtures of nucleic acid building blocks for the synthesis of those nucleotide triplets which correspond to the amino acid positions to be mutated so that codons encoding all natural amino acids randomly arise, which at last results in the generation of a lipocalin peptide library. For example, the first oligonucleotide corresponds in its sequence—apart from the mutated positions—to the coding strand for the peptide segment to be mutated at the most N-terminal position of the lipocalin polypeptide. Accordingly, the second oligonucleotide corresponds to the non-coding strand for the second sequence segment following in the polypeptide sequence. The third oligonucleotide corresponds in turn to the coding strand for the corresponding third sequence segment. Finally, the fourth oligonucleotide corresponds to the non-coding strand for the fourth sequence segment. A polymerase chain reaction can be performed with the respective first and second oligonucleotide and separately, if necessary, with the respective third and fourth oligonucleotide.

The amplification products of both of these reactions can be combined by various known methods into a single nucleic acid that includes the sequence from the first to the fourth sequence segments, in which mutations have been introduced at the selected positions. To this end, both of the products can for example be subjected to a new polymerase chain reaction using flanking oligonucleotides as well as one or more mediator nucleic acid molecules, which contribute the sequence between the second and the third sequence segment. In the choice of the number and arrangement within the sequence of the oligonucleotides used for the mutagenesis, the person skilled in the art has numerous alternatives at his disposal.

The nucleic acid molecules defined above can be connected by ligation with the missing 5'- and 3'-sequences of a nucleic acid encoding a lipocalin polypeptide and/or the vector, and can be cloned in a known host organism. A multitude of established procedures are available for ligation and cloning. For example, recognition sequences for restriction endonucleases also present in the sequence of the cloning vector can be engineered into the sequence of the synthetic oligonucleotides. Thus, after amplification of the respective PCR product and enzymatic cleavage the resulting fragment can be easily cloned using the corresponding recognition sequences.

Longer sequence segments within the gene coding for the protein selected for mutagenesis can also be subjected to random mutagenesis via known methods, for example by use of the polymerase chain reaction under conditions of increased error rate, by chemical mutagenesis or by using bacterial mutator strains. Such methods can also be used for further optimization of the target affinity or specificity of a lipocalin mutein. Mutations possibly occurring outside the segments of experimental mutagenesis are often tolerated or can even prove to be advantageous, for example if they contribute to an improved folding efficiency or folding stability of the lipocalin mutein.

In a method according to the disclosure a nucleic acid molecule encoding a human tear lipocalin is firstly subjected to mutagenesis at one or more of the amino acid sequence positions 26-34, 55-61, 64, 104-106 and 108 of the linear polypeptide sequence of the mature human tear lipocalin (SWISS-PROT Data Bank Accession Number P31025). Secondly the nucleic acid molecule encoding a human tear lipocalin is also subjected to mutagenesis at one or more of the amino acid sequence positions 79, 101, 111, 114 and 153 of the linear polypeptide sequence of the mature human tear lipocalin.

In one embodiment of the disclosure, the method for the generation of a mutein of human tear lipocalin includes mutating at least 2, 3, 4, 5, 6, 8, 10, 12, 14, 15, 16, or 17 of the codons of any of the amino acid sequence positions 26, 27, 28, 30, 31, 32, 33, 34, 55, 56, 57, 58, 60, 61, 64, 79, 101, 104, 105, 106, 108, 111, 114 and 153 of the linear polypeptide sequence of the mature human tear lipocalin. In one embodiment all 24 of the codons of amino acid sequence positions 26, 27, 28, 30, 31, 32, 33, 34, 55, 56, 57, 58, 60, 61, 64, 79, 101, 104, 105, 106, 108, 111, 114 and 153 of the linear polypeptide sequence of the mature human tear lipocalin are mutated.

In a further embodiment, the methods according to the disclosure include the mutation of both of the codons encoding cysteine at positions 61 and 153 in the linear polypeptide sequence of mature human tear lipocalin. In one embodiment position 61 is mutated to encode an alanine, phenylalanine, lysine, arginine, threonin, asparagine, tyrosine, methionine, serine, proline or a tryptophane residue, to name only a few possibilities. In embodiments where position 153 is mutated, an amino acid such as a serine or alanine can be introduced at position 153.

In another embodiment of the disclosure, the codons encoding amino acid sequence positions 111 and/or 114 of the linear polypeptide sequence of mature human tear lipocalin are mutated to encode for example a proline at position 111 and a tryptophane at position 114.

Another embodiment of the methods as described herein involves mutagenesis of the codon encoding the cysteine at position 101 of the linear polypeptide sequence of mature human tear lipocalin so that this codon encodes any other amino acid. In one embodiment the mutated codon encoding position 101 encodes a serine. Accordingly, in some embodiments either two or all three of the cystein codons at position 61, 101 and 153 are replaced by a codon of another amino acid.

In further particular embodiments, a Tlc mutein of the disclosure has an amino acid sequence as set forth in any one of SEQ ID NOs: 7-8 or of a fragment or variant thereof.

In further particular embodiments, a Tlc mutein of the disclosure has at least 75%, at least 80%, at least 85% or higher identity to an amino acid sequence selected from the group consisting of SEQ ID NOs: 7-8.

In further particular embodiments, a Tlc mutein of the disclosure has at least 75%, at least 80%, at least 85% or higher identity to an amino acid sequence of a Tlc mutein selected from the group consisting of the Tlc muteins disclosed in FIG. 5 (SEC) ID NOs: 11-43).

In some embodiments a substitution (or replacement) is a conservative substitution. Nevertheless, any substitution—including non-conservative substitution or one or more from the exemplary substitutions below—is envisaged as long as the lipocalin mutein retains its capability to bind to GPC-3, and/or it has an identity to the then substituted sequence in that it is at least 60%, such as at least 65%, at least 70%, at least 75%, at least 80%, at least 85% or higher identity to the amino acid sequence of the mature human tear lipocalin.

Conservative substitutions are generally the following substitutions, listed according to the amino acid to be mutated, each followed by one or more replacement(s) that can be taken to be conservative: Ala→Gly, Ser, Val; Arg→Lys; Asn→Gln, His; Asp→Glu; Cys→Ser; Gln→Asn; Glu→Asp; Gly→Ala; His→Arg, Asn, Gln; Ile→Leu, Val; Leu→Ile, Val; Lys→Arg, Gln, Glu; Met→Leu, Tyr, Ile; Phe→Met, Leu, Tyr; Ser→Thr; Thr→Ser; Trp→Tyr; Tyr→Trp, Phe; Val→Ile, Leu. Other substitutions are also permissible and can be determined empirically or in accord with other known conservative or non-conservative substitutions. As a further orientation, the following eight groups each contain amino acids that can typically be taken to define conservative substitutions for one another:

1) Alanine (Ala), Glycine (Gly);
2) Aspartic acid (Asp), Glutamic acid (Glu);
3) Asparagine (Asn), Glutamine (Gin);

4) Arginine (Arg), Lysine (Lys);
5) Isoleucine (Ile), Leucine (Leu), Methionine (Met), Valine (Val);
6) Phenylalanine (Phe), Tyrosine (Tyr), Tryptophan (Trp);
7) Serine (Ser), Threonine (Thr); and
8) Cysteine (Cys), Methionine (Met)

If such substitutions result in a change in biological activity, then more substantial changes, such as the following, or as further described below in reference to amino acid classes, may be introduced and the products screened for a desired characteristic. Examples of such more substantial changes are: Ala→Leu, Ile; Arg→Gln; Asn→Asp, Lys, Arg, His; Asp→Asn; Cys→Ala; Gln→Glu; Glu→Gln; His→Lys; Ile→Met, Ala, Phe; Leu→Ala, Met, Norleucine; Lys→Asn; Met→Phe; Phe→Val, Ile, Ala; Trp→Phe; Tyr→Thr, Ser; Val→Met, Phe, Ala.

Substantial modifications in the biological properties of the human tear lipocalin as disclosed herein are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, met, ala, val, leu, ile; (2) neutral hydrophilic: cys, ser, thr; (3) acidic: asp, glu; (4) basic: asn, gln, his, lys, arg; (5) residues that influence chain orientation: gly, pro; and (6) aromatic: trp, tyr, phe.

Non-conservative substitutions will entail exchanging a member of one of these classes for another class. Any cysteine residue not involved in maintaining the proper conformation of the human tear lipocalin also may be substituted, generally with serine, to improve the oxidative stability of the molecule and prevent aberrant crosslinking. Conversely, cysteine bond (s) may be added to the lipocalin to improve its stability.

Any mutation, including an insertion as discussed above, can be accomplished very easily on the nucleic acid, e.g. DNA level using established standard methods. Illustrative examples of alterations of the amino acid sequence are insertions or deletions as well as amino acid substitutions. Such substitutions may be conservative, i.e. an amino acid residue is replaced with an amino acid residue of chemically similar properties, in particular with regard to polarity as well as size. Examples of conservative substitutions are the replacements among the members of the following groups: 1) alanine, serine, and threonine; 2) aspartic acid and glutamic acid; 3) asparagine and glutamine; 4) arginine and lysine; 5) iso-leucine, leucine, methionine, and valine; and 6) phenylalanine, tyrosine, and tryptophan. On the other hand, it is also possible to introduce non-conservative alterations in the amino acid sequence. In addition, instead of replacing single amino acid residues, it is also possible to either insert or delete one or more continuous amino acids of the primary structure of tear lipocalin as long as these deletions or insertion result in a stable folded/functional mutein.

Modifications of the amino acid sequence of the human tear lipocalin as disclosed herein include directed mutagenesis of single amino acid positions in order to simplify sub-cloning of the mutated lipocalin gene or its parts by incorporating cleavage sites for certain restriction enzymes. In addition, these mutations can also be incorporated to further improve the affinity of a lipocalin mutein for a given target. Furthermore, mutations can be introduced in order to modulate certain characteristics of the mutein such as to improve folding stability, serum stability, protein resistance or water solubility or to reduce aggregation tendency, if necessary. For example, naturally occurring cysteine residues may be mutated to other amino acids to prevent disulphide bridge formation. It is also possible to deliberately mutate other amino acid sequence position to cysteine in order to introduce new reactive groups, for example for the conjugation to other compounds, such as polyethylene glycol (PEG), hydroxyethyl starch (HES), biotin, peptides or proteins, or for the formation of non-naturally occurring disulphide linkages. The generated thiol moiety may be used to PEGylate or HESylate the mutein, for example, in order to increase the serum half-life of a respective tear lipocalin mutein.

The skilled worker will appreciate methods useful to prepare Tlc muteins contemplated by the present disclosure but whose protein or nucleic acid sequences are not explicitly disclosed herein. As an overview, such modifications of the amino acid sequence include, e.g., directed mutagenesis of single amino acid positions in order to simplify sub-cloning of a mutated lipocalin gene or its parts by incorporating cleavage sites for certain restriction enzymes. In addition, these mutations can also be incorporated to further improve the affinity of a Tlc mutein for GPC-3. Furthermore, mutations can be introduced to modulate certain characteristics of the mutein such as to improve folding stability, serum stability, protein resistance or water solubility or to reduce aggregation tendency, if necessary. For example, naturally occurring cysteine residues may be mutated to other amino acids to prevent disulphide bridge formation.

Accordingly, the disclosure also includes functional fragments or variants of Tlc muteins disclosed herein, which have a threshold sequence identity or sequence homology to a reference Tlc mutein. By "identity" or "sequence identity" is meant a property of sequences that measures their similarity or relationship. The term "sequence identity" or "identity" as used in the present disclosure means the percentage of pair-wise identical residues—following (homologous) alignment of a sequence of a polypeptide of the disclosure (e.g. any lipocalin mutein of the disclosure, the wide-type human tear lipocalin or the wide-type human lipocalin 2) with a sequence in question—with respect to the number of residues in the longer of these two sequences. Percent identity is determined by dividing the number of identical residues by the total number of residues and multiplying the product by 100. The term "homology" is used herein in its usual meaning and includes identical amino acids as well as amino acids which are regarded to be conservative substitutions (for example, exchange of a glutamate residue by an aspartate residue) at equivalent positions in the linear amino acid sequence of a polypeptide of the disclosure (e.g., any lipocalin mutein of the disclosure, the wide-type human tear lipocalin or the wide-type human lipocalin 2).

The percentage of sequence homology or sequence identity can, for example, be determined herein using the program BLASTP, version blastp 2.2.5 (Nov. 16, 2002; cf. Altschul, S. F. et al. (1997) *Nucl. Acids Res.* 25, 3389-3402). In this embodiment the percentage of homology is based on the alignment of the entire polypeptide sequences (matrix: BLOSUM 62; gap costs: 11.1; cutoff value set to $10^{-3}$) including the propeptide sequences, preferably using the wild type protein scaffold as reference in a pairwise comparison. It is calculated as the percentage of numbers of "positives" (homologous amino acids) indicated as result in the BLASTP program output divided by the total number of amino acids selected by the program for the alignment.

According to the methods of the disclosure, a Tlc mutein is obtained starting from a nucleic acid encoding human tear lipocalin. Such a nucleic acid is subjected to mutagenesis and introduced into a suitable bacterial or eukaryotic host organism by means of recombinant DNA technology. Obtaining a nucleic acid library of tear lipocalin can be carried out using any suitable technique that is known in the art for generating lipocalin muteins with antibody-like properties, i.e. muteins that have affinity towards a given target. Examples of such combinatorial methods are described in detail in the international patent applications WO 99/16873, WO 00/75308, WO 03/029471, WO 03/029462, WO 03/029463, WO 2005/019254, WO 2005/019255, WO 2005/019256, or WO 2006/56464 for instance. The content of each of these patent applications is incorporated by reference herein in its entirety. After expression of the nucleic acid sequences that were subjected to mutagenesis in an appropriate host, the clones carrying the genetic information for the plurality of respective lipocalin muteins, which bind a given target can be selected from the library obtained. Well known techniques can be employed for the selection of these clones, such as phage display (reviewed in Kay, B. K. et al. (1996) supra; Lowman, H. B. (1997) supra or Rodi, D. J., and Makowski, L. (1999) supra), colony screening (reviewed in Pini, A. et al. (2002) *Comb. Chem. High Throughput Screen.* 5, 503-510), ribosome display (reviewed in Amstutz, P. et al. (2001) *Curr. Opin. Biotechnol.* 12, 400-405) or mRNA display as reported in Wilson, D. S. et al. (2001) *Proc. Natl. Acad. Sci. USA* 98, 3750-3755 or the methods specifically described in WO 99/16873, WO 00/75308, WO 03/029471, WO 03/029462, WO 03/029463, WO 2005/019254, WO 2005/019255, WO 2005/019256, or WO 2006/56464.

The nucleic acid molecule encoding the Tlc mutein is expressed using any suitable expression system. The obtained Tlc mutein or Tlc muteins is/are enriched by means of selection and/or isolation. The selection may for example be carried out under competitive conditions. Competitive conditions as used herein means that selection of muteins encompasses at least one step in which the Tlc muteins and GPC-3 are brought in contact in the presence of an additional ligand, which competes with binding of the Tlc muteins to GPC-3. This additional ligand may be a physiological ligand of GPC-3, an excess of GPC-3 itself or any other non-physiological ligand of GPC-3 that binds at least an overlapping epitope to the epitope recognized by the Tlc muteins of the disclosure and thus interferes with target binding of the Tlc muteins. Alternatively, the additional ligand competes with binding of the muteins by complexing an epitope distinct from the binding site of the Tlc muteins to GPC-3 by allosteric effects.

An embodiment of the phage display technique (reviewed in Kay, B. K. et al. (1996), supra; Lowman, H. B. (1997) supra or Rodi, D. J., & Makowski, L. (1999), supra) using temperent M13 phage is given as an example of a selection method that can be employed in the present disclosure. Another embodiment of the phage display technology that can be used for selection of muteins of the disclosure is the hyperphage phage technology as described by Broders et al. (Broders et al. (2003) "Hyperphage. Improving antibody presentation in phage display." *Methods Mol. Biol.* 205:295-302). Other temperent phage such as f1 or lytic phage such as T7 may be employed as well. For the exemplary selection method, M13 phagemids are produced which allow the expression of the mutated lipocalin nucleic acid sequence as a fusion protein with a signal sequence at the N-terminus, such as the OmpA-signal sequence, and with the capsid protein pIII of the phage M13 or fragments thereof capable of being incorporated into the phage capsid at the C-terminus. The C-terminal fragment ΔpIII of the phage capsid protein that includes amino acids 217 to 406 of the wild type sequence is may be used to produce the fusion proteins. In one embodiment a C-terminal fragment of pIII is used, in which the cysteine residue at position 201 is missing or is replaced by another amino acid.

Accordingly, a further embodiment of the methods of the disclosure involves operably fusing a nucleic acid coding for the one or more muteins of human tear lipocalin and resulting from mutagenesis at the 3' end with a gene coding for the coat protein pIII of a filamentous bacteriophage of the M13-family or for a fragment of this coat protein, in order to select at least one mutein for the binding of a given ligand.

The fusion protein may include additional components such as an affinity tag, which allows the immobilization, detection and/or purification of the fusion protein or its parts. Furthermore, a stop codon can be located between the sequence regions encoding tear lipocalin or its muteins and the phage capsid gene or fragments thereof, wherein the stop codon, such as an amber stop codon, is at least partially translated into an amino acid during translation in a suitable suppressor strain.

For example, the phasmid vector pTLPC27, now also called pTlc27 that is described here can be used for the preparation of a phagemid library encoding human tear lipocalin muteins. The nucleic acid molecules coding for the Tlc muteins of the disclosure are inserted into the vector using the two BstXI restriction sites. After ligation a suitable host strain such as *E. coli* XL1-Blue is transformed with the resulting nucleic acid mixture to yield a large number of independent clones. A respective vector can be generated for the preparation of a hyperphagemid library, if desired.

The resulting library is subsequently superinfected in liquid culture with an appropriate M13-helper phage or hyperphage in order to produce functional phagemids. The recombinant phagemid displays the Tlc muteins on its surface as a fusion with the coat protein pIII or a fragment thereof, while the N-terminal signal sequence of the fusion protein is normally cleaved off. On the other hand, it also bears one or more copies of the native capsid protein pIII supplied by the helper phage and is thus capable of infecting a recipient, in general a bacterial strain carrying an F- or F'-plasmid. In case of hyperphage display, the hyperphagemids display the Tlc muteins on their surface as a fusion with the infective coat protein pIII but no native capsid protein. During or after infection with helper phage or hyperphage, gene expression of the fusion protein between the Tlc muteins and the capsid protein pIII can be induced, for example by addition of anhydrotetracycline. The induction conditions are chosen such that a substantial fraction of the phagemids obtained displays at least one Tlc mutein on their surface. In case of hyperphage display induction conditions result in a population of hyperphagemids carrying between three and five fusion proteins consisting of the Tlc muteins and the capsid protein pIII. Various methods are known for isolating the phagemids, such as precipitation with polyethylene glycol. Isolation typically occurs after an incubation period of 6-8 hours.

The isolated phasmids can then be subjected to selection by incubation with the desired target, wherein the target is presented in a form allowing at least temporary immobilization of those phagemids which carry Tlc muteins with the desired binding activity as fusion proteins in their coat. Among the various embodiments known to the person skilled in the art, the target can, for example, be conjugated with a carrier protein such as serum albumin and be bound via this carrier protein to a protein binding surface, for example polystyrene. Microtiter plates suitable for ELISA techniques or so-called "immuno-sticks" can for instance be used for such an immobilization of the target. Alternatively, conjugates of the target with other binding groups, such as biotin, can be used. The target can then be immobilized on a surface which selectively binds this group, for example microtiter plates or paramagnetic particles coated with streptavidin, neutravidin or avidin. If the target is fused to an Fc portion of an immunoglobulin, immobilization can also be achieved with surfaces, for example microtiter plates or paramagnetic particles, which are coated with protein A or protein G.

Non-specific phagemid-binding sites present on the surfaces can be saturated with blocking solutions as they are known for ELISA methods. The phagemids are then typically brought into contact with the target immobilized on the surface in the presence of a physiological buffer. Unbound phagemids are removed by multiple washings. The phagemid particles remaining on the surface are then eluted. For elution, several methods are possible. For example, the phagemids can be eluted by addition of proteases or in the presence of acids, bases, detergents or chaotropic salts or under moderately denaturing conditions. One such method is the elution using buffers of pH 2.2, wherein the eluate is subsequently neutralized. Alternatively, a solution of the free target can be added in order to compete with the immobilized target for binding to the phagemids or target-specific phagemids can be eluted by competition with immunoglobulins or natural liganding proteins which specifically bind to the target of interest.

Afterwards, E. coli cells are infected with the eluted phagemids. Alternatively, the nucleic acids can be extracted from the eluted phagemids and used for sequence analysis, amplification or transformation of cells in another manner. Starting from the E. coli clones obtained in this way, fresh phagemids or hyperphagemids are again produced by superinfection with M13 helper phages or hyperphage according to the method described above and the phagemids amplified in this way are once again subjected to a selection on the immobilized target. Multiple selection cycles are often necessary in order to obtain the phagemids with the Tlc muteins of the disclosure in sufficiently enriched form. The number of selection cycles is in some embodiments chosen in such a way that in the subsequent functional analysis at least 0.1% of the clones studied produce Tlc muteins with detectable affinity for GPC-3. Depending on the size, i.e. the complexity of the library employed, 2 to 8 cycles are typically required to this end.

For the functional analysis of the selected Tlc muteins, an E. coli strain is infected with the phagemids obtained from the selection cycles and the corresponding double stranded phasmid DNA is isolated. Starting from this phasmid DNA, or also from the single-stranded DNA extracted from the phagemids, the nucleic acid sequences of the selected Tlc muteins of the disclosure can be determined by the methods known in the art and the amino acid sequence can be deduced therefrom. The mutated region or the sequence of the entire Tlc mutein can be subcloned on another expression vector and expressed in a suitable host organism. For example, the vector pTLPC26 now also called pTlc26 can be used for expression in E. coli strains such as E. coli TG1. A muteins of tear lipocalin thus produced can be purified by various biochemical methods. A Tlc mutein produced, for example with pTLPC26, may carry an affinity peptide, a so called affinity tag, for instance at its C-terminus and can therefore be purified by affinity chromatography. Examples of an affinity tag include, but are not limited to biotin, the Strep-tag, Strep-tag II (Schmidt et al., supra), oligohistidine, polyhistidine, an immunoglobulin domain, maltose-binding protein, glutathione-S-transferase (GST) or calmodulin binding peptide (CBP).

Some affinity tags are haptens, for example but not limited to, dinitrophenol and digoxigenin. Some affinity tags are epitope tags, such as the FLAG®-peptide (Asp-Tyr-Lys-Asp-Asp-Asp-Asp-Lys-Gly (SEQ ID NO: 44)), the T7 epitope (Ala-Ser-Met-Thr-Gly-Gly-Gln-Gln-Met-Gly (SEQ ID NO: 45)), maltose binding protein (MBP), the HSV epitope of the sequence Gln-Pro-Glu-Leu-Ala-Pro-Glu-Asp-Pro-Glu-Asp (SEQ ID NO: 46) of herpes simplex virus glycoprotein D, the hemagglutinin (HA) epitope of the sequence Tyr-Pro-Tyr-Asp-Val-Pro-Asp-Tyr-Ala (SEQ ID NO: 47), the VSV-G epitope of the Vesicular Stomatitis viral glycoprotein (Cys-Tyr-Thr-Asp-Ile-Glu-Met-Asn-Arg-Leu-Lys (SEQ ID NO: 48)), the E epitope tag of the sequence Gly-Ala-Pro-Val-Pro-Tyr-Pro-Asp-Pro-Leu-Glu-Pro-Arg (SEQ ID NO: 49), the E2 epitope tag of the sequence Gly-Val-Ser-Ser-Thr-Ser-Ser-Asp-Phe-Arg-Asp-Arg (SEQ ID NO: 50), the Tag-100 epitope tag of C-termini of mammalian MAPK/ERK kinases of the sequence Glu-Glu-Thr-Ala-Arg-Phe-Gln-Pro-Gly-Tyr-Arg-Ser (SEQ ID NO: 51), the S-tag of the sequence Lys-Glu-Thr-Ala-Ala-Ala-Lys-Phe-Glu-Arg-Gln-His-Met-Asp-Ser (SEQ ID NO: 52), the "myc" epitope of the transcription factor c-myc of the sequence Glu-Gln-Lys-Leu-Ile-Ser-Glu-Glu-Asp-Leu (SEQ ID NO: 53) and the small V5 epitope present on the P and V proteins of the paramyxovirus of Simian Virus 5 (Gly-Lys-Pro-Ile-Pro-Asn-Pro-Leu-Leu-Gly-Leu-Asp-Ser-Thr (SEQ ID NO: 54)). In addition, but generally not as a single tag, a solubility-enhancing tag such as NusA, thioredoxin (TRX), small ubiquitin-like modifier (SUMO), and ubiquitin (Ub) may be used. Haptens and epitope tags may be used in combination with a corresponding antibody or an antibody like proteinaceous molecule as binding partner. The S-peptide epitope of the sequence Lys-Glu-Thr-Ala-Ala-Ala-Lys-Phe-Glu-Arg-Gln-His-Met-Asp-Ser (SEQ ID NO: may be used as an epitope tag in connection with a respective antibody or in combination with the S-protein as a binding partner (Hackbarth, J S, et al., BioTechniques (2004) 37, 5, 835-839).

The selection can also be carried out by means of other methods. Many corresponding embodiments are known to the person skilled in the art or are described in the literature. Moreover, a combination of methods can be applied. For example, clones selected or at least enriched by "phage display" can additionally be subjected to "colony screening." This procedure has the advantage that individual clones can directly be isolated with respect to the production of a Tlc mutein with detectable binding affinity for GPC-3.

In addition to the use of E. coli as host organism in the "phage display" technique or the "colony screening" method, other bacterial strains, yeast or also insect cells or mammalian cells can be used for this purpose. Further to the selection of a Tlc mutein from a random library as described above, evolutive methods including limited mutagenesis can also be applied in order to optimize a Tlc mutein that already possesses some binding activity for GPC-3 with respect to affinity or specificity for GPC-3 after repeated screening cycles.

It is readily apparent to the skilled person that complex formation is dependent on many factors such as concentration of the binding partners, the presence of competitors, ionic strength of the buffer system etc. Selection and enrichment is generally performed under conditions allowing the isolation of Tlc muteins having, in complex with the desired target, a dissociation constant of at least 200 nM. However, the washing and elution steps can be carried out under varying stringency. A selection with respect to the kinetic characteristics is possible as well. For example, the selection can be performed under conditions, which favor complex formation of the target with Tlc muteins that show a slow dissociation from the target, or in other words a low $k_{off}$ rate. Alternatively, selection can be performed under conditions, which favour fast formation of the complex between the Tlc muteins and the target, or in other words a high $k_{on}$ rate. As a further illustrative alternative, the screening can be performed under conditions that select for improved thermostability of the Tlc muteins (compared to either the wild type tear lipocalin or a Tlc mutein that already has affinity towards a pre-selected target).

Once a Tlc mutein with affinity to GPC-3 has been selected, it is additionally possible to subject such a Tlc mutein to another mutagenesis in order to subsequently select variants of even higher affinity or variants with improved properties such as higher thermostability, improved serum stability, thermodynamic stability, improved solubility, improved monomeric behavior, improved resistance against thermal denaturation, chemical denaturation, proteolysis, or detergents etc. This further mutagenesis, which in case of aiming at higher affinity can be considered as in vitro "affinity maturation", can be achieved by site specific mutation based on rational design or a random mutation. Another possible approach for obtaining a higher affinity or improved properties is the use of error-prone PCR, which results in point mutations over a selected range of sequence positions of the lipocalin mutein. The error-prone PCR can be carried out in accordance with any known protocol such as the one described by Zaccolo et al. (1996) J. Mol. Biol. 255, 589-603. Other methods of random mutagenesis that are suitable for such purposes include random insertion/deletion (RID) mutagenesis as described by Murakami, H et al. (2002) Nat. Biotechnol. 20, 76-81 or nonhomologous random recombination (NRR) as described by Bittker, J. A et al. (2002) Nat. Biotechnol. 20, 1024-1029. If desired, affinity maturation can also be carried out according to the procedure described in WO 00/75308 or Schlehuber, S. et al., (2000) J. Mol. Biol. 297, 1105-1120, where muteins of the bilin-binding protein having high affinity to digoxigenin were obtained.

A Tlc mutein of the disclosure may be used for complex formation with GPC3. The mutein may also be able to bind an immunogenic fragment of GPC-3. An immunogenic fragment of GPC-3 is a fragment that has one or more epitopes, mimotopes or other antigenic determinants, and is thus capable of inducing an immune response or against which an antibody can be raised. The immunogenic fragment may include a single epitope or may have a plurality of epitopes. Since an antigen-presenting system, e.g. a carrier protein, may be used to provide the size required for recognition by an immune system, no particular size limitation applies to the immunogenic fragment. Hence, the immunogenic fragment may also be a "hapten", i.e. a fragment that need not be antigenic per se or may have low immunogenicity, in particular due to its small molecular weight and accordingly size. Typically an immunogenic fragment can, alone or when presented on a carrier, be bound by an immunoglobulin or by a T cell receptor (TCR) if presented by MHC molecules. An immunogenic fragment is typically, alone or when presented in the form of the antigen-presenting system, capable of inducing a humoral immune response and/or cellular immune response leading for instance to the activation of B- and/or T-lymphocytes.

In this context it is also noted that the complex formation between the respective mutein and its ligand is influenced by many different factors such as the concentrations of the respective binding partners, the presence of competitors, pH and the ionic strength of the buffer system used, and the experimental method used for determination of the dissociation constant $K_D$ (for example fluorescence titration, competition ELISA or surface plasmon resonance, just to name a few) or even the mathematical algorithm which is used for evaluation of the experimental data.

Therefore, it is also clear to the skilled person that the $K_D$ values (dissociation constant of the complex formed between the respective mutein and its ligand) given here may vary within a certain experimental range, depending on the method and experimental setup that is used for determining the affinity of a particular lipocalin mutein for a given ligand. This means, there may be a slight deviation in the measured $K_D$ values or a tolerance range depending, for example, on whether the $K_D$ value was determined by surface plasmon resonance (Biacore) or by competition ELISA.

Also included in the scope of the present disclosure are forms of the above muteins, in which the respective mutein has been altered or modified with respect to its potential immunogenicity.

Cytotoxic T-cells recognize peptide antigens on the cell surface of an antigen-presenting cell in association with a class I major histocompatibility complex (MHC) molecule. The ability of the peptides to bind to MHC molecules is allele specific and correlates with their immunogenicity. In order to reduce immunogenicity of a given protein, the ability to predict which peptides in a protein have the potential to bind to a given MHC molecule is of great value. Approaches that employ a computational threading approach to identify potential T-cell epitopes have been previously described to predict the binding of a given peptide sequence to MHC class I molecules (Altuvia et al. (1995) *J. Mol. Biol.* 249, 244-250).

Such an approach may also be utilized to identify potential T-cell epitopes in the Tlc muteins of the disclosure and to make depending on its intended use a selection of a specific Tlc mutein on the basis of its predicted immunogenicity. It may be furthermore possible to subject peptide regions which have been predicted to contain T-cell epitopes to additional mutagenesis to reduce or eliminate these T-cell epitopes and thus minimize immunogenicity. The removal of amphipathic epitopes from genetically engineered antibodies has been described (Mateo et al. (2000) *Hybridoma* 19, 6, 463-471) and may be adapted to the Tlc muteins of the disclosure.

The Tlc muteins thus obtained may possess a minimized immunogenicity, which is desirable for their use in therapeutic and diagnostic applications, such as those described below.

For some applications, it is also useful to employ the Tlc muteins of the disclosure in a labeled form. Accordingly, the disclosure is also directed to Tlc muteins which are conjugated to a label selected from the group consisting of enzyme labels, radioactive labels, colored labels, fluorescent labels, chromogenic labels, luminescent labels, haptens, digoxigenin, biotin, metal complexes, metals, and colloidal gold. The Tlc mutein may also be conjugated to a low molecular weight organic compound. The term "low molecular weight organic compound" as used herein denotes a monomeric carbon-based compound, which may have aliphatic, alicyclic and/or aromatic moieties. In typical embodiments the low molecular weight organic compound is an organic compound that has a main chain of at least two carbon atoms, and in some embodiments not more than 7 or 12 rotatable carbon bonds. Such a compound has a molecular weight in the range from about 100 to about 2000 Dalton, such as from about 100 to about 1000 Dalton. It may optionally include one or two metal atoms.

In general, it is possible to label the Tlc muteins with any appropriate chemical substance or enzyme, which directly or indirectly generates a detectable compound or signal in a chemical, physical, optical, or enzymatic reaction. An example for a physical reaction and at the same time optical reaction/marker is the emission of fluorescence upon irradiation or the emission of X-rays when using a radioactive label. Alkaline phosphatase, horseradish peroxidase and β-galactosidase are examples of enzyme labels (and at the same time optical labels) which catalyze the formation of chromogenic reaction products. In general, all labels commonly used for antibodies (except those exclusively used with the sugar moiety in the Fc part of immunoglobulins) can also be used for conjugation to the Tlc muteins of the disclosure. The Tlc muteins of the disclosure may also be conjugated with any suitable therapeutically active agent, e.g., for the targeted delivery of such agents to a given cell, tissue or organ or for the selective targeting of cells, e.g., of tumor cells without affecting the surrounding normal cells. Examples of such therapeutically active agents include radionuclides, toxins, small organic molecules, and therapeutic peptides (such as peptides acting as agonists/antagonists of a cell surface receptor or peptides competing for a protein binding site on a given cellular target). The Tlc muteins of the disclosure may, however, also be conjugated with therapeutically active nucleic acids such as antisense nucleic acid molecules, small interfering RNAs, micro RNAs or ribozymes. Such conjugates can be produced by methods well known in the art.

In one embodiment, the Tlc muteins of the disclosure may also be coupled to a targeting moiety that targets a specific body region in order to deliver the inventive muteins to a desired region or area within the body. One example wherein such modification may be desirable is the crossing of the blood-brain-barrier. In order to cross the blood-brain barrier, the Tlc muteins of the disclosure may be coupled to moieties that facilitate the active transport across this barrier (see Gaillard P J, et al., Diphtheria-toxin receptor-targeted brain drug delivery. *International Congress Series*, 2005 1277, 185-198 or Gaillard P J, et al. Targeted delivery across the blood-brain barrier. *Expert Opin Drug Deliv.* 2005 2, 2, 299-309. Such moieties are for example available under the trade name 2B-Trans™ (to-BBB technologies BV, Leiden, NL).

As indicated above, a Tlc mutein of the disclosure may in some embodiments be conjugated to a moiety that extends the serum half-life of the mutein (in this regard see also PCT publication WO 2006/56464 where such conjugation strategies are described with references to muteins of human neutrophile gelatinase-associated lipocalin with binding affinity for CTLA-4). The moiety that extends the serum half-life may be a polyalkylene glycol molecule, hydroxyethyl starch, fatty acid molecules, such as palmitic acid (Vajo & Duckworth 2000, *Pharmacol. Rev.* 52, 1-9), an Fc part of an immunoglobulin, a CH3 domain of an immunoglobulin, a CH4 domain of an immunoglobulin, albumin or a fragment thereof, an albumin binding peptide, or an albumin binding protein, transferrin to name only a few. The albumin binding protein may be a bacterial albumin binding protein, an antibody, an antibody fragment including domain antibodies (see U.S. Pat. No. 6,696,245, for example), or a lipocalin mutein with binding activity for albumin. Accordingly, suitable conjugation partners for extending the half-life of a Tlc mutein of the disclosure include albumin (Osborn, B. L. et al., 2002, *J. Pharmacol. Exp. Ther.* 303, 540-548), or an albumin binding protein, for example, a bacterial albumin binding domain, such as the one of streptococcal protein G (König, T., & Skerra, A. (1998) *J. Immunol. Methods* 218, 73-83). Other examples of albumin binding peptides that can be used as conjugation partner are, for instance, those having a Cys-Xaa$_1$-Xaa$_2$-Xaa$_3$-Xaa$_4$-Cys consensus sequence, wherein Xaa$_1$ is Asp, Asn, Ser, Thr, or Trp; Xaa$_2$ is Asn, Gln, His, Ile, Leu, or Lys; Xaa$_3$ is Ala, Asp, Phe, Trp, or Tyr; and Xaa$_4$ is Asp, Gly, Leu, Phe, Ser, or Thr as described in US patent application 2003/0069395 or Dennis et al. (Dennis, M. S., Zhang, M., Meng, Y. G., Kadkhodayan, M., Kirchhofer, D., Combs, D. & Damico, L. A. (2002) *J Biol Chem* 277, 35035-35043).

In other embodiments, albumin itself or a biological active fragment of albumin can be used as conjugation partner of a Tlc mutein of the disclosure. The term "albumin" includes all mammal albumins such as human serum albumin or bovine serum albumin or rat albumine. The albumin or fragment thereof can be recombinantly produced as described in U.S. Pat. No. 5,728,553 or European patent applications EP 0 330 451 and EP 0 361 991. Recombinant human albumin (Recombumin®) Novozymes Delta Ltd. (Nottingham, UK) can be conjugated or fused to a Tlc mutein of the disclosure in order to extend the half-life of the mutein.

If the albumin-binding protein is an antibody fragment it may be a domain antibody. Domain Antibodies (dAbs) are engineered to allow precise control over biophysical properties and in vivo half-life to create the optimal safety and efficacy product profile. Domain Antibodies are for example commercially available from Domantis Ltd. (Cambridge, UK and MA, USA).

Using transferrin as a moiety to extend the serum half-life of the Tlc muteins of the disclosure, the muteins can be genetically fused to the N or C terminus, or both, of non-glycosylated transferrin. Non-glycosylated transferrin has a half-life of 14-17 days, and a transferrin fusion protein will similarly have an extended half-life. The transferrin carrier also provides high bioavailability, biodistribution and circulating stability. This technology is commercially available from BioRexis (BioRexis Pharmaceutical Corporation, PA, USA). Recombinant human transferrin (DeltaFerrin™) for use as a protein stabilizer/half-life extension partner is also commercially available from Novozymes Delta Ltd. (Nottingham, UK).

If an Fc part of an immunoglobulin is used for the purpose to prolong the serum half-life of the Tlc muteins of the disclosure, the SynFusion™ technology, commercially available from Syntonix Pharmaceuticals, Inc (MA, USA), may be used. The use of this Fc-fusion technology allows the creation of longer-acting biopharmaceuticals and may for example consist of two copies of the mutein linked to the Fc region of an antibody to improve pharmacokinetics, solubility, and production efficiency.

Yet another alternative to prolong the half-life of the Tlc muteins of the disclosure is to fuse to the N- or C-terminus of the muteins long, unstructured, flexible glycine-rich sequences (for example poly-glycine with about 20 to 80 consecutive glycine residues). This approach disclosed in WO2007/038619, for example, has also been term "rPEG" (recombinant PEG).

If polyalkylene glycol is used as conjugation partner, the polyalkylene glycol can be substituted, unsubstituted, linear or branched. It can also be an activated polyalkylene derivative. Examples of suitable compounds are polyethylene glycol (PEG) molecules as described in WO 99/64016, in U.S. Pat. No. 6,177,074 or in U.S. Pat. No. 6,403,564 in relation to interferon, or as described for other proteins such as PEG-modified asparaginase, PEG-adenosine deaminase (PEG-ADA) or PEG-superoxide dismutase (see for example, Fuertges et al. (1990) The Clinical Efficacy of Poly(Ethylene Glycol)-Modified Proteins *J. Control. Release* 11, 139-148). The molecular weight of such a polymer, such as polyethylene glycol, may range from about 300 to about 70.000 Dalton, including, for example, polyethylene glycol with a molecular weight of about 10.000, of about 20.000, of about 30.000 or of about 40.000 Dalton. Moreover, as e.g. described in U.S. Pat. No. 6,500,930 or 6,620,413, carbohydrate oligo- and polymers such as starch or hydroxyethyl starch (HES) can be conjugated to a mutein of the disclosure for the purpose of serum half-life extension.

If one of the above moieties is conjugated to the Tlc muteins of the disclosure, conjugation to an amino acid side chain can be advantageous. Suitable amino acid side chains may occur naturally in the amino acid sequence of the mature human tear lipocalin or may be introduced by mutagenesis. In case a suitable binding site is introduced via mutagenesis, one possibility is the replacement of an amino acid at the appropriate position by a cysteine residue. The newly created cysteine residue can be utilized to conjugate the muteins to moiety prolonging the serum half-life of the muteins, such as PEG or an activated derivative thereof.

In another embodiment, in order to provide suitable amino acid side chains for conjugating one of the above moieties to the Tlc muteins of the disclosure artificial amino acids may be introduced by mutagenesis. Generally, such artificial amino acids are designed to be more reactive and thus to facilitate the conjugation to the desired moiety. One example of such an artificial amino acid that may be introduced via an artificial tRNA is para-acetyl-phenylalanine.

For several applications of the Tlc muteins disclosed herein it may be advantageous to use them in the form of fusion proteins. In some embodiments, the Tlc muteins are fused at their N-terminus or C-terminus to a protein, a protein domain or a peptide such as a signal sequence and/or an affinity tag.

For pharmaceutical applications, a Tlc mutein disclosed herein may be fused to a fusion partner that extends the in vivo serum half-life of the mutein (see again PCT publication WO 2006/56464 where suitable fusion partner are described with references to muteins of human neutrophile gelatinase-associated lipocalin with binding affinity for CTLA-4). Similar to the conjugates described above, the fusion partner may be an Fc part of an immunoglobulin, a CH3 domain of an immunoglobulin, a CH4 domain of an immunoglobulin, albumin, an albumin binding peptide or an albumin binding protein, to name only a few. Again, the albumin binding protein may be a bacterial albumin binding protein or a lipocalin mutein with binding activity for albumin. Accordingly, suitable fusion partners for extending the half-life of a lipocalin mutein of the disclosure include albumin (Osborn, B. L. et al. (2002) supra *J. Pharmacol. Exp. Ther.* 303, 540-548), or an albumin binding protein, for example, a bacterial albumin binding domain, such as the one of streptococcal protein G (König, T., & Skerra, A. (1998) *J. Immunol. Methods* 218, 73-83). The albumin binding peptides described in Dennis et al, supra (2002) or US patent application 2003/0069395 having a Cys-$Xaa_1$-$Xaa_2$-$Xaa_3$-$Xaa_4$-Cys consensus sequence, wherein $Xaa_1$ is Asp, Asn, Ser, Thr, or Trp; $Xaa_2$ is Asn, Gln, His, Ile, Leu, or Lys; $Xaa_3$ is Ala, Asp, Phe, Trp, or Tyr; and $Xaa_4$ is Asp, Gly, Leu, Phe, Ser, or Thr can also be used as fusion partner. It is also possible to use albumin itself or a biological active fragment of albumin as fusion partner of a Tlc mutein disclosed herein. The term "albumin" includes all mammal albumins such as human serum albumin or bovine serum albumin or rat serum albumin. The recombinant production of albumin or fragments thereof is well known in the art and for example described in U.S. Pat. No. 5,728,553, European patent application EP 0 330 451 or EP 0 361 991.

The fusion partner may confer new characteristics to the Tlc muteins of the disclosure such as enzymatic activity or binding affinity for other molecules. Examples of suitable fusion proteins are alkaline phosphatase, horseradish peroxidase, gluthation-S-transferase, the albumin-binding domain of protein G, protein A, antibody fragments, oligomerization domains, lipocalin muteins of same or different binding specificity (which results in the formation of "Duocalins", cf. Schlehuber, S., and Skerra, A. (2001), Duocalins, engineered ligand-binding proteins with dual specificity derived from the lipocalin fold. *Biol. Chem.* 382, 1335-1342) or toxins.

In particular, it may be possible to fuse a Tlc mutein disclosed herein with a separate enzyme active site such that both "components" of the resulting fusion protein together act on a given therapeutic target. The binding domain of the Tlc mutein attaches to the disease-causing target, allowing the enzyme domain to abolish the biological function of the target.

Affinity tags such as the Strep-Tag® or Strep-Tag® II (Schmidt, T. G. M. et al. (1996) *J. Mol. Biol.* 255, 753-766), the myc-tag, the FLAG-tag, the $His_6$-tag (SEQ ID NO: 55) or the HA-tag or proteins such as glutathione-S-transferase also allow easy detection and/or purification of recombinant proteins are further examples of suitable fusion partners. Finally, proteins with chromogenic or fluorescent properties such as the green fluorescent protein (GFP) or the yellow fluorescent protein (YFP) are suitable fusion partners for Tlc muteins of the disclosure as well.

The term "fusion protein" as used herein also includes Tlc muteins according to the disclosure containing a signal sequence. Signal sequences at the N-terminus of a polypeptide direct this polypeptide to a specific cellular compartment, for example the periplasm of *E. coli* or the endoplasmatic reticulum of eukaryotic cells. A large number of signal sequences are known in the art. An illustrative signal sequence for secretion a polypeptide into the periplasm of *E. coli* is the OmpA-signal sequence.

The present disclosure also relates to nucleic acid molecules (DNA and RNA) that include nucleotide sequences coding for the Tlc muteins of the disclosure. Since the degeneracy of the genetic code permits substitutions of certain codons by other codons specifying the same amino acid, the disclosure is not limited to a specific nucleic acid molecule encoding a Tlc mutein as described herein but encompasses all nucleic acid molecules that include nucleotide sequences encoding a functional mutein.

Therefore, the present disclosure also includes a nucleic acid sequence encoding a Tlc mutein that has a mutation at least one codon of any of the amino acid sequence positions 26-34, 55-61, 64, 79, 101, 104-106, 108, 111, 114 and 153 of the linear polypeptide sequence of the mature human tear lipocalin (SWISS-PROT Data Bank Accession Number P31025), wherein the codons encoding at least one of the cysteine residues at sequence positions 61 and 153 of the linear polypeptide sequence of the mature human tear lipocalin have been mutated to encode any other amino acid residue.

The disclosure as disclosed herein also includes nucleic acid molecules encoding the Tlc muteins of the disclosure, which include additional mutations outside the indicated sequence positions of experimental mutagenesis. Such mutations are often tolerated or can even prove to be advantageous, for example if they contribute to an improved folding efficiency, serum stability, thermal stability or ligand binding affinity of the muteins.

A nucleic acid molecule disclosed in this application may be "operably linked" to a regulatory sequence (or regulatory sequences) to allow expression of this nucleic acid molecule.

A nucleic acid molecule, such as DNA, is referred to as "capable of expressing a nucleic acid molecule" or capable "to allow expression of a nucleotide sequence" if it includes sequence elements which contain information regarding to transcriptional and/or translational regulation, and such sequences are "operably linked" to the nucleotide sequence encoding the polypeptide. An operable linkage is a linkage in which the regulatory sequence elements and the sequence to be expressed are connected in a way that enables gene expression. The precise nature of the regulatory regions necessary for gene expression may vary among species, but in general these regions include a promoter which, in prokaryotes, contains both the promoter per se, i.e. DNA elements directing the initiation of transcription, as well as DNA elements which, when transcribed into RNA, will signal the initiation of translation. Such promoter regions normally include 5' non-coding sequences involved in initiation of transcription and translation, such as the −35/−10 boxes and the Shine-Dalgarno element in prokaryotes or the TATA box, CAAT sequences, and 5'-capping elements in eukaryotes. These regions can also include enhancer or repressor elements as well as translated signal and leader sequences for targeting the native polypeptide to a specific compartment of a host cell.

In addition, the 3' non-coding sequences may contain regulatory elements involved in transcriptional termination, polyadenylation or the like. If, however, these termination sequences are not satisfactory functional in a particular host cell, then they may be substituted with signals functional in that cell.

Therefore, a nucleic acid molecule of the disclosure can include a regulatory sequence, such as a promoter sequence. In some embodiments a nucleic acid molecule of the disclosure includes a promoter sequence and a transcriptional termination sequence. Suitable prokaryotic promoters are, for example, the tet promoter, the lacUV5 promoter or the T7 promoter. Examples of promoters useful for expression in eukaryotic cells are the SV40 promoter or the CMV promoter.

The nucleic acid molecules of the disclosure can also be part of a vector or any other kind of cloning vehicle, such as a plasmid, a phagemid, a phage, a baculovirus, a cosmid or an artificial chromosome.

In one embodiment, the nucleic acid molecule is included in a phasmid. A phasmid vector denotes a vector encoding the intergenic region of a temperent phage, such as M13 or f1, or a functional part thereof fused to the cDNA of interest. After superinfection of the bacterial host cells with such an phagemid vector and an appropriate helper phage (e.g. M13K07, VCS-M13 or R408) intact phage particles are produced, thereby enabling physical coupling of the encoded heterologous cDNA to its corresponding polypeptide displayed on the phage surface (see e.g. Lowman, H. B. (1997) Annu. Rev. Biophys. Biomol. Struct. 26, 401-424, or Rodi, D. J., and Makowski, L. (1999) Curr. Opin. Biotechnol. 10, 87-93).

Such cloning vehicles can include, aside from the regulatory sequences described above and a nucleic acid sequence encoding a Tlc mutein as described herein, replication and control sequences derived from a species compatible with the host cell that is used for expression as well as selection markers conferring a selectable phenotype on transformed or transfected cells. Large numbers of suitable cloning vectors are known in the art, and are commercially available.

The DNA molecule encoding a Tlc mutein as described herein, and in particular a cloning vector containing the coding sequence of such a mutein can be transformed into a host cell capable of expressing the gene. Transformation can be performed using standard techniques. Thus, the disclosure is also directed to a host cell containing a nucleic acid molecule as disclosed herein.

The transformed host cells are cultured under conditions suitable for expression of the nucleotide sequence encoding a fusion protein of the disclosure. Suitable host cells can be prokaryotic, such as *Escherichia coli* (*E. coli*) or *Bacillus subtilis*, or eukaryotic, such as *Saccharomyces cerevisiae*, *Pichia pastoris*, SF9 or High5 insect cells, immortalized mammalian cell lines (e.g. HeLa cells or CHO cells) or primary mammalian cells.

The disclosure also relates to a method for the production of a Tlc mutein as described herein, wherein the mutein, a fragment of the mutein or a fusion protein of the mutein and another polypeptide is produced starting from the nucleic acid coding for the mutein by means of genetic engineering methods. The method can be carried out in vivo, the Tlc mutein can for example be produced in a bacterial or eucaryotic host organism and then isolated from this host organism or its culture. It is also possible to produce a protein in vitro, for example by use of an in vitro translation system.

When producing the Tlc mutein in vivo a nucleic acid encoding such mutein is introduced into a suitable bacterial or eukaryotic host organism by means of recombinant DNA technology (as already outlined above). For this purpose, the host cell is first transformed with a cloning vector that includes a nucleic acid molecule encoding a Tlc mutein as described herein using established standard methods. The host cell is then cultured under conditions, which allow expression of the heterologous DNA and thus the synthesis of the corresponding polypeptide. Subsequently, the polypeptide is recovered either from the cell or from the cultivation medium.

In some Tlc muteins of the disclosure, the naturally occurring disulfide bond between Cys 61 and Cys 153 is removed. Accordingly, such muteins (or any other Tlc mutein that does not include an intramolecular disulfide bond) can be produced in a cell compartment having a reducing redox milieu, for example, in the cytoplasma of Gram-negative bacteria. In case a Tlc mutein as described herein includes intramolecular disulfide bonds, it may be desired to direct the nascent polypeptide to a cell compartment having an oxidizing redox milieu using an appropriate signal sequence. Such an oxidizing environment may be provided by the periplasm of Gram-negative bacteria such as *E. coli*, in the extracellular milieu of Gram-positive bacteria or in the lumen of the endoplasmatic reticulum of eukaryotic cells and usually favors the formation of structural disulfide bonds. It is, however, also possible to produce a Tlc mutein as described herein in the cytosol of a host cell, such as *E. coli*. In this case, the polypeptide can either be directly obtained in a soluble and folded state or recovered in form of inclusion bodies, followed by renaturation in vitro. A further option is the use of specific host strains having an oxidizing intracellular milieu, which may thus allow the formation of disulfide bonds in the cytosol (Venturi M, et al. (2002) *J. Mol. Biol.* 315, 1-8).

However, a Tlc mutein as described herein may not necessarily be generated or produced only by use of genetic engineering. Rather, such a mutein can also be obtained by chemical synthesis such as Merrifield solid phase polypeptide synthesis or by in vitro transcription and translation. It is for example possible that promising mutations are identified using molecular modeling and then to synthesize the wanted (designed) polypeptide in vitro and investigate the binding activity for GPC-3. Methods for the solid phase and/or solution phase synthesis of proteins are well known in the art (see e.g. Bruckdorfer, T. et al. (2004) *Curr. Pharm. Biotechnol.* 5, 29-43).

In another embodiment, the Tlc muteins of the disclosure may be produced by in vitro transcription/translation employing well-established methods known to those skilled in the art.

The present disclosure also relates to a pharmaceutical composition that includes at least one Tlc mutein disclosed herein or a fusion protein or conjugates thereof and, optionally, a pharmaceutically acceptable excipient.

The Tlc muteins according to the disclosure can be administered via any parenteral or non-parenteral (e.g. enteral) route that is therapeutically effective for proteinaceous drugs.

Accordingly, the Tlc muteins of the disclosure can be formulated into compositions using pharmaceutically acceptable ingredients as well as established methods of preparation (Gennaro and Gennaro (2000) *Remington: The Science and Practice of Pharmacy,* 20th Ed., Lippincott Williams & Wilkins, Philadelphia, Pa.). To prepare the pharmaceutical compositions, pharmaceutically inert inorganic or organic excipients can be used.

The present disclosure also involves the use of one or more Tlc muteins as described for complex formation with GPC-3.

Therefore, in another aspect of the disclosure, the disclosed muteins are used for the detection of GPC-3. Such use may include the steps of contacting one or more said muteins, under suitable conditions, with a sample suspected of containing GPC-3, thereby allowing formation of a complex between the muteins and GPC-3, and detecting the complexed muteins by a suitable signal.

The detectable signal can be caused by a label, as explained above, or by a change of physical properties due to the binding, i.e. the complex formation, itself. One example is plasmon surface resonance, the value of which is changed during binding of binding partners from which one is immobilized on a surface such as a gold foil.

The muteins disclosed herein may also be used for the separation of GPC-3. Such use may include the steps of contacting one or more said mutein, under suitable conditions, with a sample supposed to contain GPC-3, thereby allowing formation of a complex between the muteins and GPC-3, and separating the complex from the sample.

In the use of the disclosed muteins for the detection of GPC-3 as well as the separation of GPC-3, the muteins and/or GPC-3 or a domain or fragment thereof may be immobilized on a suitable solid phase.

The Tlc muteins disclosed herein and its derivatives can be used in many fields similar to antibodies or fragments thereof. For example, the Tlc muteins can be used for labeling with an enzyme, an antibody, a radioactive substance or any other group having biochemical activity or defined binding characteristics. By doing so, their respective targets or conjugates or fusion proteins thereof can be detected or brought in contact with them. In addition, Tlc muteins of the disclosure can serve to detect chemical structures by means of established analytical methods (e.g. ELISA or Western Blot) or by microscopy or immunosensorics. In this regard, the detection signal can either be generated directly by use of a suitable mutein conjugate or fusion protein or indirectly by immunochemical detection of the bound mutein via an antibody.

Numerous possible applications for the Tlc muteins of the disclosure also exist in medicine. In addition to their use in diagnostics, a mutant polypeptide of the disclosure, which binds, for example, tissue- or tumor-specific cellular surface molecules can be generated. Such a mutein may, for example, be employed in conjugated form or as a fusion protein for "tumor imaging" or directly for cancer therapy.

In a further aspect, the disclosure also encompasses the use of disclosed Tlc muteins for the manufacture of a pharmaceutical composition. The pharmaceutical composition thus obtained may be suited for the treatment of a disease or disorder associated with an altered, e.g. increased or reduced, level of GPC-3, such as anaemia. The pharmaceutical composition may be used as monotherapy or as combination therapy. Accordingly, the disclosure also provides Tlc muteins for the treatment of a disease or disorder associated with an altered, e.g. increased or reduced, level of GPC-3, such as anaemia.

In yet another aspect the disclosure relates to the use of a Tlc mutein disclosed herein in diagnosis. Such use is preferably for the diagnosis of a disease or disorder associated with an altered level of GPC-3 as well as a respective method of diagnosis.

Accordingly, the disclosure also relates to a Tlc mutein as described above for the diagnosis of a disease or disorder associated with an altered, e.g. increased or reduced, level of GPC-3. In some embodiments the disease is cancer, including, but not limited to, liver cancer or melanoma. The cancer to be diagnosed is not particularly limited, and specific examples may include liver cancer, pancreatic cancer, cholangiocarcinoma, lung cancer, colon cancer, colorectal malignancies, neurofibrosarcoma, neuroblastoma, mammary cancer, breast cancer, ovarian cancer, prostate cancer, leukemia and lymphoma, Wilm's tumor, preferably liver cancer or (primary/early) hepatocellular carcinoma (see Sinnett D. GPC3 (glypican 3). Atlas Genet Cytogenet Oncol Haematol. May 2002).

In still another aspect, the present disclosure features a diagnostic or analytical kit comprising a Tlc mutein according to the disclosure.

In still another aspect, the present disclosure features a method for in vivo imaging in a subject, including administering to said subject a mutein of the disclosure or a pharmaceutical composition comprising a mutein of the disclosure.

The subject may be a mammal, such as a human, a dog, a mouse, a rat, a pig, and an ape such as cynomolgous monkeys to name only a few illustrative examples.

B. Use of Lipocalin Muteins for Target-Specific Delivery to Cells Expressing GPC-3

As mentioned above, international patent application PCT/EP2011/070119 disclosed lipocalin muteins, derived from human lipocalin 2 (or hNGAL), which are capable of binding Glypican-3 (GPC-3).

In another aspect, the present disclosure relates to the use of human lipocalin 2 muteins (hNGAL muteins) against GPC-3 disclosed in PCT/EP2011/070119, as the targeting domain for cytotoxic drugs, for the treatment of GPC-3-expressing cancers.

To reduce the systemic toxicity of cytotoxic drugs and provide target-specific delivery of cytotoxic drugs to cells that express GPC-3, followed by internalization and release of the drugs inside the cells, using targeting moieties such as antibodies, peptides or aptamers to deliver the drugs to such cells has been tried. Since it is desirable for the skilled to have other targeting moieties with a level of specificity that can reduce deleterious side-effects, in various embodiments, the present disclosure provides a new technology, using at least one hNGAL mutein that can be internalized from GPC-3-expressing cells' surface, to deliver therapeutic moieties or detectable labels selectively (e.g. to antigens) to cells that express GPC-3 and reduce or eliminate off-target toxic effects.

By using one or more such hNGAL muteins to target a toxin to only those cells that express GPC-3, cancer cells can be eliminated while allowing healthy, essential cells to remain unharmed. Thus, these hNGAL muteins represent a novel class of therapeutic and diagnostic candidate for treatment cancers associated with the expression of GPC-3.

In a further group of embodiments, the hNGAL muteins of the disclosure can be coupled to one or more therapeutic moieties or one or more detectable labels and therefore deliver such therapeutic moiety or detectable label to the cells that express GPC-3. In some embodiments, the hNGAL mutein has at least 75%, at least 80%, at least 85%, at least 90%, at least 95% or greater amino acid sequence identity to SEQ ID NO: 1.

In some preferred embodiment, the hNGAL muteins of the disclosure includes various muteins of human Lipocalin 2 that specifically bind GPC-3. In this sense, GPC-3 can be regarded a non-natural ligand of wild type human Lipocalin 2, where "non-natural ligand" refers to a compound that does not bind to wildtype lipocalins, including human Lipocalin 2 under physiological conditions. By engineering wild-type human Lipocalin 2 with mutations at certain positions, the hNGAL muteins of the disclosure have demonstrated that high affinity and high specificity for a non-natural ligand is possible. In one aspect, at least at 1, 2, 3, 4, 5, 6, 7, 8, 9, 10, 11, 12, 13, 14, 15, 16, 17, 18, 19, and/or 20 nucleotide triplet(s) encoding for any of the sequence positions 36, 40, 41, 49, 52, 68, 70, 72, 73, 77, 79, 81, 96, 100, 103, 106, 125, 127, 132, and/or 134 of the linear polypeptide sequence of the mature human Lipocalin 2 (SEQ ID NO: 1), a random mutagenesis can be carried out by allowing substitution at these positions by a subset of nucleotide triplets.

In a further group of embodiments, the hNGAL muteins of the disclosure have a mutated amino acid residue at any one or more, including at least at any two, three, four, five, six, seven, eight, nine, ten, eleven, twelve, thirteen, fourteen, fifteen, sixteen, seventeen, eighteen, nineteen or twenty, of the sequence positions of the sequence positions corresponding to the sequence positions 36, 40, 41, 49, 52, 68, 70, 72, 73, 77, 79, 81, 96, 100, 103, 106, 125, 127, 132, and 134 of the linear polypeptide sequence of the mature human Lipocalin 2 (SEQ ID NO: 1).

In further particular embodiments, a hNGAL mutein of the disclosure has an amino acid sequence as set forth in any one of SEQ ID NOs: 2-6 or of a fragment or variant thereof. The term "fragment" as used in the present disclosure in connection with the hNGAL muteins of the disclosure relates to proteins or peptides derived from full-length mature human tear lipocalin that are N-terminally and/or C-terminally shortened, i.e. lacking at least one of the N-terminal and/or C-terminal amino acids. Such fragments comprise preferably at least 10, more preferably 20, most preferably 30 or more consecutive amino acids of the primary sequence of mature human tear lipocalin and are usually detectable in an immunoassay of mature human tear lipocalin. The term "variant" as used in the present disclosure in connection with the hNGAL muteins of the disclosure relates to derivatives of a protein or peptide that comprise modifications of the amino acid sequence, for example by substitution, deletion, insertion or chemical modification. Preferably, such modifications do not reduce the functionality of the protein or peptide. Such variants include proteins, wherein one or more amino acids have been replaced by their respective D-stereoisomers or by amino acids other than the naturally occurring 20 amino acids, such as, for example, ornithine, hydroxyproline, citrulline, homoserine, hydroxylysine, norvaline. However, such substitutions may also be conservative, i.e. an amino acid residue is replaced with a chemically similar amino acid residue. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan.

A "targeting moiety" is the portion of an immunoconjugate intended to target the immunoconjugate to a cell of interest. For example, the targeting moiety can be an antibody, a scFv, a dsFv, an Fab, or an F(ab').

A "therapeutic moiety" can be any cytotoxic drug (e.g. cytotixin) or immunomodulatory drug, intended to act as a therapeutic agent.

The term "therapeutic agent" includes any number of compounds currently known or later developed to act as anti-neoplasties, antiinflammatories, cytokines, anti-infectives, enzyme activators or inhibitors, allosteric modifiers, antibiotics or other agents administered to induce a desired therapeutic effect in a patient. The therapeutic agent may also be a toxin or a radioisotope, where the therapeutic effect intended is, for example, the killing of a cancer cell.

The term "toxin" includes reference to abrin, ricin, *Pseudomonas* exotoxin (PE), diphtheria toxin (DT), botulinum toxin, or modified toxins thereof. For example, PE and DT are highly toxic compounds that typically bring about death through liver toxicity. PE and DT, however, can be modified into a form for use as an immunotoxin by removing the native targeting component of the toxin {e.g., domain Ia of PE or the B chain of DT) and replacing it with a different targeting moiety, such as an antibody.

Useful classes of cytotoxic or immunomodulatory drugs (also known as cytotoxins) include, for example, antitubulin agents, auristatins, DNA minor groove binders, DNA replication inhibitors, alkylating agents {e.g., platinum complexes such as cis-platin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, or the like.

Individual cytotoxic or immunomodulatory drugs include, for example, an androgen, anthramycin (AMC), asparaginase, 5-azacytidine, azathioprine, bleomycin, busulfan, buthionine sulfoximine, calicheamicin, camptothecin, carboplatin, carmustine (BSNU), CC-1065, chlorambucil, cisplatin, colchicine, cyclophosphamide, cytarabine (cytidine arabinoside), cytochalasin B, dacarbazine, dactinomycin (formerly actinomycin), daunorubicin, decarbazine, docetaxel, doxorubicin, etoposide, an estrogen, 5-fluordeoxyuridine, 5-fluorouracil, gemcitabine, gramicidin D, hydroxyurea, idarubicin, ifosfamide, irinotecan, lomustine (CCNU), maytansine, mechlorethamine, melphalan, 6-mercaptopurine, methotrexate, mithramycin, mitomycin C, mitoxantrone, nitroimidazole, paclitaxel, palytoxin, plicamycin, procarbizine, rhizoxin, streptozotocin, tenoposide, 6-thioguanine, thioTEPA, topotecan, vinblastine, vincristine, vinorelbine, VP-16 and VM-26.

In some typical embodiments, suitable cytotoxins include, for example, DNA minor groove binders {e.g., enediynes and lexitropsins, a CBI compound; see also U.S. Pat. No. 6,130,237), duocarmycins, taxanes {e.g., paclitaxel and docetaxel), puromycins, *vinca* alkaloids, CC-1065, SN-38, topotecan, morpholino-doxorubicin, rhizoxin, cyanomorpholino-doxorubicin, echinomycin, combretastatin, netropsin, epothilone A and B, estramustine, cryptophysins, cemadotin, maytansinoids, discodermolide, eleutherobin, and mitoxantrone.

In some embodiments, the cytotoxin is an anti-tubulin agent. Examples of anti-tubulin agents include, but are not limited to, taxanes {e.g., Taxol® (paclitaxel), Taxotere® (docetaxel)), T67 (Tularik; now Amgen South San Francisco) and vinca alkyloids {e.g., vincristine, vinblastine, vindesine, and vinorelbine). Other antitubulin agents include, for example, baccatin derivatives, taxane analogs {e.g., epothilone A and B), nocodazole, colchicine and colcimid, estramustine, cryptophysins, cemadotin, maytansinoids, combretastatins, discodermolide, and eleutherobin.

In certain embodiments, the cytotoxin is a maytansinoid, another group of anti-tubulin agents. For example, in specific embodiments, the maytansinoid is maytansine or DM-1 (ImmunoGen, Inc.; see also Chari et al., 1992, Cancer Res. 52:127-131).

In some embodiments, the cytotoxin is an auristatin, such as auristatin E or a derivative thereof. Typically, the auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatin derivatives include AFP, MMAF, and MMAE. The synthesis and structure of auristatin derivatives are described in U.S. Patent Application Publication Nos. 2003-0083263, 2005-0238649 and 2005-0009751; International Patent Publication No. WO 04/010957, International Patent Publication No. WO 02/088172, and U.S. Pat. Nos. 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414, each of which is incorporated by reference herein in its entirety.

In certain embodiments, the cytotoxin is an antimetabolite. The antimetabolite can be, for example, a purine antagonist {e.g., azothioprine or mycophenolate mofetil), a dihydrofolate reductase inhibitor {e.g., methotrexate), acyclovir, gangcyclovir, zidovudine, vidarabine, ribavarin, azidothymidine, cytidine arabinoside, amantadine, dideoxyuridine, iododeoxyuridine, poscarnet, or trifluridine.

In other embodiments, the cytotoxin is tacrolimus, cyclosporine or rapamycin. In further embodiments, the Drug is aldesleukin, alemtuzumab, alitretinoin, allopurinol, altretamine, amifostine, anastrozole, arsenic trioxide, bexarotene, bexarotene, calusterone, capecitabine, celecoxib, cladribine, Darbepoetin alfa, Denileukin diftitox, dexrazoxane, dromostanolone propionate, epirubicin, Epoetin alfa, estramustine, exemestane, Filgrastim, floxuridine, fludarabine, fulvestrant, gemcitabine, gemtuzumab ozogamicin, goserelin, idarubicin, ifosfamide, imatinib mesylate, Interferon alfa-2a, irinotecan, letrozole, leucovorin, levamisole, mechlorethamine or nitrogen mustard, megestrol, mesna, methotrexate, methoxsalen, mitomycin C, mitotane, nandrolone phenpropionate, oprelvekin, oxaliplatin, pamidronate, pegademase, pegaspargase, pegfilgrastim, pentostatin, pipobroman, plicamycin, porfimer sodium, procarbazine, quinacrine, rasburicase, Rituximab, Sargramostim, streptozocin, tamoxifen, temozolomide, teniposide, testolactone, thioguanine, toremifene, Tositumomab, Trastuzumab, tretinoin, uracil mustard, valrubicin, vinblastine, vincristine, vinorelbine and zoledronate.

In some embodiments, the cytotoxin is an immunomodulatory agent. The immunomodulatory agent can be, for example, gancyclovir, etanercept, tacrolimus, cyclosporine, rapamycin, cyclophosphamide, azathioprine, mycophenolate mofetil or methotrexate. Alternatively, the immunomodulatory agent can be, for example, a glucocorticoid {e.g., Cortisol or aldosterone) or a glucocorticoid analogue {e.g., prednisone or dexamethasone).

In some embodiments, the immunomodulatory agent is an antiinflammatory agent, such as arylcarboxylic derivatives, pyrazole-containing derivatives, oxicam derivatives and nicotinic acid derivatives. Classes of antiinflammatory agents include, for example, cyclooxygenase inhibitors, 5-lipoxygenase inhibitors, and leukotriene receptor antagonists.

Suitable cyclooxygenase inhibitors include meclofenamic acid, mefenamic acid, carprofen, diclofenac, diflunisal, fenbufen, fenoprofen, ibuprofen, indomethacin, ketoprofen, nabumetone, naproxen, sulindac, tenoxicam, tolmetin, and acetylsalicylic acid.

Suitable lipoxygenase inhibitors include redox inhibitors {e.g., catechol butane derivatives, nordihydroguaiaretic acid (NDGA), masoprocol, phenidone, lanopalen, indazolinones, naphazatrom, benzofuranol, alkylhydroxylamine), and non-redox inhibitors (e.g., hydroxythiazoles, methoxyalkylthiazoles, benzopyrans and derivatives thereof, methoxytetrahydropyran, boswellic acids and acetylated derivatives of boswellic acids, and quinolinemethoxyphenylacetic acids substituted with cycloalkyl radicals), and precursors of redox inhibitors.

Other suitable lipoxygenase inhibitors include antioxidants {e.g., phenols, propyl gallate, flavonoids and/or naturally occurring substrates containing flavonoids, hydroxylated derivatives of the flavones, flavonol, dihydroquercetin, luteolin, galangin, orobol, derivatives of chalcone, 4,2',4'-trihydroxychalcone, ortho-aminophenols, N-hydroxyureas, benzofuranols, ebselen and species that increase the activity of the reducing selenoenzymes), iron chelating agents {e.g., hydroxamic acids and derivatives thereof, N-hydroxyureas, 2-benzyl-1-naphthol, catechols, hydroxylamines, carnosol trolox C, catechol, naphthol, sulfasalazine, zyleuton, 5-hydroxyanthranilic acid and 4-(omega-arylalkyl)phenylalkanoic acids), imidazole-containing compounds {e.g., ketoconazole and itraconazole), phenothiazines, and benzopyran derivatives.

Yet other suitable lipoxygenase inhibitors include inhibitors of eicosanoids {e.g., octadecatetraenoic, eicosatetraenoic, docosapentaenoic, eicosahexaenoic and docosahexaenoic acids and esters thereof, PGE1 (prostaglandin E1), PGA2 (prostaglandin A2), viprostol, 15-monohydroxyeicosatetraenoic, 15-monohydroxy-eicosatrienoic and 15-monohydroxyeicosapentaenoic acids, and leukotrienes B5, C5 and D5), compounds interfering with calcium flows, phenothiazines, diphenylbutylamines, verapamil, fuscoside, curcumin, chlorogenic acid, caffeic acid, 5,8,11,14-eicosatetrayenoic acid (ETYA), hydroxyphenylretinamide, lonapalen, esculin, diethylcarbamazine, phenantroline, baicalein, proxicromil, thioethers, diallyl sulfide and di-(i-propenyl) sulfide.

Leukotriene receptor antagonists include calcitriol, ontazolast, Bayer Bay-x-1005, Ciba-Geigy CGS-25019C, ebselen, Leo Denmark ETH-615, Lilly LY-2931 11, Ono ONO-4057, Terumo TMK-688, Boehringer Ingleheim BI-RM-270, Lilly LY 213024, Lilly LY 264086, Lilly LY 292728, Ono ONO LB457, Pfizer 105696, Perdue Frederick PF 10042, Rhone-Poulenc Rorer RP 66153, SmithKline Beecham SB-201146, SmithKline Beecham SB-201993, SmithKline Beecham SB-209247, Searle SC-53228, Sumitamo SM 15178, American Home Products WAY 121006, Bayer Bay-o-8276, Warner-Lambert CI-987, Warner-Lambert CI-987BPC-15LY 223982, Lilly LY 233569, Lilly LY-255283, MacroNex MNX-160, Merck and Co. MK-591, Merck and Co. MK-886, Ono ONO-LB-448, Purdue Frederick PF-5901, Rhone-Poulenc Rorer RG 14893, Rhone-Poulenc Rorer RP 66364, Rhone-Poulenc Rorer RP 69698, Shionoogi S-2474, Searle SC-41930, Searle SC-50505, Searle SC-51 146, Searle SC-52798, SmithKline Beecham SK&F-104493, Leo Denmark SR-2566, Tanabe T-757 and Teijin TEM 338.

A "detectable label" means a diagnostic which has a property rendering its presence detectable. For example, a radioactive isotope which permits cells in which it is present to be detected in immunohistochemical assays.

The hNGAL muteins of the disclosure may optionally be covalently or non-covalently coupled to a detectable label. Detectable labels suitable for such use include any composition detectable by spectroscopic, photochemical, biochemical, immunochemical, electrical, optical or chemical means. Useful labels in the present disclosure include magnetic beads (e.g. DYNABEADS), fluorescent dyes (e.g., fluorescein isothiocyanate, Texas red, rhodamine, green fluorescent protein, and the like), radiolabels (e.g., 3H, 125I, 35S, 14C, or 32P), enzymes (e.g., horse radish peroxidase, alkaline phosphatase and others commonly used in an ELISA), and colorimetric labels such as colloidal gold or colored glass or plastic (e.g. polystyrene, polypropylene, latex) beads.

Means of detecting such labels are well known to those of skill in the art. Thus, for example, radiolabels may be detected using photographic film or scintillation counters, fluorescent markers may be detected using a photodetector to detect emitted illumination.

Enzymatic labels are typically detected by providing the enzyme with a substrate and detecting the reaction product produced by the action of the enzyme on the substrate, and colorimetric labels are detected by simply visualizing the colored label.

In another aspect, the present disclosure relates to the use of hNGAL muteins of the disclosure that be coupled to one or more detectable labels as diagnostics for detecting cancers associated with GPC-3 overexpression.

Specific cancers include hepatocellular cancer (HCC), melanoma, thyroid cancer, lung squamous cell carcinoma, Wilms' tumor, neuroblastoma, hepatoblastoma, and testicular germ-cell tumors.

The recitation of any reference in this application is not an admission that the reference is prior art to this application.

As used herein, the terms "Glypican-3, "glypican proteoglycan 3," "GPC-3, "OTTHUMP00000062492", "GTR2-2" "SGB," "DGSX", "SDYS", "SGBS", "OCI-5", and, "SGBSI" are used interchangeably, and include variants, isoforms and species homologs of human Glypican-3. The complete amino acid sequence of an exemplary human Glypican-3 has Genbank/NCBI accession number NM_004484.

As used herein, "polypeptide", "peptide" and "protein" are used interchangeably and include reference to a polymer of amino acid residues. The terms apply to amino acid polymers in which one or more amino acid residue is an artificial chemical analogue of a corresponding naturally occurring amino acid, as well as to naturally occurring amino acid polymers. The terms also apply to polymers containing conservative amino acid substitutions such that the protein remains functional.

The term "residue" or "amino acid residue" or "amino acid" includes reference to an amino acid that is incorporated into a protein, polypeptide, or peptide (collectively "peptide"). The amino acid can be a naturally occurring amino acid and, unless otherwise limited, can encompass known analogs of natural amino acids that can function in a similar manner as naturally occurring amino acids.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

All publications and patents cited in this disclosure are incorporated by reference in their entirety. To the extent the material incorporated by reference contradicts or is inconsistent with this specification, the specification will supersede any such material.

Unless otherwise indicated, the term "at least" preceding a series of elements is to be understood to refer to every element in the series. Those skilled in the art will recognize, or be able to ascertain using no more than routine experimentation, many equivalents to the specific embodiments of the disclosure described herein. Such equivalents are intended to be encompassed by the present disclosure.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or" as used herein.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the disclosure is not entitled to antedate such disclosure by virtue of prior disclosure.

Unless otherwise indicated, established methods of recombinant gene technology were used, for example, as described in Sambrook et al. (2001).

The disclosure is further illustrated by the following non-limiting Examples and the attached drawings. However, these Examples should not be construed so as to limit the disclosure. Rather, they are merely exemplary embodiments.

EXAMPLES

Example 1

The Evaluation of Cell Surface Binding of hNGAL Muteins (SEQ ID NOs: 2-6) in GPC-3 Positive Cells (SK Hep1:hGPC-3)

Incubation of SK Hep1:hGPC-3 and SK Hep1:EV (empty vector control) and HepG2 cells with hNGAL muteins (SEQ ID NOs: 1-6) and staining of GPC-3 and bound hNGAL muteins followed by confocal microscopy. Cells (SK Hep1: GPC-3, SK Hep1:EV or HepG2) were grown at 37° in a humidified CO2 incubator for 24 hrs and exposed to hNGAL muteins 1.0 ug/mL, fixed (4% PFA in PBS) and stained with a rabbit anti-lipocalin antibody overnight at 4° C. prior to addition of secondary donkey anti-rabbit AF568 antibody. For nuclei staining, cells were incubated in 300 uL of DAPI solution (1:50000 DAPI in PBS). Slides were viewed using Leica TCS SP5 DNI6000 CS Confocal Microscope (Leica) using the following lasers. FIG. 1 shows the cell surface staining of SKV-Hep1:hGPC-3 expressing cells by hNGAL muteins (SEQ ID NOs: 2-6) with no staining observed with vehicle group and lipocalin control (SEQ ID NO: 1). Results clearly indicate binding of all hNGAL muteins (SEQ ID NOs: 2-6) to the cell lines expressing GPC-3 (presence of GPC-3 on the surface of the cells was also confirmed by confocal imaging) and lack of binding of such hNGAL muteins to control cell line (SK-Hep1:EV).

Example 2

Figure 2:
FIG. 2 shows the internalization of GPC-3 specific hNGAL muteins (SEQ ID NOs: 2-6) to SKV-Hep1:hGPC-3 expressing cells by confocal microscopy. hNGAL muteins were detected using a Phycoerythrin (PE) labeled antibody. Positive staining is indicated by red punctate/granular intracellular staining. An acid wash was used to remove any cell surface staining (Confocal imaging showed lack of internalization of mutein controls).
Figure 3:
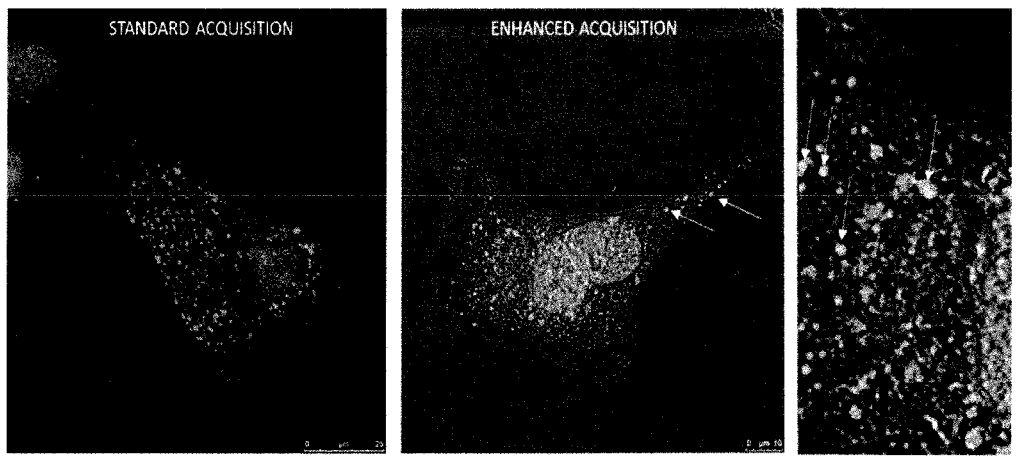
FIG. 3 shows the internalization of GPC-3 specific hNGAL muteins (SEQ ID NOs: 2-6) to SKV-Hep1:hGPC-3 expressing cells and co-localization with a lysosomal marker by confocal microscopy. hNGAL muteins were detected using a Phycoerythrin (PE) labeled antibody. Positive staining of a hNGAL mutein (SEQ ID NO: 6) is indicated by red punctate/granular intracellular staining while the lysosomal marker stains green. Co-localization of the hNGAL muteins and lysosomal marker is indicated by the orange staining. An acid wash was used to remove any cell surface staining (Confocal imaging showed lack of internalization of mutein controls).

Evaluation of Binding and Internalization of hNGAL Muteins (SEQ ID NOs: 2-6) to SK-HEP1:hGPC-3, SK-Hep1:EV and HepG2 Cells Cells were seeded (SK Hep1:GPC3, SK Hep1:EV and HepG2) at 20,000 cells/chamber in culture slides (BD Falcon) and grown at 37° in a humidified CO2 incubator for 24 hrs. (For lysosomal staining experiments, cells were incubated in serum free medium containing 1 uM lysotracker or 241 uM calcein for 30 min prior to moving to the next step). hNGAL muteins were added to 500 uL of growth medium (no FCS) at a final concentration of 1.0 ug/mL and left on ice for 5 min. The growth medium in culture chambers (apart from antibody controls) was replaced with medium containing the hNGAL muteins and incubated at 37° C. for 30 min. After incubation the cells were washed with acid strip buffer (50 mM glycine, 150 mM NaCl pH=3.0) for 15 sec and then washed and fixed (4% PFA in PBS). Cells were permeabilized (0.5% Triton X100 in PBS), blocked (1% BSA, 10% donkey serum in PBS) and incubated with 250 uL of rabbit anti-lipocalin antibody diluted or mouse anti-GPC-3 antibody overnight at 4° C. prior to washing with PBS (6×1 min). Donkey anti-rabbit AF568 antibody or donkey anti-mouse AF488 antibody (control GPC3 staining) was added to cells for 1 hr at RT in dark and washed with PBS (3×1 min). For nuclei staining cells were incubated in DAPI solution (1:50000 DAPI in PBS). Slides were viewed using Leica TCS SP5 DNI6000 CS Confocal Microscope (Leica) using the following lasers: UV (405 nm), argon (488 nm) HeNe (543 nm) and analyzed using Leica LAS AF software. Results in FIG. 2 clearly indicate binding and internalization of all hNGAL muteins (SEQ ID NOs: 2-6) to the cell lines expressing GPC-3, accompanied by a lack of binding to control cell line. Co-localization of hNGAL muteins with lysosomal markers (lysotracker or 241 uM calcein) was also assessed by confocal microscopy. hNGAL muteins were detected using a Phycoerythrin (PE) labeled antibody. FIG. 3 shows positive staining of a hNGAL mutein (SEQ ID NO: 6) indicated by red punctate/granular intracellular staining while co-localization of the hNGAL mutein and lysosomal marker is indicated by the orange staining.

Example 3

Evaluation of Internalization of hNGAL Muteins by Flow Cytometry

Figure 4:
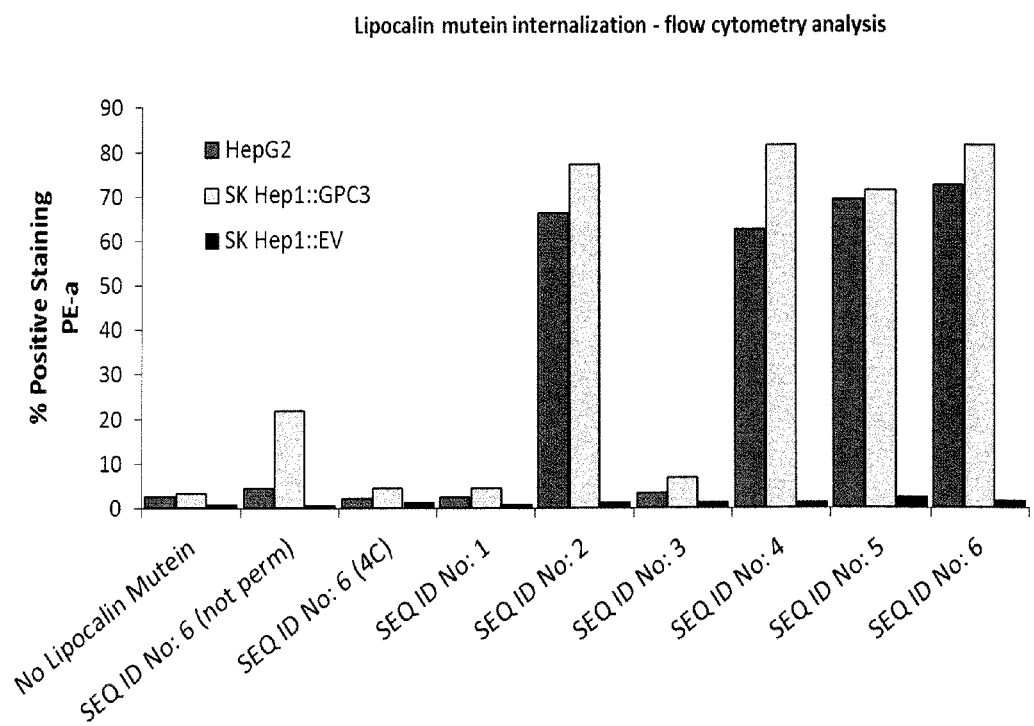
FIG. 4 shows the Flow cytometry (FACS) analysis of SKV-Hep1:hGPC-3, SKV-Hep1:EV (control) and HepG2 cells, demonstrating that the binding of hNGAL muteins (SEQ ID NOs: 2-6) to GPC-3 positive cells results in internalization. For analysis of internalization, an acid wash was used to remove any cell surface staining.

Cells (HepG2, SK Hep1:EV or SK Hep1:hGPC-3) were grown at 37° in a humidified CO2 incubator. hNGAL muteins (SEQ ID NOs: 1-6) at a final concentration of 1.0 ug/mL in growth medium was added to cells and incubated at 4° C. (control for acid strip efficiency) or 37° C. (to visualize hNGAL muteins internalization) for 30 min. After incubation cells were washed with 3 mL of ice cold PBS (1×1 min), 3 mL of ice cold acid strip buffer (50 mM glycine, 150 mM NaCl pH=3, 1×15 sec), 3 mL of ice cold PBS again (2×1 min). Harvested cells were spun in a centrifuge for 4 mins (300 g), re-suspended in 100 μl of Reagent A (Fixation Medium) and incubated for 15 min at room temperature. Cells were then washed once with 3 mL of PBS+5% FCS and vortexed. 100 uL of Reagent B (Permeabilization Buffer) was supplemented with anti-lipocalin antibody (1:2000), vortexed for 1 sec and left at RT for 20 min. For non-permeabilized sample PBS was used instead Reagent B. Cells were washed once with 3 mL of PBS+5% FCS, re-suspended in 100 uL of Reagent B supplemented with secondary antibody anti-rabbit-PE (1:200, 0.25 ug/sample) and left at RT for 20 min in the dark. For non-permeabilized sample PBS was used instead of Reagent B. Cells were washed once with 3 mL of PBS+5% FCS, re-suspended in 100 uL of 0.1% paraformaldehyde fixative solution for storage on ice in the dark. Fixed cells should be analysed within 24 hrs. FIG. 4 shows binding and internalisation of hNGAL muteins (SEQ ID NOs: 2, 4, 5 and 6) on GPC-3 positive cell lines (HepG2 and SK Hep1:hGPC-3) but no internalisation on control cells (SK Hep1:EV). While the hNGAL mutein (SEQ ID NO: 3) shows cell surface binding and internalization on GPC-3 positive cells by confocal microscopy the level of internalisation observed by FACS is modest compared to the other hNGAL muteins which may be due to a slower internalization rate. The variation in internalisation kinetics observed for the hNGAL muteins may be due to their differing binding affinities.

Example 4

Identification of GPC-3-Specific Tlc Muteins Using High-Throughput ELISA Screening Screening of GPC-3-specific Tlc muteins was performed essentially as described in Example 3 of international patent application WO 2006/56464.

The Tlc muteins (NO: 1-33 listed in FIG. 5; SEQ ID NOs: 11-43) were selected using Phage-Display-Methodology against biotinylated recombinant human GPC-3 (R&D 2119-GP/CF). Recombinant human GPC-3 expressed in NS0 cells was purchased from R&D systems and for selection experiments it was randomly biotinylated via Lysine residues using EZ-Link Sulfo-NHS-LC-LC-Biotin (Pierce) at a four-fold molar excess.

The affinity (IC50/EC50 values) of the Tlc muteins was determined as summarized in FIG. 5 (SEQ ID NOs: 11-43):

IC50: The Tlc muteins were diluted in a log 2 dilution-series (1000 µM starting point) in the presence of a fixed GPC-3 concentration (1 µM in solution). Samples were then transferred to a protein high-binding 384er plate with immobilized recombinant human GPC-3 protein. The bound lipocalin muteins were detected by a specific Antibody HRP conjugate complex. The value where 50% of lipocalin mutein bound to the immobilized recombinant human GPC3, is the IC50 value.

EC50: The Tlc muteins were diluted in a log 2 dilution-series (1000 µM start point) and transferred to a protein high-binding 384er plate with immobilized recombinant human GPC-3 protein. The bound lipocalin muteins were detected by a specific Antibody HRP conjugate complex. The value where 50% of Anticalins bounded to the immobilized recombinant human GPC-3 is the EC50 value.

Example 5

Affinity Measurement Using ELISA Techniques

An ELISA was performed to verify the binding affinity and specificity of the selected Tlc muteins. Therefore, a constant concentration of 1 µg/ml biotinylated human GPC-3 (R&D Systems) was captured on the surface of a polystyrol plate (Greiner, GE) via BSA blocked Neutravidin (Thermo Scientific, 5 µg/ml). Two step dilution series of purified Tlc muteins were incubated with the captured GPC-3 for 1 h at room temperature and detected either via the Strep-tag II using a rabbit anti-strep-tag II polyconal antibody (GenScript, USA) or by using a scaffold-specific polyclonal rabbit antibody. In both cases an anti-rabbit-IgG-HRP conjugate (Abcam, UK) was employed as secondary detection antibody.

The absorption ΔA at 320 nm was measured in an ELISA reader (Tecan, GE) and the data were fitted with Graphpad Prism software (Statcom, USA).

Results from measurements employing the Tlc muteins of the sequences of SEQ ID NO: 7 and SEQ ID NO: 8 as well as the protein of SEQ ID NO: 10 (listed in FIG. 5 as negative-control protein), used as a negative control, are summarized in Table 1.

TABLE 1

| Name | EC50 [nM] |
| --- | --- |
| SEQ ID NO: 7 | 5.1 |
| SEQ ID NO: 8 | 1.2 |
| SEQ ID NO: 10 | |

Figure 6:
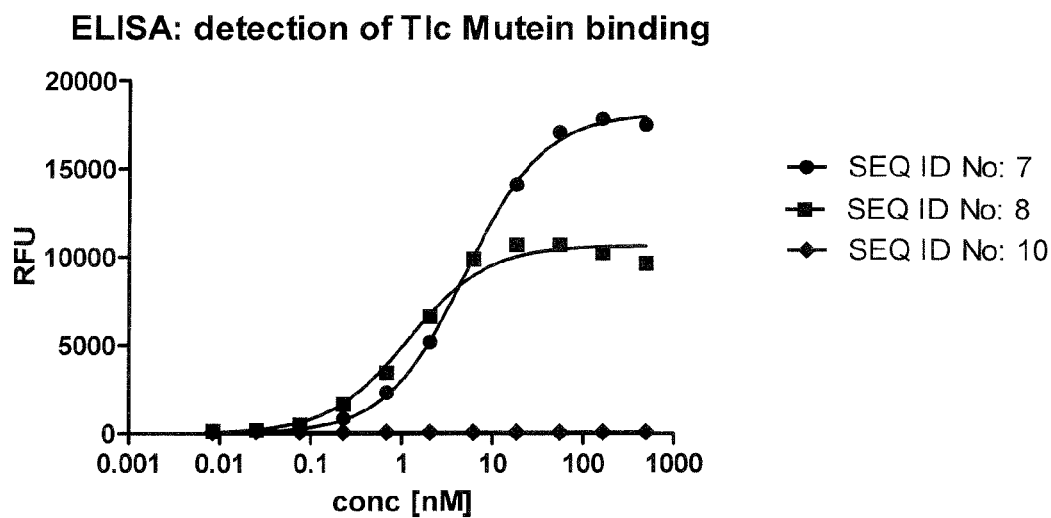
FIG. 6 depicts the binding-affinities of the selected Tlc muteins for human GPC-3 as determined by a direct ELISA. The protein (SEQ ID NO: 10), which revealed negligible signals in this assay for GPC-3, served as a negative control.

As shown in Table 1 above, affinity constants of muteins to the target human GPC-3: KD values of the selected Tlc muteins vary from 1.2 nM to 5.1 nM, whereas the negative control showed no binding at all. FIG. 6 gives a graphical demonstration of these data.

Example 6

Cell Surface Binding of GPC-3 Tlc Muteins on SK-Hep1 Transfectants

SK-HEP1 from the DSMZ cell bank, which do not express detectable levels of endogenous GPC-3, as assessed by flow cytometry were stably transfected with an expression vector encoding human GPC-3. Empty vector control cells were also obtained and analyzed in parallel. Expression of GPC-3 was also confirmed using a known mouse anti-GPC-3 clone 1G12 monoclonal antibody (DCS).

In order to assess binding of muteins to the GPC-3 on the cell surface, cells were incubated on ice with increasing concentrations of each lipocalin mutein for 2 hr. Following two washing steps cells were incubated with a secondary rabbit anti-Tlc scaffold antiserum was employed for 30 min. Detection was achieved with anti-rabbit IgG-PE (30 min.). Flow cytometry analysis was performed and geometric mean values were compiled in FlowJo (Treestar software) and fitted to a sigmoidal dose response model in the Prism 5 program (GraphPad) to obtain EC50 values.

Figure 7:
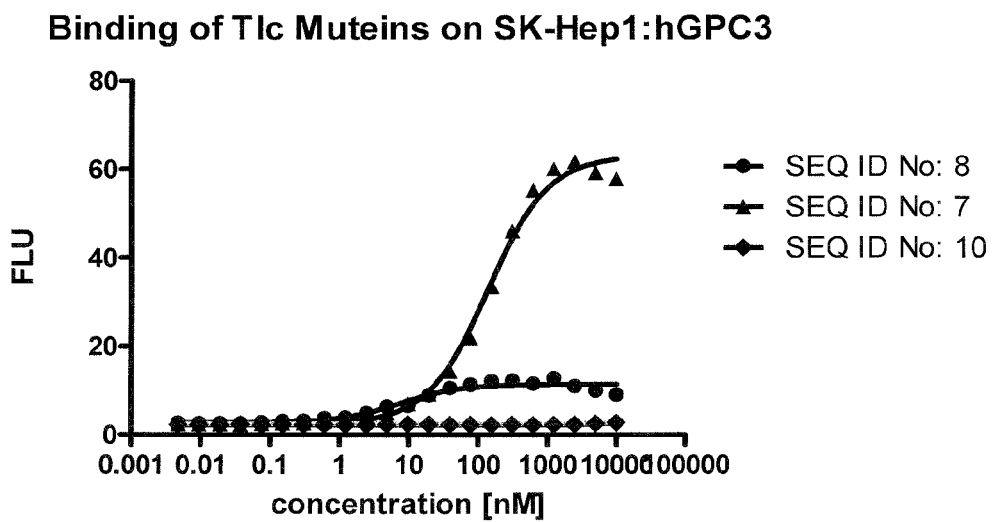
FIG. 7 depicts in a cell-based assay the specific binding of selected Tlc muteins to human GPC-3 transfected SK-Hep1 cells.

As graphically shown in FIG. 7, SEQ ID NO: 7 and SEQ ID NO: 8 specifically bind to human GPC-3 transfected SK-Hep1 cells while no binding is observed with the protein of SEQ ID NO: 10 (listed in FIG. 5 as negative-control protein) which was used as a negative control.

The invention has industrial applications in connection with treatment of diseases and/or conditions in which the GPC-3 expression contributes or is related to disease pathogenesis. The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention. The invention has been described broadly and generically herein. All patents, patent applications, textbooks and peer-reviewed publications described herein are hereby incorporated by reference in their entirety. Furthermore, where a definition or use of a term in a reference, which is incorporated by reference herein is inconsistent or contrary to the definition of that term provided herein, the definition of that term provided herein applies and the definition of that term in the reference does not apply. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group. Further embodiments of the invention will become apparent from the following claims.

The invention claimed is:

1. A human tear lipocalin mutein comprising a mutated amino acid residue at two or more positions corresponding to positions 26-34, 55-61, 64, 79, 101, 104-106, 108, 111, 114 and 153 of the amino acid sequence of the mature human tear lipocalin (SEQ ID NO: 9), wherein the mutein is capable of binding glypican-3 (GPC-3) with a $K_D$ of about 10 nM or lower, wherein the amino acid sequence of the mutein has at least 70% sequence identity to the amino acid sequence of the mature human tear lipocalin (SEQ ID NO: 9), and wherein the amino acid sequence of the mutein comprises the following amino acid substitution corresponding to the amino acid sequence of the mature human tear lipocalin (SEQ ID NO: 9): Arg 60→Tyr, Asp, Thr, Trp, Ile, Pro, Glu, Gln, Val, Ser, or Gly.

2. The mutein of claim 1, wherein the mutein is capable of competing for binding to GPC-3 in a competition assay with an IC50 or EC50 value of about 1 nM or lower.

3. The mutein of claim 1, wherein the mutein comprises 2, 3, 4, 5, 6, 7, 8, 9, 10, 11, 12, 13, 14, 15, 16, 17, 18, 19, 20 or 21 mutated amino acid residues at the sequence positions 26, 27, 28, 29, 30, 31, 32, 33, 34, 55, 56, 57, 58, 60, 61, 64, 79, 101, 104, 105, 106, 108, 111, 114 and 153 of the amino acid sequence of the mature human tear lipocalin (SEQ ID NO: 9).

4. The mutein of claim 1, wherein the amino acid sequence of the mutein further comprises at least one of the following amino acid substitutions: Arg 26→Asp, Thr, Ser, Gly, Phe, Tyr, Val or Glu, Glu 27→Thr, Asn, Asp, Arg, Leu, Phe or Val, Pro 29→Arg, Lys, Ser, Glu, Leu or Phe, Glu 30→Gly, Lys, Phe, Trp or Asn, Met 31→Ala, His, Leu, Trp, Gly, Ser or Arg, Asn 32→Tyr, Trp, Gln, His, Leu, Lys, Phe or Arg, Leu 33→Gln, His, Gly, Val, Glu or Phe, Glu 34→Gly, Asn, Pro, Trp, Arg or His, Met 55→Gln, Asn, Ile, Thr, Ser or Leu, Leu 56→Pro, Ser, Phe, Trp, Arg, Asn, Ala, Val, Asp, Gln, Glu or Thr, Ile 57→Leu or Ser, Ser 58→Asp, Trp, Phe, Ala, Glu, His, Asn, Pro or Val, Cys 61→Arg, Ser, Gly, Ala, Trp, Lys, Tyr, Asp, Val, Ile, Thr, Phe, Asn, Leu, Gln or Glu, Glu 104→Trp, Thr, Ser, His, Ala or Asp, and His 106→Ala, Tyr, Phe, Pro, Thr or Glu, and Lys 108→Leu, Ser, Phe or Trp.

5. The mutein of claim 4, wherein the amino acid sequence of the mutein further comprises one of the following sets of amino acid substitutions:
(1) Met 31→Ala, Asn 32→Arg, Glu 34→His, Leu 56→Trp, Ser 58→Asn, Arg 60→Trp; Cys 61→Arg; His 106→Glu; and Lys 108→Trp; or
(2) Met 31→Arg, Asn 32→Phe, Glu 34→Gly, Leu 56→Thr, Ser 58→Asp, Arg 60→Glu; Cys 61→Tyr; His 106→Ala; and Lys 108→Leu.

6. The mutein of claim 4, wherein the amino acid sequence of the mutein further comprises one of the following sets of amino acid substitutions:

(a) Arg 26→Thr; Glu 27→Leu; Phe 28→Cys; Met 31→Ala; Glu 34→Gly; Leu 56→Thr; Cys 61→Tyr; Ala 79→Val; Cys 101→Ser; Leu 105→Cys; His 106→Ala; Arg 111→Pro; Lys 114→Trp; Cys 153→Ser;

(b) Arg 26→Thr; Glu 27→Leu; Phe 28→Cys; Asn 32→Phe; Leu 33→Glu; Met 55→Asn; Cys 61→Tyr; Ala 79→Val; Cys 101→Ser; Leu 105→Cys; Lys 108→Leu; Arg 111→Pro; Lys 114→Trp; Cys 153→Ser;

(c) Arg 26→Thr; Glu 27→Leu; Phe 28→Cys; Glu 30→Gly; Leu 33→Glu; Glu 34→Gly; Leu 56→Thr; Ser 58→Asp; Cys 101→Ser; His 106→Ala; Lys 108→Leu; Arg 111→Pro; Lys 114→Trp; Cys 153→Ser;

(d) Arg 26→Thr; Phe 28→Cys; Glu 29→Arg; Asn 32→Tyr; Leu 56→Trp; Ile 57→Leu; Arg 60→Trp; Cys 61→Arg; Cys 101→Ser; Leu 105→Cys; Lys 108→Trp; Arg 111→Pro; Lys 114→Trp; Cys 153→Ser;

(e) Arg 26→Thr; Phe 28→Cys; Met 31→Ala; Asn 32→Tyr; Glu 34→His; Leu 56→Trp; Ser 58→Asn; Arg 60→Trp; Cys 101→Ser; Leu 105→Cys; His 106→Glu; Arg 111→Pro; Lys 114→Trp; Cys 153→Ser; or (f) Arg 26→Thr; Phe 28→Cys; Glu 29→Arg; Met 31→Ala; Leu 33→His; Ile 57→Leu; Ser 58→Asn; Cys 61→Arg; Cys 101→Ser; Glu 104→Asp; Lys 108→Trp; Arg 111→Pro; Lys 114→Trp; Cys 153→Ser.

7. The mutein of claim 1, wherein the amino acid sequence of the mutein further comprises at least one of the following amino acid substitutions: Arg 26→Thr; Glu 27→Leu; Phe 28→Cys; Pro 29→Phe; Glu 30→Gly; Leu 33→Glu; Met 55→Asn; Ile 57→Leu; Val 64→Trp; Val 64→Leu; Val 64→Asp; Val 64→Ala; Ala 79→Val; Cys 101→Ser; Glu 104→Asp; Leu 105→Cys; Arg 111→Pro; Lys 114→Trp and Cys 153→Ser.

8. The mutein of claim 1, comprising an amino acid sequence selected from the group consisting of SEQ ID NOs: 7-8 and 11-43 or at least 70% sequence identity to an amino acid sequence selected from the group consisting of SEQ ID NOs: 7-8 and 11-43.

9. The mutein of claim 1, wherein the mutein is conjugated to a compound that extends the serum half-life of the mutein or fused at its N-terminus and/or its C-terminus to a fusion partner.

10. The mutein of claim 1, wherein the amino acid sequence of the mutein further comprises at least one of the following amino acid substitutions corresponding to the amino acid sequence of the mature human tear lipocalin (SEQ ID NO: 9): Glu 30→Gly, Lys, Phe, Trp or Asn, and Leu 33→Gln, His, Gly, Val, Glu or Phe.

11. The mutein of claim 1, wherein the amino acid sequence of the mutein has at least 80% sequence identity to the amino acid sequence of the mature human tear lipocalin (SEQ ID NO: 9), and wherein the amino acid sequence of the mutein comprises at least 9 of the following amino acid substitutions corresponding to the amino acid sequence of the mature human tear lipocalin (SEQ ID NO: 9): Arg 26→Asp, Thr, Ser, Gly, Phe, Tyr, Val or Glu, Glu 27→Thr, Asn, Asp, Arg, Leu, Phe or Val, Pro 29→Arg, Lys, Ser, Glu, Leu or Phe, Glu 30→Gly, Lys, Phe, Trp or Asn, Met 31→Ala, His, Leu, Trp, Gly, Ser or Arg, Asn 32→Tyr, Trp, Gln, His, Leu, Lys, Phe or Arg, Leu 33→Gln, His, Gly, Val, Glu or Phe, Glu 34→Gly, Asn, Pro, Trp, Arg or His, Met 55→Gln, Asn, Ile, Thr, Ser or Leu, Leu 56→Pro, Ser, Phe, Trp, Arg, Asn, Ala, Val, Asp, Gln, Glu or Thr, Ile 57→Leu or Ser, Ser 58→Asp, Trp, Phe, Ala, Glu, His, Asn, Pro or Val, Arg 60→Tyr, Asp, Thr, Trp, Ile, Pro, Glu, Gln, Val, Ser, or Gly, Cys 61→Arg, Ser, Gly, Ala, Trp, Lys, Tyr, Asp, Val, Ile, Thr, Phe, Asn, Leu, Gln or Glu, Glu 104→Trp, Thr, Ser, His, Ala or Asp, and His 106→Ala, Tyr, Phe, Pro, Thr or Glu, and Lys 108→Leu, Ser, Phe or Trp.

12. The mutein of claim 1, wherein the amino acid sequence of the mutein has at least 85% sequence identity to the amino acid sequence of the mature human tear lipocalin (SEQ ID NO: 9), and wherein the amino acid sequence of the mutein comprises at least 12 of the following amino acid substitutions corresponding to the amino acid sequence of the mature human tear lipocalin (SEQ ID NO: 9): Arg 26→Asp, Thr, Ser, Gly, Phe, Tyr, Val or Glu, Glu 27→Thr, Asn, Asp, Arg, Leu, Phe or Val, Pro 29→Arg, Lys, Ser, Glu, Leu or Phe, Glu 30→Gly, Lys, Phe, Trp or Asn, Met 31→Ala, His, Leu, Trp, Gly, Ser or Arg, Asn 32→Tyr, Trp, Gln, His, Leu, Lys, Phe or Arg, Leu 33→Gln, His, Gly, Val, Glu or Phe, Glu 34→Gly, Asn, Pro, Trp, Arg or His, Met 55→Gln, Asn, Ile, Thr, Ser or Leu, Leu 56→Pro, Ser, Phe, Trp, Arg, Asn, Ala, Val, Asp, Gln, Glu or Thr, Ile 57→Leu or Ser, Ser 58→Asp, Trp, Phe, Ala, Glu, His, Asn, Pro or Val, Arg 60→Tyr, Asp, Thr, Trp, Ile, Pro, Glu, Gln, Val, Ser, or Gly, Cys 61→Arg, Ser, Gly, Ala, Trp, Lys, Tyr, Asp, Val, Ile, Thr, Phe, Asn, Leu, Gln or Glu, Glu 104→Trp, Thr, Ser, His, Ala or Asp, and His 106→Ala, Tyr, Phe, Pro, Thr or Glu, and Lys 108→Leu, Ser, Phe or Trp.

13. A pharmaceutical composition comprising the mutein of claim 1 and a pharmaceutically acceptable excipient.

14. A diagnostic or analytical kit comprising the mutein of claim 1.

15. A nucleic acid molecule comprising a nucleotide sequence encoding the mutein of claim 1.

16. A host cell containing a nucleic acid molecule of claim 15.

17. A method of producing the mutein of claim 1, wherein the mutein is produced in a cultured host cell comprising a nucleic acid molecule encoding for the mutein of claim 1.

* * * * *

SEQUENCE LISTING

```
<160> NUMBER OF SEQ ID NOS: 56

<210> SEQ ID NO 1
<211> LENGTH: 178
<212> TYPE: PRT
<213> ORGANISM: Homo sapiens
<220> FEATURE:
<223> OTHER INFORMATION: Human Lipocalin 2 (hNGAL)

<400> SEQUENCE: 1

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Ser Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 2
<211> LENGTH: 178
<212> TYPE: PRT
<213> ORGANISM: Artificial Sequence
<220> FEATURE:
<223> OTHER INFORMATION: Description of Artificial Sequence: Synthetic
      Mutein of hNGAL polypeptide

<400> SEQUENCE: 2

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30
```

```
Val Val Gly Ser Ala Gly Asn His Arg Leu Arg Glu Asp Lys Asp Pro
            35                  40                  45

Arg Lys Met His Ala Thr Ile Tyr Glu Leu Lys Glu Asp Lys Ser Tyr
 50                  55                  60

Asn Val Thr Asn Val Thr Phe Arg Glu Lys Lys Cys His Tyr Ser Ile
 65                  70                  75                  80

Gly Thr Phe Val Pro Gly Ser Gln Pro Gly Glu Phe Thr Leu Gly Lys
                 85                  90                  95

Ile Lys Ser Asn Pro Gly Met Thr Ser Phe Leu Val Arg Val Val Ser
                100                 105                 110

Thr Asn Tyr Asn Gln His Ala Met Val Phe Phe Lys Lys Val His Gln
            115                 120                 125

Asn Arg Glu Gln Phe Asn Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 3
<211> LENGTH: 178
<212> TYPE: PRT
<213> ORGANISM: Artificial Sequence
<220> FEATURE:
<223> OTHER INFORMATION: Description of Artificial Sequence: Synthetic
      Mutein of hNGAL polypeptide

<400> SEQUENCE: 3

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
                20                  25                  30

Val Val Gly Ile Ala Gly Asn Trp Ile Leu Arg Glu Asp Lys Asp Pro
            35                  40                  45

Pro Lys Met Arg Ala Thr Ile Tyr Glu Leu Lys Glu Asp Lys Ser Tyr
 50                  55                  60

Asn Val Thr Arg Val Arg Phe Asp Glu Lys Lys Cys Gly Tyr Gly Ile
 65                  70                  75                  80

Ala Thr Phe Val Pro Gly Ser Gln Pro Gly Glu Phe Thr Leu Gly Val
                 85                  90                  95

Ile Lys Ser Arg Pro Gly Ile Thr Ser Asp Leu Val Arg Val Val Ser
                100                 105                 110

Thr Asn Tyr Asn Gln His Ala Met Val Phe Phe Lys Phe Val Lys Gln
            115                 120                 125

Asn Arg Glu Tyr Phe Gly Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 4
<211> LENGTH: 178
<212> TYPE: PRT
```

-continued

<213> ORGANISM: Artificial Sequence
<220> FEATURE:
<223> OTHER INFORMATION: Description of Artificial Sequence: Synthetic
      Mutein of hNGAL polypeptide

<400> SEQUENCE: 4

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Met Ala Gly Asn Ala Arg Leu Arg Glu Asp Lys Asp Pro
        35                  40                  45

Val Lys Met Thr Ala Thr Ile Tyr Glu Leu Lys Glu Asp Lys Ser Tyr
    50                  55                  60

Asn Val Thr Ala Val Gln Phe Arg Leu Lys Lys Cys Gln Tyr Gly Ile
65                  70                  75                  80

Thr Thr Phe Val Pro Gly Ser Gln Pro Gly Glu Phe Thr Leu Gly Asp
                85                  90                  95

Ile Lys Ser Ile Pro Gly Leu Thr Ser Met Leu Val Arg Val Val Ser
            100                 105                 110

Thr Asn Tyr Asn Gln His Ala Met Val Phe Phe Lys Val Arg Gln
        115                 120                 125

Asn Arg Glu Phe Phe Asp Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 5
<211> LENGTH: 178
<212> TYPE: PRT
<213> ORGANISM: Artificial Sequence
<220> FEATURE:
<223> OTHER INFORMATION: Description of Artificial Sequence: Synthetic
      Mutein of hNGAL polypeptide

<400> SEQUENCE: 5

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Arg Ala Gly Asn Val Ala Leu Arg Glu Asp Lys Asp Pro
        35                  40                  45

Pro Lys Met Arg Ala Thr Ile Tyr Glu Leu Lys Glu Asp Lys Ser Tyr
    50                  55                  60

Asn Val Thr Asn Val Arg Phe Ala Met Lys Lys Cys Met Tyr Ser Ile
65                  70                  75                  80

Gly Thr Phe Val Pro Gly Ser Gln Pro Gly Glu Phe Thr Leu Gly Gln
                85                  90                  95

Ile Lys Ser Glu Pro Gly Asn Thr Ser Asn Leu Val Arg Val Val Ser
            100                 105                 110

Thr Asn Tyr Asn Gln His Ala Met Val Phe Phe Lys Glu Val Tyr Gln
        115                 120                 125

Asn Arg Glu Ile Phe Phe Ile Thr Leu Tyr Gly Arg Thr Lys Glu Leu
130                 135                 140

```
Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 6
<211> LENGTH: 178
<212> TYPE: PRT
<213> ORGANISM: Artificial Sequence
<220> FEATURE:
<223> OTHER INFORMATION: Description of Artificial Sequence: Synthetic
      Mutein of hNGAL polypeptide

<400> SEQUENCE: 6

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Val Ala Gly Asn Ala Met Leu Arg Glu Asp Lys Asp Pro
            35                  40                  45

Leu Lys Met Arg Ala Thr Ile Tyr Glu Leu Lys Glu Asp Lys Ser Tyr
50                  55                  60

Asn Val Thr Gly Val Ser Phe Trp Arg Lys Lys Cys His Tyr Lys Ile
65                  70                  75                  80

Gly Thr Phe Val Pro Gly Ser Gln Pro Gly Glu Phe Thr Leu Gly Asp
                85                  90                  95

Ile Lys Ser Gly Pro Gly Gln Thr Ser Asn Leu Val Arg Val Val Ser
                100                 105                 110

Thr Asn Tyr Asn Gln His Ala Met Val Phe Phe Lys Glu Val Arg Gln
                115                 120                 125

Asn Arg Glu Trp Phe Ala Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 7
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin polypeptide

<400> SEQUENCE: 7

Ala Ser Asp Glu Glu Ile Gln Asp Val Ser Gly Thr Trp Tyr Leu Lys
1               5                   10                  15

Ala Met Thr Val Asp Thr Leu Cys Pro Gly Arg Phe Glu Gly Ser Val
                20                  25                  30

Thr Pro Met Thr Leu Thr Thr Leu Glu Gly Gly Asn Leu Glu Ala Lys
            35                  40                  45

Val Thr Asn Thr Ile Asp Gly Glu Tyr Gln Glu Val Lys Ala Val Leu
50                  55                  60

Glu Lys Thr Asp Glu Pro Gly Lys Tyr Thr Val Asp Gly Gly Lys His
```

```
                     65                  70                  75                  80
Val Ala Tyr Ile Ile Arg Ser His Val Lys Asp His Tyr Ile Phe Tyr
                85                  90                  95

Ser Glu Gly Glu Cys Ala Gly Leu Pro Val Pro Gly Val Trp Leu Val
                100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
130                 135                 140

Gln Ser Glu Thr Ser Ser Pro Gly
145                 150

<210> SEQ ID NO 8
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin polypeptide

<400> SEQUENCE: 8

Ala Ser Asp Glu Glu Ile Gln Asp Val Ser Gly Thr Trp Tyr Leu Lys
1               5                   10                  15

Ala Met Thr Val Asp Thr Glu Cys Phe Glu Ala Arg Phe His Ser Val
                20                  25                  30

Thr Pro Met Thr Leu Thr Thr Leu Glu Gly Gly Asn Leu Glu Ala Lys
            35                  40                  45

Val Thr Met Trp Leu Asn Gly Trp Arg Gln Glu Val Lys Ala Val Leu
        50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Asp Cys Glu Gly Trp Pro Val Pro Gly Val Trp Leu Val
                100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
130                 135                 140

Gln Ser Glu Thr Ser Ser Pro Gly
145                 150

<210> SEQ ID NO 9
<211> LENGTH: 158
<212> TYPE: PRT
<213> ORGANISM: Homo sapiens
<220> FEATURE:
<223> OTHER INFORMATION: Human tear lipocalin

<400> SEQUENCE: 9

His His Leu Leu Ala Ser Asp Glu Glu Ile Gln Asp Val Ser Gly Thr
1               5                   10                  15

Trp Tyr Leu Lys Ala Met Thr Val Asp Arg Glu Phe Pro Glu Met Asn
                20                  25                  30

Leu Glu Ser Val Thr Pro Met Thr Leu Thr Thr Leu Glu Gly Gly Asn
            35                  40                  45

Leu Glu Ala Lys Val Thr Met Leu Ile Ser Gly Arg Cys Gln Glu Val
        50                  55                  60
```

```
Lys Ala Val Leu Glu Lys Thr Asp Glu Pro Gly Lys Tyr Thr Ala Asp
 65                  70                  75                  80

Gly Gly Lys His Val Ala Tyr Ile Ile Arg Ser His Val Lys Asp His
                 85                  90                  95

Tyr Ile Phe Tyr Cys Glu Gly Glu Leu His Gly Lys Pro Val Arg Gly
            100                 105                 110

Val Lys Leu Val Gly Arg Asp Pro Lys Asn Asn Leu Glu Ala Leu Glu
        115                 120                 125

Asp Phe Glu Lys Ala Ala Gly Ala Arg Gly Leu Ser Thr Glu Ser Ile
    130                 135                 140

Leu Ile Pro Arg Gln Ser Glu Thr Cys Ser Pro Gly Ser Asp
145                 150                 155

<210> SEQ ID NO 10
<211> LENGTH: 152
<212> TYPE: PRT
<213> ORGANISM: Artificial Sequence
<220> FEATURE:
<223> OTHER INFORMATION: Description of Artificial Sequence: Synthetic
      Negative-control polypeptide

<400> SEQUENCE: 10

Ala Ser Asp Glu Glu Ile Gln Asp Val Ser Gly Thr Trp Tyr Leu Lys
1               5                   10                  15

Ala Met Thr Val Asp Arg Glu Cys Pro Glu Met Asn Leu Glu Ser Val
            20                  25                  30

Thr Pro Met Thr Leu Thr Thr Leu Glu Gly Gly Asn Leu Glu Ala Lys
        35                  40                  45

Val Thr Met Leu Ile Ser Gly Arg Ser Gln Glu Val Lys Ala Val Leu
    50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Glu Cys His Gly Lys Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 11
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin polypeptide

<400> SEQUENCE: 11

Ala Ser Asp Glu Glu Ile Gln Asp Val Ser Gly Thr Trp Tyr Leu Lys
1               5                   10                  15

Ala Met Thr Val Asp Asp Thr Cys Pro Gly His Tyr Gln Gly Ser Val
            20                  25                  30

Thr Pro Met Thr Leu Thr Thr Leu Glu Gly Gly Asn Leu Glu Ala Lys
        35                  40                  45
```

```
Val Thr Met Pro Leu Asp Gly Asp Gly Gln Glu Val Lys Ala Val Leu
    50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Trp Cys Ala Gly Leu Pro Val Pro Gly Val Trp Leu Val
            100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Gln Ser Glu Thr Ser Ser Pro Gly
145                 150
```

<210> SEQ ID NO 12
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin polypeptide

<400> SEQUENCE: 12

```
Ala Ser Asp Glu Glu Ile Gln Asp Val Ser Gly Thr Trp Tyr Leu Lys
1               5                   10                  15

Ala Met Thr Val Asp Thr Glu Cys Arg Gly His Trp Gly Ser Val
            20                  25                  30

Thr Pro Met Thr Leu Thr Thr Leu Glu Gly Gly Asn Leu Glu Ala Lys
        35                  40                  45

Val Thr Gln Ser Ile Trp Gly Thr Ala Gln Glu Val Lys Ala Val Leu
    50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Glu Cys Ala Gly Leu Pro Val Pro Gly Val Trp Leu Val
            100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Gln Ser Glu Thr Ser Ser Pro Gly
145                 150
```

<210> SEQ ID NO 13
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin polypeptide

<400> SEQUENCE: 13

```
Ala Ser Asp Glu Glu Ile Gln Asp Val Ser Gly Thr Trp Tyr Leu Lys
1               5                   10                  15

Ala Met Thr Val Asp Ser Asn Cys Lys Lys Leu Gln Gly Asn Ser Val
            20                  25                  30
```

```
Thr Pro Met Thr Leu Thr Thr Leu Glu Gly Gly Asn Leu Glu Ala Lys
            35                  40                  45

Val Thr Met Phe Ile Trp Gly Trp Trp Gln Glu Val Lys Ala Val Leu
 50                  55                  60

Glu Lys Thr Asp Glu Pro Gly Lys Tyr Thr Ala Asp Gly Gly Lys His
 65                  70                  75                  80

Val Ala Tyr Ile Ile Arg Ser His Val Lys Asp His Tyr Ile Phe Tyr
                85                  90                  95

Ser Glu Gly Thr Cys Tyr Gly Ser Pro Val Pro Gly Val Trp Leu Val
            100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
 130                 135                 140

Gln Ser Glu Thr Ser Ser Pro Gly
145                 150
```

<210> SEQ ID NO 14
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin polypeptide

<400> SEQUENCE: 14

```
Ala Ser Asp Glu Glu Ile Gln Asp Val Ser Gly Thr Trp Tyr Leu Lys
 1               5                  10                  15

Ala Met Thr Val Asp Gly Thr Cys Ser Lys Leu His Gly Asn Ser Val
                20                  25                  30

Thr Pro Met Thr Leu Thr Thr Leu Glu Gly Gly Asn Leu Glu Ala Lys
            35                  40                  45

Val Thr Met Leu Ile Trp Gly Trp Lys Gln Glu Val Lys Ala Val Leu
 50                  55                  60

Glu Lys Thr Asp Glu Pro Gly Lys Tyr Thr Ala Asp Gly Gly Lys His
 65                  70                  75                  80

Val Ala Tyr Ile Ile Arg Ser His Val Lys Asp His Tyr Ile Phe Tyr
                85                  90                  95

Ser Glu Gly Ser Cys Phe Gly Ser Pro Val Pro Gly Val Trp Leu Val
            100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
 130                 135                 140

Gln Ser Glu Thr Ser Ser Pro Gly
145                 150
```

<210> SEQ ID NO 15
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin polypeptide

<400> SEQUENCE: 15

```
Ala Ser Asp Glu Glu Ile Gln Asp Val Ser Gly Thr Trp Tyr Leu Lys
 1               5                  10                  15
```

```
Ala Met Thr Val Asp Phe Asp Cys Glu Phe Trp Leu Val Pro Ser Val
            20                  25                  30

Thr Pro Met Thr Leu Thr Thr Leu Glu Gly Gly Asn Leu Glu Ala Lys
        35                  40                  45

Val Thr Met Trp Ile Phe Gly Ile Trp Gln Glu Trp Lys Ala Val Leu
 50                  55                  60

Glu Lys Thr Asp Glu Pro Gly Lys Tyr Thr Ala Asp Gly Gly Lys His
 65                  70                  75                  80

Val Ala Tyr Ile Ile Arg Ser His Val Lys Asp His Tyr Ile Phe Tyr
                 85                  90                  95

Ser Glu Gly Trp Cys Pro Gly Lys Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 16
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin polypeptide

<400> SEQUENCE: 16

Ala Ser Asp Glu Glu Ile Gln Asp Val Ser Gly Thr Trp Tyr Leu Lys
 1               5                  10                  15

Ala Met Thr Val Asp Tyr Arg Cys Leu Trp Gly Lys Leu Trp Ser Val
            20                  25                  30

Thr Pro Met Thr Leu Thr Thr Leu Glu Gly Gly Asn Leu Glu Ala Lys
        35                  40                  45

Val Thr Met Arg Leu Ala Gly Pro Lys Gln Glu Val Lys Ala Val Leu
 50                  55                  60

Glu Lys Thr Asp Glu Pro Gly Lys Tyr Thr Ala Asp Gly Gly Lys His
 65                  70                  75                  80

Val Ala Tyr Ile Ile Arg Ser His Val Lys Asp His Tyr Ile Phe Tyr
                 85                  90                  95

Ser Glu Gly His Cys Ala Gly Phe Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 17
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin polypeptide

<400> SEQUENCE: 17
```

Ala Ser Asp Glu Glu Ile Gln Asp Val Ser Gly Thr Trp Tyr Leu Lys
1               5                   10                  15

Ala Met Thr Val Asp Val Asp Cys Leu Asn Ser Tyr Leu Arg Ser Val
                20                  25                  30

Thr Pro Met Thr Leu Thr Thr Leu Glu Gly Gly Asn Leu Glu Ala Lys
            35                  40                  45

Val Thr Met Asn Ile His Gly Tyr Tyr Gln Glu Leu Lys Ala Val Leu
        50                  55                  60

Glu Lys Thr Asp Glu Pro Gly Lys Tyr Thr Ala Asp Gly Lys His
65                  70                  75                  80

Val Ala Tyr Ile Ile Arg Ser His Val Lys Asp His Tyr Ile Phe Tyr
                85                  90                  95

Ser Glu Gly Ala Cys Thr Gly Ser Pro Val Pro Gly Val Trp Leu Val
            100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Gln Ser Glu Thr Ser Ser Pro Gly
145                 150

<210> SEQ ID NO 18
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin polypeptide

<400> SEQUENCE: 18

Ala Ser Asp Glu Glu Ile Gln Asp Val Ser Gly Thr Trp Tyr Leu Lys
1               5                   10                  15

Ala Met Thr Val Asp Thr Leu Cys Pro Gly Arg Phe Glu Gly Ser Val
                20                  25                  30

Thr Pro Met Thr Leu Thr Thr Leu Glu Gly Gly Asn Leu Glu Ala Lys
            35                  40                  45

Val Thr Ile Ala Ile Asp Gly Glu Asp Gln Glu Val Lys Ala Val Leu
        50                  55                  60

Glu Lys Thr Asp Glu Pro Gly Lys Tyr Thr Ala Asp Gly Lys His
65                  70                  75                  80

Val Ala Tyr Ile Ile Arg Ser His Val Lys Asp His Tyr Ile Phe Tyr
                85                  90                  95

Ser Glu Gly Glu Cys Ala Gly Leu Pro Val Pro Gly Val Trp Leu Val
            100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Gln Ser Glu Thr Ser Ser Pro Gly
145                 150

<210> SEQ ID NO 19
<211> LENGTH: 152
<212> TYPE: PRT
<213> ORGANISM: Artificial Sequence
<220> FEATURE:
<223> OTHER INFORMATION: Description of Artificial Sequence: Synthetic Mutein of human tear lipocalin polypeptide

<400> SEQUENCE: 19

Ala Ser Asp Glu Glu Ile Gln Asp Val Ser Gly Thr Trp Tyr Leu Lys
1               5                   10                  15

Ala Met Thr Val Asp Thr Leu Cys Pro Gly Arg Phe Glu Gly Ser Val
            20                  25                  30

Thr Pro Met Thr Leu Thr Thr Leu Glu Gly Gly Asn Leu Glu Ala Lys
        35                  40                  45

Val Thr Asn Val Ile Asp Gly Glu Thr Gln Glu Val Lys Ala Val Leu
    50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Glu Cys Ala Gly Leu Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 20
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin polypeptide

<400> SEQUENCE: 20

Ala Ser Asp Glu Glu Ile Gln Asp Val Ser Gly Thr Trp Tyr Leu Lys
1               5                   10                  15

Ala Met Thr Val Asp Thr Glu Cys Phe Glu Ala Arg Phe His Ser Val
            20                  25                  30

Thr Pro Met Thr Leu Thr Thr Leu Glu Gly Gly Asn Leu Glu Ala Lys
        35                  40                  45

Val Thr Met Trp Leu Asn Gly Trp Arg Gln Glu Val Lys Ala Val Leu
    50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Asp Cys Glu Gly Trp Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 21
<211> LENGTH: 152
<212> TYPE: PRT

<213> ORGANISM: Artificial Sequence
<220> FEATURE:
<223> OTHER INFORMATION: Description of Artificial Sequence: Synthetic
      Mutein of human tear lipocalin polypeptide

<400> SEQUENCE: 21

Ala Ser Asp Glu Glu Ile Gln Asp Val Ser Gly Thr Trp Tyr Leu Lys
1               5                   10                  15

Ala Met Thr Val Asp Thr Leu Cys Pro Gly Arg Phe Glu Gly Ser Val
            20                  25                  30

Thr Pro Met Thr Leu Thr Thr Leu Glu Gly Gly Asn Leu Glu Ala Lys
        35                  40                  45

Val Thr Met Ala Ile Pro Gly Gln Val Gln Glu Val Lys Ala Val Leu
    50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Glu Cys Ala Gly Leu Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 22
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin polypeptide

<400> SEQUENCE: 22

Ala Ser Asp Glu Glu Ile Gln Asp Val Ser Gly Thr Trp Tyr Leu Lys
1               5                   10                  15

Ala Met Thr Val Asp Thr Leu Cys Pro Gly Arg Phe Glu Gly Ser Val
            20                  25                  30

Thr Pro Met Thr Leu Thr Thr Leu Glu Gly Gly Asn Leu Glu Ala Lys
        35                  40                  45

Val Thr Met Pro Ile Thr Gly Val Ile Gln Glu Val Lys Ala Val Leu
    50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Glu Cys Ala Gly Leu Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

```
<210> SEQ ID NO 23
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin polypeptide

<400> SEQUENCE: 23

Ala Ser Asp Glu Glu Ile Gln Asp Val Ser Gly Thr Trp Tyr Leu Lys
1               5                   10                  15

Ala Met Thr Val Asp Glu Phe Cys Pro Gly His Tyr Glu Gly Ser Val
                20                  25                  30

Thr Pro Met Thr Leu Thr Thr Leu Glu Gly Gly Asn Leu Glu Ala Lys
            35                  40                  45

Val Thr Asn Asp Ile Gln Gly Val Asp Gln Glu Val Lys Ala Val Leu
50                  55                  60

Glu Lys Thr Asp Glu Pro Gly Lys Tyr Thr Ala Asp Gly Lys His
65                  70                  75                  80

Val Ala Tyr Ile Ile Arg Ser His Val Lys Asp His Tyr Ile Phe Tyr
                85                  90                  95

Ser Glu Gly Trp Cys Tyr Gly Leu Pro Val Pro Gly Val Trp Leu Val
            100                 105                 110

Gly Arg Asp Pro Lys Asn Asn Leu Glu Ala Leu Glu Asp Phe Glu Lys
                115                 120                 125

Ala Ala Gly Ala Arg Gly Leu Ser Thr Glu Ser Ile Leu Ile Pro Arg
            130                 135                 140

Gln Ser Glu Thr Ser Ser Pro Gly
145                 150

<210> SEQ ID NO 24
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin polypeptide

<400> SEQUENCE: 24

Ala Ser Asp Glu Glu Ile Gln Asp Val Ser Gly Thr Trp Tyr Leu Lys
1               5                   10                  15

Ala Met Thr Val Asp Thr Leu Cys Pro Gly Arg Phe Glu Gly Ser Val
                20                  25                  30

Thr Pro Met Thr Leu Thr Thr Leu Glu Gly Gly Asn Leu Glu Ala Lys
            35                  40                  45

Val Thr Thr Trp Ser Glu Gly Glu Phe Gln Glu Val Lys Ala Val Leu
50                  55                  60

Glu Lys Thr Asp Glu Pro Gly Lys Tyr Thr Ala Asp Gly Lys His
65                  70                  75                  80

Val Ala Tyr Ile Ile Arg Ser His Val Lys Asp His Tyr Ile Phe Tyr
                85                  90                  95

Ser Glu Gly Glu Cys Ala Gly Leu Pro Val Pro Gly Val Trp Leu Val
            100                 105                 110

Gly Arg Asp Pro Lys Asn Asn Leu Glu Ala Leu Glu Asp Phe Glu Lys
                115                 120                 125

Ala Ala Gly Ala Arg Gly Leu Ser Thr Glu Ser Ile Leu Ile Pro Arg
            130                 135                 140

Gln Ser Glu Thr Ser Ser Pro Gly
```

```
145                 150

<210> SEQ ID NO 25
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin polypeptide

<400> SEQUENCE: 25

Ala Ser Asp Glu Glu Ile Gln Asp Val Ser Gly Thr Trp Tyr Leu Lys
1               5                   10                  15

Ala Met Thr Val Asp Thr Leu Cys Pro Gly Arg Phe Glu Gly Ser Val
            20                  25                  30

Thr Pro Met Thr Leu Thr Thr Leu Glu Gly Gly Asn Leu Glu Ala Lys
        35                  40                  45

Val Thr Met Trp Ile Asp Gly Val Ile Gln Glu Asp Lys Ala Val Leu
    50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Glu Cys Ala Gly Leu Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 26
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin polypeptide

<400> SEQUENCE: 26

Ala Ser Asp Glu Glu Ile Gln Asp Val Ser Gly Thr Trp Tyr Leu Lys
1               5                   10                  15

Ala Met Thr Val Asp Thr Leu Cys Pro Gly Arg Phe Glu Gly Ser Val
            20                  25                  30

Thr Pro Met Thr Leu Thr Thr Leu Glu Gly Gly Asn Leu Glu Ala Lys
        35                  40                  45

Val Thr Ser Asp Ile Leu Gly Val Asn Gln Glu Val Lys Ala Val Leu
    50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Glu Cys Ala Gly Leu Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
```

```
                130                 135                 140
Gln Ser Glu Thr Ser Ser Pro Gly
145                 150

<210> SEQ ID NO 27
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin polypeptide

<400> SEQUENCE: 27

Ala Ser Asp Glu Glu Ile Gln Asp Val Ser Gly Thr Trp Tyr Leu Lys
1               5                   10                  15

Ala Met Thr Val Asp Thr Leu Cys Pro Gly Arg Phe Glu Gly Ser Val
                20                  25                  30

Thr Pro Met Thr Leu Thr Thr Leu Glu Gly Gly Asn Leu Glu Ala Lys
            35                  40                  45

Val Thr Thr Ser Ile Glu Gly Glu Leu Gln Glu Val Lys Ala Val Leu
        50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Glu Cys Ala Gly Leu Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 28
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin polypeptide

<400> SEQUENCE: 28

Ala Ser Asp Glu Glu Ile Gln Asp Val Ser Gly Thr Trp Tyr Leu Lys
1               5                   10                  15

Ala Met Thr Val Asp Thr Leu Cys Pro Gly Arg Phe Glu Gly Ser Val
                20                  25                  30

Thr Pro Met Thr Leu Thr Thr Leu Glu Gly Gly Asn Leu Glu Ala Lys
            35                  40                  45

Val Thr Thr Gln Ile Asp Gly Ser Val Gln Glu Val Lys Ala Val Leu
        50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Glu Cys Ala Gly Leu Pro Val Pro Gly Val Trp Leu Val
            100                 105                 110

Gly Arg Asp Pro Lys Asn Asn Leu Glu Ala Leu Glu Asp Phe Glu Lys
```

```
        115                 120                 125
Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 29
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin polypeptide

<400> SEQUENCE: 29

Ala Ser Asp Glu Glu Ile Gln Asp Val Ser Gly Thr Trp Tyr Leu Lys
1               5                   10                  15

Ala Met Thr Val Asp Thr Leu Cys Pro Gly Arg Phe Glu Gly Ser Val
            20                  25                  30

Thr Pro Met Thr Leu Thr Thr Leu Glu Gly Gly Asn Leu Glu Ala Lys
        35                  40                  45

Val Thr Asn Leu Ile Asp Gly Gln Tyr Gln Glu Val Lys Ala Val Leu
    50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Glu Cys Ala Gly Leu Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 30
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin polypeptide

<400> SEQUENCE: 30

Ala Ser Asp Glu Glu Ile Gln Asp Val Ser Gly Thr Trp Tyr Leu Lys
1               5                   10                  15

Ala Met Thr Val Asp Thr Leu Cys Pro Gly Arg Phe Glu Gly Ser Val
            20                  25                  30

Thr Pro Met Thr Leu Thr Thr Leu Glu Gly Gly Asn Leu Glu Ala Lys
        35                  40                  45

Val Thr Gln Phe Ile Asp Gly Thr Leu Gln Glu Val Lys Ala Val Leu
    50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Glu Cys Ala Gly Leu Pro Val Pro Gly Val Trp Leu Val
```

```
                    100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 31
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin polypeptide

<400> SEQUENCE: 31

Ala Ser Asp Glu Glu Ile Gln Asp Val Ser Gly Thr Trp Tyr Leu Lys
1               5                   10                  15

Ala Met Thr Val Asp Thr Leu Cys Pro Gly Arg Phe Glu Gly Ser Val
            20                  25                  30

Thr Pro Met Thr Leu Thr Thr Leu Glu Gly Gly Asn Leu Glu Ala Lys
        35                  40                  45

Val Thr Ile Ala Ile Asp Gly Glu Asp Gln Glu Val Lys Ala Val Leu
    50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Glu Cys Ala Gly Leu Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 32
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin polypeptide

<400> SEQUENCE: 32

Ala Ser Asp Glu Glu Ile Gln Asp Val Ser Gly Thr Trp Tyr Leu Lys
1               5                   10                  15

Ala Met Thr Val Asp Glu Val Cys Pro Gly His Trp Glu Gly Ser Val
            20                  25                  30

Thr Pro Met Thr Leu Thr Thr Leu Glu Gly Gly Asn Leu Glu Ala Lys
        35                  40                  45

Val Thr Ile Ala Ile Asp Gly Glu Asp Gln Glu Val Lys Ala Val Leu
    50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
```

```
                        85                  90                  95

Ser Glu Gly Glu Cys Ala Gly Leu Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 33
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin polypeptide

<400> SEQUENCE: 33

Ala Ser Asp Glu Glu Ile Gln Asp Val Ser Gly Thr Trp Tyr Leu Lys
1               5                   10                  15

Ala Met Thr Val Asp Val Val Cys Pro Gly His Trp Glu Gly Ser Val
            20                  25                  30

Thr Pro Met Thr Leu Thr Thr Leu Glu Gly Gly Asn Leu Glu Ala Lys
        35                  40                  45

Val Thr Met Asp Leu Val Gly Thr Ala Gln Glu Val Lys Ala Val Leu
    50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Glu Cys Ala Gly Leu Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 34
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin polypeptide

<400> SEQUENCE: 34

Ala Ser Asp Glu Glu Ile Gln Asp Val Ser Gly Thr Trp Tyr Leu Lys
1               5                   10                  15

Ala Met Thr Val Asp Val Val Cys Pro Gly His Trp Glu Gly Ser Val
            20                  25                  30

Thr Pro Met Thr Leu Thr Thr Leu Glu Gly Gly Asn Leu Glu Ala Lys
        35                  40                  45

Val Thr Leu Glu Ile Asp Gly Asp Thr Gln Glu Val Lys Ala Val Leu
    50                  55                  60

Glu Lys Thr Asp Glu Pro Gly Lys Tyr Thr Ala Asp Gly Gly Lys His
```

```
                65                  70                  75                  80
Val Ala Tyr Ile Ile Arg Ser His Val Lys Asp His Tyr Ile Phe Tyr
                    85                  90                  95

Ser Glu Gly Glu Cys Ala Gly Leu Pro Val Pro Gly Val Trp Leu Val
                100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Gln Ser Glu Thr Ser Ser Pro Gly
145                 150

<210> SEQ ID NO 35
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin polypeptide

<400> SEQUENCE: 35

Ala Ser Asp Glu Glu Ile Gln Asp Val Ser Gly Thr Trp Tyr Leu Lys
1               5                   10                  15

Ala Met Thr Val Asp Thr Leu Cys Pro Gly Arg Phe Glu Gly Ser Val
                20                  25                  30

Thr Pro Met Thr Leu Thr Thr Leu Glu Gly Gly Asn Leu Glu Ala Lys
            35                  40                  45

Val Thr Met Ser Ile Glu Gly Val Thr Gln Glu Val Lys Ala Val Leu
        50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                    85                  90                  95

Ser Glu Gly Glu Cys Ala Gly Leu Pro Val Pro Gly Val Trp Leu Val
                100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Gln Ser Glu Thr Ser Ser Pro Gly
145                 150

<210> SEQ ID NO 36
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin polypeptide

<400> SEQUENCE: 36

Ala Ser Asp Glu Glu Ile Gln Asp Val Ser Gly Thr Trp Tyr Leu Lys
1               5                   10                  15

Ala Met Thr Val Asp Thr Leu Cys Pro Gly Arg Phe Glu Gly Ser Val
                20                  25                  30

Thr Pro Met Thr Leu Thr Thr Leu Glu Gly Gly Asn Leu Glu Ala Lys
            35                  40                  45

Val Thr Ser Leu Ile Glu Gly Glu Leu Gln Glu Val Lys Ala Val Leu
```

```
                 50                  55                  60
Glu Lys Thr Asp Glu Pro Gly Lys Tyr Thr Ala Asp Gly Lys His
 65                  70                  75                  80

Val Ala Tyr Ile Ile Arg Ser His Val Lys Asp His Tyr Ile Phe Tyr
                 85                  90                  95

Ser Glu Gly Glu Cys Ala Gly Leu Pro Val Pro Gly Val Trp Leu Val
                100                 105                 110

Gly Arg Asp Pro Lys Asn Asn Leu Glu Ala Leu Glu Asp Phe Glu Lys
                115                 120                 125

Ala Ala Gly Ala Arg Gly Leu Ser Thr Glu Ser Ile Leu Ile Pro Arg
                130                 135                 140

Gln Ser Glu Thr Ser Ser Pro Gly
145                 150

<210> SEQ ID NO 37
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin polypeptide

<400> SEQUENCE: 37

Ala Ser Asp Glu Glu Ile Gln Asp Val Ser Gly Thr Trp Tyr Leu Lys
 1               5                  10                  15

Ala Met Thr Val Asp Thr Leu Cys Pro Gly Arg Phe Glu Gly Ser Val
                20                  25                  30

Thr Pro Met Thr Leu Thr Thr Leu Glu Gly Gly Asn Leu Glu Ala Lys
                35                  40                  45

Val Thr Asn Thr Ile Asp Gly Glu Tyr Gln Glu Val Lys Ala Val Leu
                50                  55                  60

Glu Lys Thr Asp Glu Pro Gly Lys Tyr Thr Val Asp Gly Lys His
 65                  70                  75                  80

Val Ala Tyr Ile Ile Arg Ser His Val Lys Asp His Tyr Ile Phe Tyr
                 85                  90                  95

Ser Glu Gly Glu Cys Ala Gly Leu Pro Val Pro Gly Val Trp Leu Val
                100                 105                 110

Gly Arg Asp Pro Lys Asn Asn Leu Glu Ala Leu Glu Asp Phe Glu Lys
                115                 120                 125

Ala Ala Gly Ala Arg Gly Leu Ser Thr Glu Ser Ile Leu Ile Pro Arg
                130                 135                 140

Gln Ser Glu Thr Ser Ser Pro Gly
145                 150

<210> SEQ ID NO 38
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin polypeptide

<400> SEQUENCE: 38

Ala Ser Asp Glu Glu Ile Gln Asp Val Ser Gly Thr Trp Tyr Leu Lys
 1               5                  10                  15

Ala Met Thr Val Asp Thr Leu Cys Pro Gly Arg Phe Glu Gly Ser Val
                20                  25                  30

Thr Pro Met Thr Leu Thr Thr Leu Glu Gly Gly Asn Leu Glu Ala Lys
```

```
                    35                  40                  45
Val Thr Gln Phe Ile Asp Gly Glu Trp Gln Glu Val Lys Ala Val Leu
 50                  55                  60

Glu Lys Thr Asp Glu Pro Gly Lys Tyr Thr Ala Asp Gly Lys His
 65                  70                  75                  80

Val Ala Tyr Ile Ile Arg Ser His Val Lys Asp His Tyr Ile Phe Tyr
                     85                  90                  95

Ser Glu Gly Glu Cys Ala Gly Leu Pro Val Pro Gly Val Trp Leu Val
                    100                 105                 110

Gly Arg Asp Pro Lys Asn Asn Leu Glu Ala Leu Glu Asp Phe Glu Lys
                115                 120                 125

Ala Ala Gly Ala Arg Gly Leu Ser Thr Glu Ser Ile Leu Ile Pro Arg
130                 135                 140

Gln Ser Glu Thr Ser Ser Pro Gly
145                 150

<210> SEQ ID NO 39
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin polypeptide

<400> SEQUENCE: 39

Ala Ser Asp Glu Glu Ile Gln Asp Val Ser Gly Thr Trp Tyr Leu Lys
 1               5                  10                  15

Ala Met Thr Val Asp Thr Leu Cys Pro Gly Arg Phe Glu Gly Ser Val
                 20                  25                  30

Thr Pro Met Thr Leu Thr Thr Leu Glu Gly Gly Asn Leu Glu Ala Lys
             35                  40                  45

Val Thr Thr Phe Ile Asp Gly Ser Val Gln Glu Val Lys Ala Val Leu
 50                  55                  60

Glu Lys Thr Asp Glu Pro Gly Lys Tyr Thr Ala Asp Gly Lys His
 65                  70                  75                  80

Val Ala Tyr Ile Ile Arg Ser His Val Lys Asp His Tyr Ile Phe Tyr
                     85                  90                  95

Ser Glu Gly Glu Cys Ala Gly Leu Pro Val Pro Gly Val Trp Leu Val
                    100                 105                 110

Gly Arg Asp Pro Lys Asn Asn Leu Glu Ala Leu Glu Asp Phe Glu Lys
                115                 120                 125

Ala Ala Gly Ala Arg Gly Leu Ser Thr Glu Ser Ile Leu Ile Pro Arg
130                 135                 140

Gln Ser Glu Thr Ser Ser Pro Gly
145                 150

<210> SEQ ID NO 40
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin polypeptide

<400> SEQUENCE: 40

Ala Ser Asp Glu Glu Ile Gln Asp Val Ser Gly Thr Trp Tyr Leu Lys
 1               5                  10                  15

Ala Met Thr Val Asp Thr Leu Cys Pro Gly Arg Phe Glu Gly Ser Val
```

```
                  20                  25                  30
Thr Pro Met Thr Leu Thr Thr Leu Glu Gly Gly Asn Leu Glu Ala Lys
            35                  40                  45

Val Thr Gln Asp Ile Asp Gly Ile Gln Gln Glu Val Lys Ala Val Leu
        50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Glu Cys Ala Gly Leu Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150
```

<210> SEQ ID NO 41
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin polypeptide

<400> SEQUENCE: 41

```
Ala Ser Asp Glu Glu Ile Gln Asp Val Ser Gly Thr Trp Tyr Leu Lys
1               5                   10                  15

Ala Met Thr Val Asp Thr Leu Cys Pro Gly Arg Phe Glu Gly Ser Val
            20                  25                  30

Thr Pro Met Thr Leu Thr Thr Leu Glu Gly Gly Asn Leu Glu Ala Lys
        35                  40                  45

Val Thr Met Pro Ile Glu Gly Gly Ile Gln Glu Val Lys Ala Val Leu
    50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Glu Cys Ala Gly Leu Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150
```

<210> SEQ ID NO 42
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin polypeptide

<400> SEQUENCE: 42

Ala Ser Asp Glu Glu Ile Gln Asp Val Ser Gly Thr Trp Tyr Leu Lys

-continued

```
                1               5                  10                  15
Ala Met Thr Val Asp Thr Leu Cys Pro Gly Arg Phe Glu Gly Ser Val
                    20                  25                  30

Thr Pro Met Thr Leu Thr Thr Leu Glu Gly Gly Asn Leu Glu Ala Lys
            35                  40                  45

Val Thr Met Ala Ile Val Gly Val Glu Gln Glu Ala Lys Ala Val Leu
        50                  55                  60

Glu Lys Thr Asp Glu Pro Gly Lys Tyr Thr Ala Asp Gly Gly Lys His
 65                 70                  75                  80

Val Ala Tyr Ile Ile Arg Ser His Val Lys Asp His Tyr Ile Phe Tyr
                        85                  90                  95

Ser Glu Gly Glu Cys Ala Gly Leu Pro Val Pro Gly Val Trp Leu Val
                100                 105                 110

Gly Arg Asp Pro Lys Asn Asn Leu Glu Ala Leu Glu Asp Phe Glu Lys
                115                 120                 125

Ala Ala Gly Ala Arg Gly Leu Ser Thr Glu Ser Ile Leu Ile Pro Arg
            130                 135                 140

Gln Ser Glu Thr Ser Ser Pro Gly
145                 150
```

<210> SEQ ID NO 43
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin polypeptide

<400> SEQUENCE: 43

```
Ala Ser Asp Glu Glu Ile Gln Asp Val Ser Gly Thr Trp Tyr Leu Lys
 1               5                  10                  15

Ala Met Thr Val Asp Thr Leu Cys Pro Gly Arg Phe Glu Gly Ser Val
                    20                  25                  30

Thr Pro Met Thr Leu Thr Thr Leu Glu Gly Gly Asn Leu Glu Ala Lys
            35                  40                  45

Val Thr Met Trp Ile Glu Gly Gly Leu Gln Glu Val Lys Ala Val Leu
        50                  55                  60

Glu Lys Thr Asp Glu Pro Gly Lys Tyr Thr Ala Asp Gly Gly Lys His
 65                 70                  75                  80

Val Ala Tyr Ile Ile Arg Ser His Val Lys Asp His Tyr Ile Phe Tyr
                        85                  90                  95

Ser Glu Gly Glu Cys Ala Gly Leu Pro Val Pro Gly Val Trp Leu Val
                100                 105                 110

Gly Arg Asp Pro Lys Asn Asn Leu Glu Ala Leu Glu Asp Phe Glu Lys
                115                 120                 125

Ala Ala Gly Ala Arg Gly Leu Ser Thr Glu Ser Ile Leu Ile Pro Arg
            130                 135                 140

Gln Ser Glu Thr Ser Ser Pro Gly
145                 150
```

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 44

Asp Tyr Lys Asp Asp Asp Lys Gly
1               5

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Ser Met Thr Gly Gly Gln Gln Met Gly
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Pro Glu Leu Ala Pro Glu Asp Pro Glu Asp
1               5                   10

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Tyr Pro Tyr Asp Val Pro Asp Tyr Ala
1               5

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Cys Tyr Thr Asp Ile Glu Met Asn Arg Leu Lys
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Ala Pro Val Pro Tyr Pro Asp Pro Leu Glu Pro Arg
1               5                   10

<210> SEQ ID NO 50
<211> LENGTH: 12
<212> TYPE: PRT
```

<213> ORGANISM: Artificial Sequence
<220> FEATURE:
<223> OTHER INFORMATION: Description of Artificial Sequence: Synthetic peptide

<400> SEQUENCE: 50

Gly Val Ser Ser Thr Ser Ser Asp Phe Arg Asp Arg
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 51

Glu Glu Thr Ala Arg Phe Gln Pro Gly Tyr Arg Ser
1               5                   10

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 52

Lys Glu Thr Ala Ala Ala Lys Phe Glu Arg Gln His Met Asp Ser
1               5                   10                  15

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 53

Glu Gln Lys Leu Ile Ser Glu Glu Asp Leu
1               5                   10

<210> SEQ ID NO 54
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 54

Gly Lys Pro Ile Pro Asn Pro Leu Leu Gly Leu Asp Ser Thr
1               5                   10

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic 6xHis tag

<400> SEQUENCE: 55

His His His His His His
1               5

```
<210> SEQ ID NO 56
<211> LENGTH: 4
<212> TYPE: PRT
<213> ORGANISM: Homo sapiens

<400> SEQUENCE: 56

His His Leu Leu
1
```